US012084474B2

(12) United States Patent
Wu et al.

(10) Patent No.: US 12,084,474 B2
(45) Date of Patent: Sep. 10, 2024

(54) COMPOSITIONS AND METHODS FOR CHEMICAL CLEAVAGE AND DEPROTECTION OF SURFACE-BOUND OLIGONUCLEOTIDES

(71) Applicants: Illumina, Inc., San Diego, CA (US); Illumina Cambridge Limited, Cambridge (GB)

(72) Inventors: Xiaolin Wu, Cambridge (GB); Randall Smith, San Diego, CA (US); Peyton Shieh, Cambridge, MA (US); John M. Beierle, Carlsbad, CA (US); Wayne N. George, Cambridge (GB); Elliot John Lawrence, Cambridge (GB); Jie Mao, San Diego, CA (US); Xiaohai Liu, Cambridge (GB)

(73) Assignee: Illumina, Inc., San Diego, CA (US)

( * ) Notice: Subject to any disclaimer, the term of this patent is extended or adjusted under 35 U.S.C. 154(b) by 536 days.

(21) Appl. No.: 16/411,913

(22) Filed: May 14, 2019

(65) Prior Publication Data

US 2019/0352327 A1    Nov. 21, 2019

Related U.S. Application Data

(60) Provisional application No. 62/788,045, filed on Jan. 3, 2019, provisional application No. 62/671,816, filed on May 15, 2018.

(51) Int. Cl.
*C07H 21/04* (2006.01)
*C12Q 1/6806* (2018.01)
*C12Q 1/6876* (2018.01)

(52) U.S. Cl.
CPC .......... *C07H 21/04* (2013.01); *C12Q 1/6806* (2013.01); *C12Q 1/6876* (2013.01)

(58) Field of Classification Search
CPC .......... C07H 21/04; C07H 1/00; C07H 19/10; C07H 19/20; C12Q 1/6806; C12Q 1/6876; C12Q 1/6874; C12Q 2523/107; C12Q 2525/113; C12Q 2565/543; Y02P 20/55
See application file for complete search history.

(56) References Cited

U.S. PATENT DOCUMENTS

| | | | |
|---|---|---|---|
| 5,302,509 | A | 4/1994 | Cheeseman |
| 7,057,026 | B2 | 6/2006 | Barnes et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 9,012,022 | B2 | 4/2015 | George et al. |
| 2008/0108082 | A1 | 5/2008 | Rank et al. |
| 2009/0088327 | A1 | 4/2009 | Rigatti et al. |
| 2009/0118128 | A1 | 5/2009 | Liu et al. |
| 2010/0028885 | A1 | 2/2010 | Balasubramanian et al. |
| 2012/0156680 | A1 | 6/2012 | Ju et al. |
| 2014/0079923 | A1 | 3/2014 | George et al. |
| 2014/0242579 | A1 | 8/2014 | Zhou et al. |
| 2015/0005447 | A1 | 1/2015 | Berti et al. |

FOREIGN PATENT DOCUMENTS

| | | | |
|---|---|---|---|
| JP | 08-508489 | 9/1996 | |
| WO | WO 91/06678 | 5/1991 | |
| WO | WO 98/44151 | 10/1998 | |
| WO | WO 98/44152 | 10/1998 | |
| WO | WO 99/19474 A1 | 4/1999 | |
| WO | WO 00/18957 | 4/2000 | |
| WO | WO 01/027114 | 4/2001 | |
| WO | WO 02/003997 | 1/2002 | |
| WO | WO 2002/029003 | 4/2002 | |
| WO | WO 02/100354 | 12/2002 | |
| WO | WO 2004/018497 | 3/2004 | |
| WO | WO 2007/010251 | 1/2007 | |
| WO | WO-2007010251 A2 * | 1/2007 | ........... C12Q 1/6874 |
| WO | WO 07/134181 | 11/2007 | |
| WO | WO 2007/123744 | 11/2007 | |
| WO | WO 10/077578 | 7/2010 | |

(Continued)

OTHER PUBLICATIONS

Little (Nucleic Acids Research, 1996, vol. 24, No. 14 2793-2798).*
Wang (Bioorganic & Medicianl Chemistry Letters 9 (1999) pp. 885-890).*
Choueiry( Handbook of Organopalladium Chemistry for Organic Synthesis, pp. 47-65).*
Andersen, et al., "Nucleic acid secondary structures containing the double-headed nucleoside 5'(S)-C-(2-(thymin-1-yl)ethyl)thymidine", *Organic & Biomolecular Chemistry*, vol. 6, No. 21, 2008, p. 3983.
Ansorge et al., "Automated DNA sequencing: ultrasensitive detection of fluorescent bands during electrophoresis", *Nucl. Acids Res.* 15(11):4593-4602, 1987.
Ausubel et al., Current Protocols in Molecular Biology, John Wiley and Sons, Baltimore, Md. (1998).
Bentley et al., "Accurate whole human genome sequencing using reversible terminator chemistry", *Nature* 456:53-59 (2008).
Chen et al., "Universal Restriction Site-Free Cloning Method Using Chimeric Primers", Biotechniques, 2002, 32: 518-520.

(Continued)

*Primary Examiner* — Steven Pohnert
(74) *Attorney, Agent, or Firm* — Knobbe, Martens, Olson & Bear, LLP

(57) ABSTRACT

Embodiments of the present disclosure relate to methods of preparation of templates for polynucleotide sequencing. In particular, the disclosure relates to linearization of clustered polynucleotides in preparation for sequencing by cleavage of one or more first strands of double-stranded polynucleotides immobilized on a solid support by a transition metal complex, for example, a palladium complex or a nickel complex. Further disclosure relate to linearization of clustered polynucleotides by cleaving one or more second strands of double double-stranded polynucleotides immobilized on a solid support comprising azobenzene linker by $Na_2S_2O_4$. Nucleotides and oligonucleotides comprising a 3' phosphate moiety blocking group, and methods of removing the same using a fluoride reagent are also disclosed.

19 Claims, 12 Drawing Sheets

Specification includes a Sequence Listing.

(56) References Cited

FOREIGN PATENT DOCUMENTS

| WO | WO 13/022967 | 2/2013 | |
|---|---|---|---|
| WO | WO 13/154798 | 10/2013 | |
| WO | WO 2014/139596 | 9/2014 | |
| WO | WO-2017205336 A1 * | 11/2017 | ............. C07H 21/00 |

OTHER PUBLICATIONS

Connell et al., "Automated DNA Sequence Analysis", *BioTechniques* 5(4):342-384, 1987.

Ellis, et al., "Water-soluble tris(hydroxymethyl)phosphine complexes with nickel, palladium, and platinum. Crystal structure of [Pd{P(CH$_2$OH)$_3$}$_4$]•CH$_3$OH", *Inorg. Chem.*, 1992, 31, 14, pp. 3026-3033.

Greene & Wuts, 1999, Protective Groups in Organic Synthesis, Third Edition, John Wiley & Sons, New York.

Guillier et al., "Linkers and Cleavage Strategies in Solid-Phase Organic Synthesis and Combinatorial Chemistry", *Chem. Rev.* 100:2092-2157, 2000.

Kim, et al., "Synthesis of 3'-O-fluorescently mono-modified reversible terminators and their uses in sequencing-by-synthesis", *Bioorganic & Medicinal Chemistry Letters*, vol. 24. No. 1, Nov. 25, 2013 (Nov. 25, 2013), pp. 209-213.

Knapp, et al., "Fluoride-Cleavable, Fluorescently Labelled Reversible Terminators: Synthesis and Use in Primer Extension", *Chemistry—A European Journal*, vol. 17, No. 10, Feb. 3, 2011 (Feb. 3, 2011), pp. 2903-2915.

Koizumi, et al., "Biologically active oligodeoxyribonucleotides. Part 12:[1] N$^2$-Methylation of 2'- Deoxyguanosines Enhances Stability of Parallel G-Quadruplex and Anti-HIV-1 Activity", *Bioorganic & Medicinal Chemistry Letters*, Pergamon, Amsterdam, NL, vol. 10, No. 19, Oct. 2, 2000 (Oct. 2, 2000), pp. 2213-2216.

Komiyama et al., "Hydrolysis of DNA and RNA by lanthanide ions: mechanistic studies leading to new applications", Chem. Commun. 1999, 1443-1451.

Mardis, Elaine, "Next-Generation Sequencing Platforms", *Annual Review of Analytical Chemistry*, vol. 6, No. 1, Jun. 12, 2013 (Jun. 12, 2013), pp. 287-303.

Metzker et al., "Termination of DNA synthesis by novel 3' -modified-deoxyribonucleoside 5' -triphosphates", *Nucleic Acids Research*, 22 (20): 4259-4267, 1994.

Prober et al., "A System for Rapid DNA Sequencing with Fluorescent Chain-Terminating Dideoxynucleotides", *Science* 238:336-341, 1987.

Sambrook et al., *Molecular Cloning, A Laboratory Manual*, 3rd Ed, (2001) Cold Spring Harbor Laboratory Press, Cold Spring Harbor Laboratory Press, NY (Table of Contents).

Shida el al., "Cleavage of single- and double-stranded DNAs containing an abasic residue by *Escherichia coli* exonuclease III (AP endonuclease VI)", Nucleic Acids Research, 1996, vol. 24, 4572-4576.

Smith et al., "Fluorescence detection in automated DNA sequence analysis", *Nature* 321:674, 1986.

SØrensen, et al., "Synthesis of Conformationally Restricted Dinucleotides by Ring-Closing Metathesis", *Organic Letters*, vol. 2, No. 26, Dec. 2, 2000, pp. 4217-4219.

Tan, et al., "Design and synthesis of fluorescence-labeled nucleotide with a cleavable azo linker for DNA sequencing", *Chemical Communications*, vol. 52, No. 5, 2016, pp. 954-957.

Wang, et al., "Biophysical and biochemical properties of oligodeoxynucleotides containing 4'-C- and 5'-C-substituted thymidines", *Bioorg Med Chem Lett.*, vol. 9, No. 6, Mar. 22, 1999 (Mar. 22, 1999), pp. 885-890.

Welch et al., "Syntheses of Nucleosides Designed for Combinatorial DNA Sequencing", (*Chem. Eur. J.* 5(3):951-960, 1999).

Zhu et al., "Molecular Mechanism Controlling the Incorporation of Fluorescent Nucleotides Into DNA by PCR", *Cytometry* 28:206-211, 1997.

Andersen et al., 2008, Nucleic acid secondary structures containing the double-headed nucleoside 5'(S)-C-(2-(thymin-1-yl)ethyl)thymidine, Organic & Biomolecular Chemistry, 6(21):3983-3988.

Caulfield et al., 1994, Achiral internucleoside linkages 2: O—CH2—CH2 linkage, Bioorganic & Medicinal Chemistry Letters, 4(12):1497-1500.

Li et al., 2010, Free-radical ring closure to conformationally locked α-L-Carba-LNAs and synthesis of their oligos: nuclease stability, target RNA specificity, and elicitation of RNase H, Journal of Organic Chemistry, 75(18):6122-6140.

Sorensen et al., 2001, Synthesis and NMR-studies of dinucleotides with conformationally restricted cyclic phosphotriester linkages, Tetrahedron, 57:10191-10201.

Vrudhula et al., 1989, Approaches to isozyme-specific inhibitors. 16. A novel methyl-c5' covalent adduct of L-ethionine and ?,?-imido-ATP as a potent multisubstrate inhibitor of rat methionine adenosyltransferases, Journal of Medicinal Chemistry, 32(4):885-890.

* cited by examiner

```
                         SEQUENCE LISTING

<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Synthetic; P5: paired end
<220> FEATURE:
<221> NAME/KEY: misc_feature
<222> LOCATION: (23)..(23)
<223> OTHER INFORMATION: n = u

<400> SEQUENCE: 1
aatgatacgg cgaccaccga ganctacac                                   29

<210> SEQ ID NO 2
<211> LENGTH: 24
<212> TYPE: DNA
<213> ORGANISM: Artificial Sequence
<220> FEATURE:
<223> OTHER INFORMATION: Synthetic; P7: paired end
<220> FEATURE:
<221> NAME/KEY: misc_feature
<222> LOCATION: (22)..(22)
<223> OTHER INFORMATION: n = 8-oxo-guanine

<400> SEQUENCE: 2
caagcagaag acggcatacg anat                                        24

<210> SEQ ID NO 3
<211> LENGTH: 39
<212> TYPE: DNA
<213> ORGANISM: Artificial Sequence
```

```
<220> FEATURE:
<223> OTHER INFORMATION: Synthetic; P5 primer with poly-T spacer
<220> FEATURE:
<221> NAME/KEY: misc_feature
<222> LOCATION: (1)..(1)
<223> OTHER INFORMATION: 5'-alkyne
<220> FEATURE:
<221> NAME/KEY: misc_feature
<222> LOCATION: (33)..(33)
<223> OTHER INFORMATION: n = u

<400> SEQUENCE: 3
tttttttttt aatgatacgg cgaccaccga ganctacac                               39

<210> SEQ ID NO 4
<211> LENGTH: 34
<212> TYPE: DNA
<213> ORGANISM: Artificial Sequence
<220> FEATURE:
<223> OTHER INFORMATION: Synthetic; P7 primer with poly-T spacer
<220> FEATURE:
<221> NAME/KEY: misc_feature
<222> LOCATION: (1)..(1)
<223> OTHER INFORMATION: 5'-alkyne
<220> FEATURE:
<221> NAME/KEY: misc_feature
<222> LOCATION: (32)..(32)
<223> OTHER INFORMATION: n = 8-oxo-guanine

<400> SEQUENCE: 4
tttttttttt caagcagaag acggcatacg anat                                   34

<210> SEQ ID NO 5
<211> LENGTH: 35
<212> TYPE: DNA
<213> ORGANISM: Artificial Sequence
<220> FEATURE:
<223> OTHER INFORMATION: Synthetic; P15 primer
<220> FEATURE:
<221> NAME/KEY: misc_feature
<222> LOCATION: (1)..(1)
<223> OTHER INFORMATION: 5'-alkyne
<220> FEATURE:
<221> NAME/KEY: misc_feature
<222> LOCATION: (29)..(29)
<223> OTHER INFORMATION: n = allyl t nucleoside

<400> SEQUENCE: 5 tttttttaatg atacggcgac caccgaganc tacac                                 35

<210> SEQ ID NO 6
<211> LENGTH: 33
<212> TYPE: DNA
<213> ORGANISM: Artificial Sequence
<220> FEATURE:
<223> OTHER INFORMATION: Synthetic; P17 primer
<220> FEATURE:
<221> NAME/KEY: misc_feature
<222> LOCATION: (1)..(1)
<223> OTHER INFORMATION: 5'-alkyne
<220> FEATURE:
<221> NAME/KEY: misc_feature
<222> LOCATION: (7)..(7)
<223> OTHER INFORMATION: diol linker
<220> FEATURE:
<221> NAME/KEY: misc_feature
<222> LOCATION: (8)..(8)
<223> OTHER INFORMATION: diol linker
<220> FEATURE:
<221> NAME/KEY: misc_feature
<222> LOCATION: (9)..(9)
<223> OTHER INFORMATION: diol linker
```

```
<400> SEQUENCE: 6 tttttttnnnc aagcagaaga cggcatacga gat                                    33

<210> SEQ ID NO 7
<211> LENGTH: 20
<212> TYPE: DNA
<213> ORGANISM: Artificial Sequence
<220> FEATURE:
<223> OTHER INFORMATION: Synthetic; P5: single read

<400> SEQUENCE: 7
aatgatacgg cgaccaccga                                                    20

<210> SEQ ID NO 8
<211> LENGTH: 21
<212> TYPE: DNA
<213> ORGANISM: Artificial Sequence
<220> FEATURE:
<223> OTHER INFORMATION: Synthetic; P7: single read

<400> SEQUENCE: 8
caagcagaag acggcatacg a                                                  21
```

COMPOSITIONS AND METHODS FOR CHEMICAL CLEAVAGE AND DEPROTECTION OF SURFACE-BOUND OLIGONUCLEOTIDES

INCORPORATION BY REFERENCE TO PRIORITY APPLICATIONS

The present application claims the benefit of priority to U.S. Provisional Application Nos. 62/671,816, filed May 15, 2018 and 62/788,045, filed Jan. 3, 2019, each of which is incorporated by reference in its entirety.

SEQUENCE LISTING IN ELECTRONIC FORMAT

The present application is being filed along with an Electronic Sequence Listing as an ASCII text file via EFS-Web. The Electronic Sequence Listing is provided as a file entitled ILLINC363ASEQLIST.txt, created and last saved on May 10, 2019, which is 2,804 bytes in size. The information in the Electronic Sequence Listing is incorporated herein by reference in its entirety.

BACKGROUND

Field

Embodiments of the present disclosure relate to methods of preparation of templates for polynucleotide sequencing. In particular, the disclosure relates to linearization of clustered polynucleotides in preparation for sequencing by chemical cleavage of one or more first strands of double-stranded polynucleotides immobilized on a solid support, in some cases by reaction in the presence of a transition metal complex, such as a palladium complex or a nickel complex. Further, the disclosure relates to chemically-mediated deprotection of modified primers on a solid support.

Various nucleic acid sequencing methods are known in the art. U.S. Pat. No. 5,302,509 describes a method for sequencing a polynucleotide template that involves performing multiple extension reactions using a DNA polymerase or DNA ligase to successively incorporate labelled polynucleotides complementary to a template strand. In such a "sequencing by synthesis" (SBS) reaction, a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

In order to maximize the throughput of nucleic acid sequencing reactions it is advantageous to be able to sequence multiple template molecules in parallel. Parallel processing of multiple templates can be achieved with the use of nucleic acid array technology. These arrays typically consist of a high-density matrix of polynucleotides immobilized onto a solid support material.

Various methods for fabrication of arrays of immobilized nucleic assays have been described in the art. WO 98/44151 and WO 00/18957 both describe methods of nucleic acid amplification which allow amplification products to be immobilized on a solid support in order to form arrays comprised of clusters or "colonies" formed from a plurality of identical immobilized polynucleotide strands and a plurality of identical immobilized complementary strands. Arrays of this type are referred to herein as "clustered arrays." The nucleic acid molecules present in DNA colonies on the clustered arrays prepared according to these methods can provide templates for sequencing reactions, for example as described in WO 98/44152. The products of solid-phase amplification reactions such as those described in WO 98/44151 and WO 00/18957 are so-called "bridged" structures formed by annealing of pairs of immobilized polynucleotide strands and immobilized complementary strands, both strands being attached to the solid support at the 5' end. In order to provide more suitable templates for nucleic acid sequencing, it is preferred to remove substantially all or at least a portion of one of the immobilized strands in the "bridged" structure in order to generate a template which is at least partially single-stranded. The portion of the template which is single-stranded will thus be available for hybridization to a sequencing primer. The process of removing all or a portion of one immobilized strand in a "bridged" double-stranded nucleic acid structure is referred to as "linearization." There are various ways for linearization, including but not limited to enzymatic cleavage, photochemical cleavage, or chemical cleavage. Non-limiting examples of linearization methods are disclosed in PCT Publication No. WO 2007/010251 and U.S. Patent Publication No. 2009/0088327, and in U.S. Patent Publication No. 2009/0118128, which are incorporated by reference in their entireties.

Enzymatic methods are known to facilitate efficient site-specific cleavage of oligonucleotides or polynucleotides to linearize double stranded DNA clusters and to deprotect surface-bound primers. Currently, enzymes have been extensively used in both of these types of reactions in various sequencing applications. However, there are certain issues with the enzymatic approaches, including enzyme stability, costs of enzyme production, specific storage and handling requirements, variations in enzyme activity, and high background intensity in sequencing reading. Therefore, there exists a need to develop alternative linearization and deprotection methods for effective DNA sequencing. However, there are many limitations on the reaction types that can be applied to linearization steps in this context, as the reagents, conditions, and byproducts (a) must be compatible with up- and downstream reactions, including oligonucleotide hybridization and dehybridization, primer PCR extension, and DNA synthesis, (b) must display good stability under acidic, basic, and oxidative conditions, (c) must effect a rapid and clean chemical reaction, and (d) must not interfere with nucleotide detection methods. The present disclosure describes chemical cleavage and deprotection steps that are effective alternatives that meet the limitations described above.

SUMMARY

Some embodiments of the present disclosure relate to methods of linearizing a plurality of immobilized double-stranded polynucleotides, comprising: providing a solid support comprising double-stranded polynucleotides, wherein each double-stranded polynucleotide comprises a first strand and a second strand, wherein the first strand and the second strand are each immobilized to the solid support at their 5' ends, and wherein each first strand comprises a first cleavage site capable of undergoing chemical cleavage in the presence of a transition metal complex, wherein the transition metal complex is a palladium complex or a nickel complex; contacting the double-stranded polynucleotides with an aqueous solution of the transition metal complex, thereby cleaving one or more first strands at the first cleavage site, and generating one or more cleaved first nucleic acids and cleaved immobilized first strands; and removing the cleaved first nucleic acids from the solid support. In such methods, the immobilized second strand remains on the solid support following removal of the cleaved first nucleic acids from the solid support, and remains hybridized to the cleaved immobilized first strands. In some embodiments, the palladium (Pd) complex is a Pd(0) complex. In some embodiments, the nickel (Ni) complex is a Ni(0) complex. In some embodiments, the first cleavage site comprises allyl functionality. In some further embodiments, the first cleavage site further comprises a phosphate moiety. In some embodiments, the first cleavage site is a modified nucleoside or nucleotide comprising an allyl phosphate moiety.

The present disclosure is also related to methods of chemical deprotection of oligonucleotides on a solid support, comprising providing a solid support with a plurality of oligonucleotides immobilized thereon, wherein the oligonucleotides each comprise a protecting group on the 3' hydroxyl, such as a modified nucleotide or nucleoside containing a phosphate group that is capable of undergoing chemical deprotection, or a modified 3' terminal phosphate moiety, and reacting the oligonucleotides with a deprotecting reagent, thereby cleaving the protecting group (such as a modified 3' terminal phosphate moiety) to produce immobilized oligonucleotides with a free 3' hydroxyl group. In some aspects, the protecting group is a 3' terminal phosphate moiety with a structure of Formula (I):

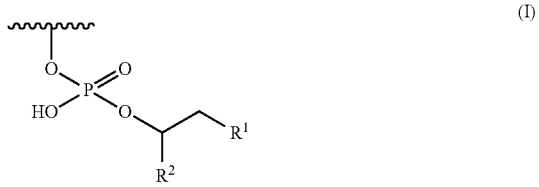

(I)

wherein the phosphate moiety is a phosphate at the 3' end of the immobilized oligonucleotide; $R^1$ is —$NH_2$, —OH, —NHC(O)$OR^a$ or —$OCH_2OSi(R^b)_3$;

wherein $R^a$ is $C_{1-4}$alkyl, tert-butyl, allyl, benzyl, or 9-fluorenylmethyl; and each $R^b$ is independently selected from the group consisting of $C_{1-4}$alkyl and phenyl; and $R^2$ is H, $C_{1-4}$ alkyl, an optionally substituted tetrahydrofuran, or a nucleotide.

In some aspects of Formula (I), $R^1$ is —NHC(O)$OR^a$. In some aspects, $R^a$ is 9-fluorenylmethyl, benzyl, or allyl. In some aspects, $R^1$ is —$OCH_2OSi(R^b)_3$. In some aspects, each $R^b$ is isopropyl. In some aspects, each $R^b$ is independently methyl, ethyl, tert-butyl, or phenyl.

In some aspects, the deprotecting reagent is fluoride ion (e.g., TBAF, HF, or CsF) or mild base (e.g., sodium hydroxide). In some aspects, the immobilized oligonucleotides are the cleaved immobilized first strands generated by the chemical cleavage of the first strands as described herein. Thus, in some aspects, the first strands comprise a modified nucleotide that is present in the cleaved immobilized first strands after cleaving and removing the cleaved first nucleic acids from the solid support. The methods described herein comprise removing the 3' hydroxyl protecting group of the cleaved immobilized first strands after the completion of Read 1. In some embodiments, the cleaved immobilized first strands comprise terminal phosphate groups. In other aspects, the methods comprise blocking the 3' terminal phosphate of the cleaved immobilized first strands after cleaving and removing the cleaved first nucleic acids from the solid support. In some aspects, the blocking is by reacting the 3' terminal phosphate with a blocking group prior to sequencing the immobilized second strands, and removing the blocking group after the completion of Read 1 to generate the 3' hydroxyl group according to the chemical cleavage methods described herein. The 3' ends of second strands remain hybridized to the immobilized cleaved first strands during and after the deprotection reaction.

In other aspects, the 3' hydroxyl protecting group is a phosphate group or moiety, which is present in the cleaved immobilized first strands following the first cleavage, and the methods comprise removing the phosphate group or moeity in the presence of a dephosphorylating enzyme such as T4PNK. The 3' ends of second strands remain hybridized to the immobilized cleaved first strands during and after the enzymatic deprotection reaction.

In some embodiments, the methods further comprise sequencing the immobilized second strands following removal of the cleaved first nucleic acids from the solid support. In some aspects, the sequencing comprises successively incorporating labeled nucleotides complementary to the immobilized second strands and detecting the labeled nucleotides after each successive incorporation. In paired-end sequencing, both strands of a double-stranded nucleic acid are ultimately sequenced, and in such cases, the sequencing of the immobilized second strand is referred to herein as "Read 1."

In other embodiments, each immobilized second strand comprises a second cleavage site capable of undergoing chemical cleavage. In some aspects, following sequencing of the second strands (Read 1), and removing the 3'hydroxyl protecting group from the immobilized cleaved first strands, the methods further comprise synthesizing the complements to the immobilized second strands to generate derivative double-stranded polynucleotides, wherein each derivative double-stranded polynucleotide comprises a second strand and a derivative first strand, wherein the derivative first strand and the second strand are each immobilized to the solid support at their 5' ends. Methods of the disclosure include cleaving one or more second strands at the second cleavage site, thereby generating one or more cleaved second nucleic acids and cleaved immobilized second strands, and removing the cleaved second nucleic acids from the solid support. In such methods, the immobilized derivative first strands remain on the solid support following removal of the cleaved second nucleic acids from the solid support, and remain hybridized to the cleaved immobilized second strands.

In some such embodiments, the second cleavage site of the second strand is capable of undergoing chemical cleavage, and the second strand is cleaved by a chemical reaction. For example, the second cleavage site comprises one or more vicinal diol linkages (that can be cleaved by oxidation, such as treatment with a periodate reagent), disulfide linkages (cleavable, for example, under reducing conditions such as DTT, or in the presence of a phosphine), ortho-nitrobenzyl groups (cleavable, for example, by photolysis), azobenzene linkages (cleavable, for example, in the presence of $Na_2S_2O_4$), alkyl-selenium linkages (cleavable, for example, by oxidation such as hydrogen peroxide), silyl ether linkages (cleavable, for example, by fluoride ion, acid, or base), or allyl carbamate linkages (cleavable, for example, in the presence of a palladium complex). In some aspects, the linkage is selected such that the second cleavage releases hydroxyl moieties. In some aspects, cleavage removes the linker reactive site (e.g., oxidation of a vicinal diol leaves two separate carbonyl compounds, and a diol is no longer present). In some aspects, the second cleavage site is at any position along the second strand, but preferably is attached on the backbone near the 5' end of the second strand (e.g., near the attachment to the solid support). In some embodiments, the chemical cleavage conditions for cleaving the first strand and the second strand are different, and the first strand and the second strand cannot be cleaved by the same cleaving condition (e.g., the cleavage sites are orthogonal). In some aspects, both cleavage steps need not be chemical cleavage steps. For example, the first strands may be cleaved by enzymatic reaction, while the second strands are cleaved by chemical reaction, or the first strands may be cleaved by chemical reaction, while the second strands are cleaved by enzymatic reaction.

Some additional embodiments of the present disclosure relate to methods of linearizing a plurality of immobilized double-stranded polynucleotides, comprising: providing a solid support comprising double-stranded polynucleotides, each double-stranded polynucleotide comprises a first strand and a second strand, wherein the first strand and the second strand are immobilized to the solid support at their 5' ends, wherein each first strand comprises a first cleavage site, and wherein each second strand comprises a second cleavage site comprising an azobenzene linker; cleaving one or more first strands at the first cleavage site, and generating one or more cleaved first nucleic acids and cleaved immobilized first strands; removing the cleaved first nucleic acids from the solid support; sequencing the immobilized second strands; resynthesizing derivative first strands that are complementary to the second strands; and cleaving one or more second strands at the second cleavage site, and generating one or more cleaved second nucleic acids and cleaved immobilized second strands. In some aspects of such methods, the immobilized derivative first strands remain on the solid support following removal of the cleaved second nucleic acids from the solid support, and remain hybridized to the cleaved immobilized second strands.

In some aspects, the methods further comprise sequencing the immobilized derivative first strands following removal of the cleaved second nucleic acids from the solid support. In some aspects, the sequencing comprises successively incorporating labeled nucleotides complementary to the immobilized derivative first strands and detecting the labeled nucleotides after each successive incorporation. In paired-end sequencing, both strands of a double-stranded nucleic acid are ultimately sequenced, and in such cases, the sequencing of the immobilized derivative first strand is referred to herein as "Read 2."

Some embodiments of the present disclosure relate to methods of preparing a 3' blocking moiety that can be removed by a chemical reaction in the paired-end sequencing method (described in U.S. Publication No. 2009/0088327, which is incorporated by reference in its entirety). The methods comprise: providing a solid support comprising double-stranded polynucleotides, each double-stranded polynucleotide comprises a first strand and a second strand, wherein the first strand and the second strand are immobilized to the solid support at their 5' ends, and wherein each first strand comprises a first cleavage site; cleaving one or more first strands at the first cleavage site to generate one or more cleaved first nucleic acids and cleaved immobilized first strands; and introducing a 3' blocking moiety to the 3' end of the cleaved immobilized first strands, wherein the 3' blocking moiety can be removed by a chemical reaction. In some other embodiments, instead of introducing the 3' blocking moiety to the 3' end of the cleaved immobilized first strands, the 3' blocking moiety is generated from the first cleavage site after said cleaving step. In some embodiments, the 3' blocking moiety comprises a modified nucleoside or nucleotide containing a phosphate moiety. In one such embodiment, the 3' blocking moiety comprises a modified nucleoside, the modified nucleoside contains an extra —CH$_2$OH or protected —CH$_2$OH at the 5' positon of the nucleoside. In another such embodiment, the 3' blocking moiety comprises a modified nucleoside, the modified nucleoside contains an extra —CH$_2$NH$_2$ or protected —CH$_2$NH$_2$ at the 5' positon of the nucleoside. In some embodiments, the methods further comprise removing the 3' blocking moiety in a chemical reaction, for example, in an aqueous solution comprising a fluoride agent or a base.

Some embodiments of the present disclosure relate to a solid support comprising a plurality of first strand polynucleotides immobilized thereon, each first strand polynucleotide comprises a first cleavage site capable of undergoing chemical cleavage by a palladium complex or a nickel complex, wherein the plurality of first strand polynucleotides are immobilized to the solid support at their 5' ends. In some embodiments, the solid support further comprises a plurality of second strand polynucleotides immobilized thereon, each second strand polynucleotide comprises a second cleavage site, wherein the plurality of second strand polynucleotides are immobilized to the solid support at their 5' ends. In some embodiments, the palladium complex is a palladium (0) complex. In some embodiments, the first cleavage site comprises an allyl functionality. In one embodiment, the first cleavage site comprises an allyldT. In some further embodiments, the first cleavage site further comprises a phosphate moiety, which remains on the cleaved immobilized first strand after chemical cleavage. In one embodiment, the phosphate moiety comprises the structure of Formula (I). In some embodiments, the second cleavage site may be cleaved by a method selected from the group consisting of chemical cleavage, photo cleavage, enzymatic cleavage, or a combination thereof. In one embodiment, the second cleavage site is cleaved by a chemical cleavage reaction. In some such embodiments, the second cleavage site may comprise a diol linker of Formula (VIII) or (VIIIa), or an azobenzene linker of Formula (X) as described below.

The disclosure is also directed to modified nucleoside or nucleotides and oligonucleotides and methods of preparing such compounds. In one aspect, the modified nucleoside or modified nucleotide comprises the structure of Formula (II):

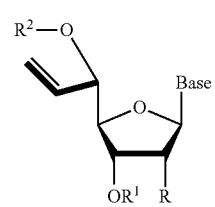

(II)

wherein R is H, OH or OPG; R$^1$ is H or PG; R$^2$ is H, PG, or —OR$^2$ is a phosphate group; PG is a hydroxyl protecting group; Base is adenine, guanine, cytosine, thymine, or uracil, or a derivative thereof. In some embodiments, the phosphate group may be negatively charged (e.g., —PO$_4^-$). In one aspect, the modified nucleoside or nucleotide has the structure of Formula (IIa):

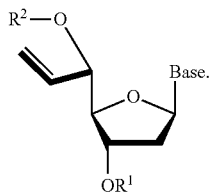

(IIa)

In one aspect is a modified nucleoside or nucleotide comprising the structure of Formula (II') when the modified nucleoside or nucleotide of Formula (II) is incorporated into an oligonucleotide or polynucleotide, where the 3' oxygen of the allyl modified nucleoside or nucleotide is covalently attached to the 5' end of another nucleotide (structure not shown):

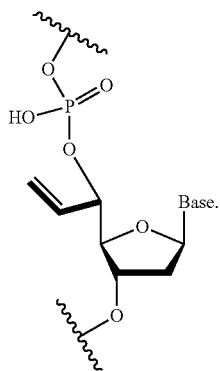

(II')

In some embodiments, the phosphate group may be negatively charged (e.g., —PO$_4^-$).

In another aspect is an oligonucleotide comprising an allyl nucleoside or nucleotide, where the oligonucleotide is a compound of Formula (III):

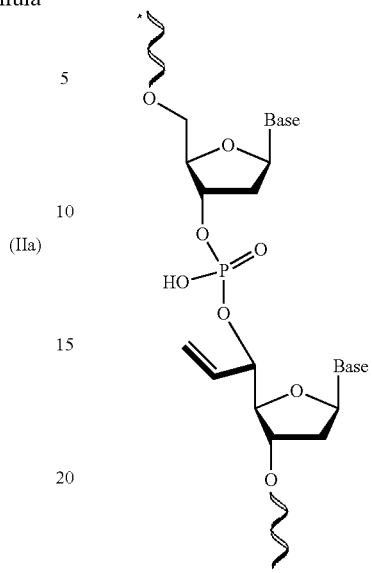

(III)

wherein each Base is independently adenine, guanine, cytosine, thymine, or uracil, or a derivative thereof; and the oligonucleotide is optionally bound to a solid support. In some embodiments, the phosphate group may be negatively charged (e.g., —PO$_4^-$).

In some aspects, the 5' end of the oligonucleotide (at the asterisk) is bound to a solid support.

Additional disclosure relates to a chemical reagent for incorporating an allyl nucleotide into a polynucleotide, wherein the chemical reagent is a compound of Formula (IV):

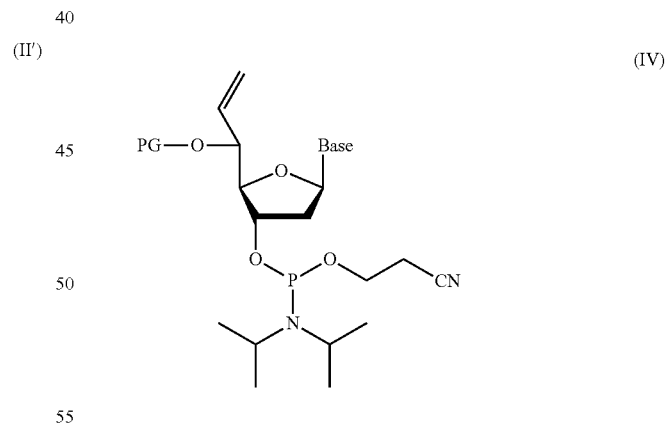

(IV)

wherein PG is H or a hydroxyl protecting group; and Base is adenine, guanine, cytosine, thymine, or uracil, or a derivative thereof.

In some aspects, PG is a protecting group that is cleavable under mild acidic conditions. In some aspects, PG is trityl or dimethoxytrityl (DMT).

In some aspects is a method of making the compound of Formula (IV) comprising: reacting the compound of formula A:

formula A

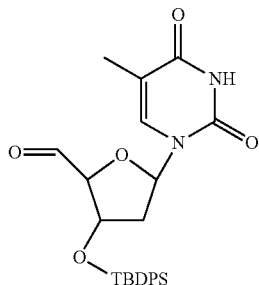

with a vinyl Grignard reagent (such as vinylMgCl or vinylMgBr), optionally at room temperature, to form the compound of formula B:

formula B

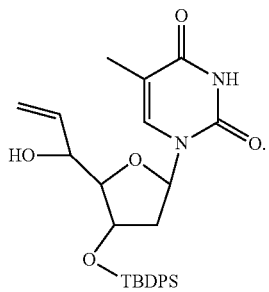

In some aspects, the method comprises oxidizing the compound of formula C (optionally via a Pfitzner-Moffatt oxidation, or using 1-ethyl-3-(3-dimethylaminopropyl)carbodiimide (EDC) or N,N'-dicyclohexylcarbodiimide (DCC), dichloroacetic acid (DCA), and DMSO):

formula C

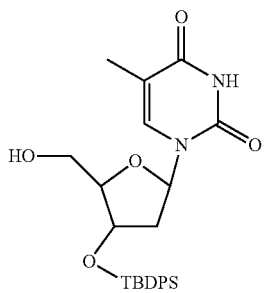

to form the compound of formula A.

In some aspects, the method comprises reacting the compound of formula D:

formula D

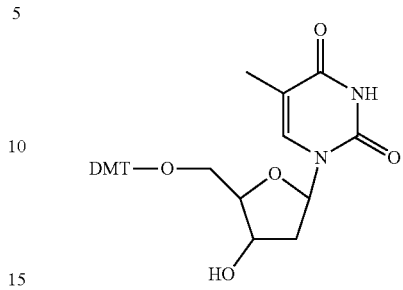

with TBDPSCl (tert-butyldiphenylsilyl chloride) in the presence of a base (such as imidazole) followed by a mild acid such as PTSA (p-toluenesulfonic acid) in a one-pot procedure without isolating the bis-protected intermediate, to form the compound of formula C.

In another aspect is a nucleoside or nucleotide comprising a 3' blocking moiety of a structure of Formula (I):

(I)

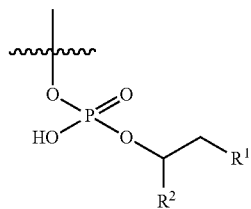

wherein $R^1$ is —$NH_2$, —OH, —NHC(O)$OR^a$ or —$OCH_2OSi(R^b)_3$; $R^a$ is $C_{1-4}$ alkyl, tert-butyl, allyl, benzyl, or 9-fluorenylmethyl; each $R^b$ is independently selected from the group consisting of $C_{1-4}$ alkyl and phenyl; and $R^2$ is H, $C_{1-4}$ alkyl, an optionally substituted tetrahydrofuran, or a nucleotide. In some embodiments, the phosphate group may be negatively charged (e.g., $PO_4^-$).

In another aspect is a 3' phosphate modified nucleoside or nucleotide comprising the structure of Formula (V):

(V)

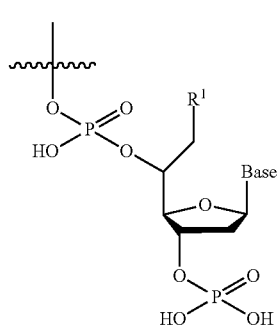

wherein $R^1$ is —$NH_2$, —OH, —NHC(O)$OR^a$ or —$OCH_2OSi(R^b)_3$;

$R^a$ is $C_{1-4}$ alkyl, tert-butyl, allyl, benzyl, or 9-fluorenylmethyl;

each $R^b$ is independently selected from the group consisting of $C_{1-4}$ alkyl and phenyl; and Base is an optionally protected adenine, guanine, cytosine, thymine, or uracil, or a derivative thereof. In some embodiments, the phosphate group may be negatively charged (e.g., $PO_4^-$). In some embodiments, the compound of Formula (V) may be prepared from a compound of Formula (V'):

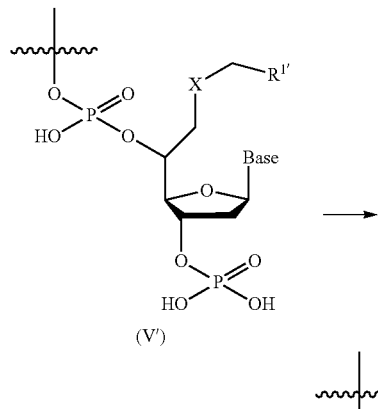

(V')

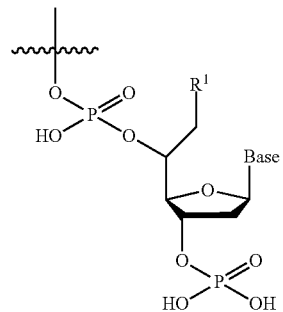

where X is O or NH; $R^{1'}$ is protected OH (i.e., —O-TOM, —O-trityl, —O-DMT, —OTMS, —O-TBDMS, —O-TIPS, —OBz) or protected $NH_2$ (i.e., —NH-Boc, —NH-Fmoc, —NH-CBz, —NH-Alloc); and $R^1$ is $NH_2$ or OH.

In another aspect is an oligonucleotide comprising a 3' phosphate modified nucleotide of Formula (V), where the oligonucleotide is a compound of Formula (VI):

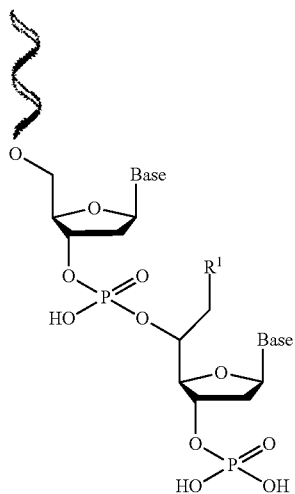

(VI)

wherein $R^1$ is —$NH_2$, —OH, —NHC(O)$OR^a$ or —$OCH_2OSi(R^b)_3$;

$R^a$ is $C_{1-4}$ alkyl, tert-butyl, allyl, benzyl, or 9-fluorenylmethyl;

each $R^b$ is independently selected from the group consisting of $C_{1-4}$ alkyl and phenyl;

each Base is independently an optionally protected adenine, guanine, cytosine, thymine, or uracil, or a derivative thereof. In some embodiments, the oligonucleotide is optionally bound to a solid support. In some embodiments, the phosphate group may be negatively charged (e.g., $PO_4^-$). In some embodiments, the compound of Formula (VI) may be prepared from the compound of Formula (VI'):

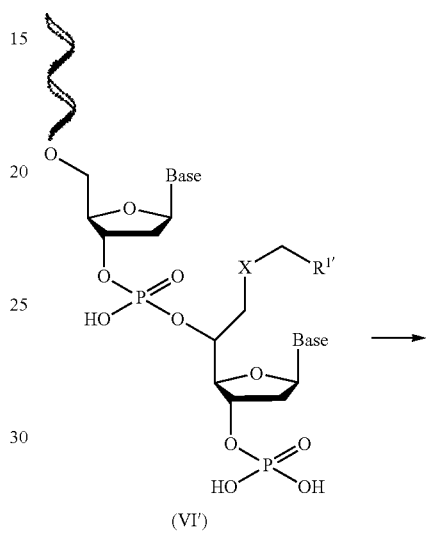

(VI')

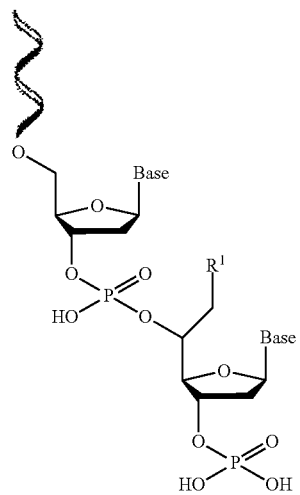

where X is O or NH; $R^{1'}$ is protected OH (i.e., —O-TOM, —O-trityl, —O-DMT, —OTMS, —O-TBDMS, —O-TIPS, —OBz,) or protected $NH_2$ (i.e., —NH-Boc, —NH-Fmoc, —NH-CBz, —NH-Alloc); and $R^1$ is $NH_2$ or OH.

In some aspects of Formula (V) or (VI), $R^1$ is —NHC(O)$OR^a$. In some aspects, $R^a$ is 9-fluorenylmethyl, benzyl, or allyl. In some aspects, $R^1$ is —$OCH_2OSi(R^b)_3$. In some aspects, each $R^b$ is isopropyl. In some aspects, each $R^b$ is independently methyl, ethyl, tert-butyl, or phenyl.

The disclosure also relates to a chemical reagent for introducing a 3' phosphate modified nucleotide into a polynucleotide, wherein the chemical reagent is a compound of Formula (VII):

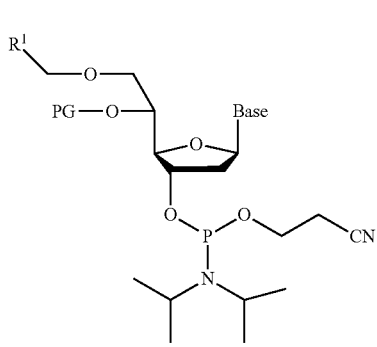

(VII)

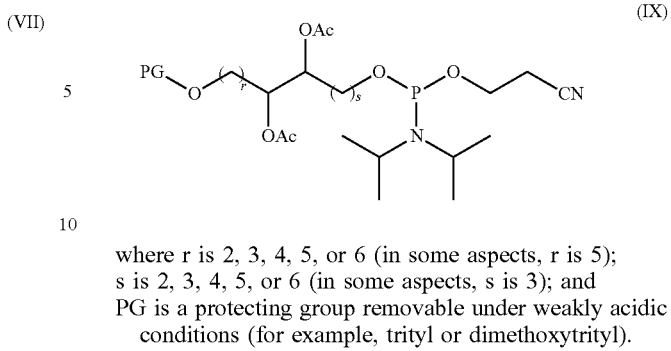

(IX)

where r is 2, 3, 4, 5, or 6 (in some aspects, r is 5);
s is 2, 3, 4, 5, or 6 (in some aspects, s is 3); and
PG is a protecting group removable under weakly acidic conditions (for example, trityl or dimethoxytrityl).

wherein $R^1$ is as defined above; PG is H or a hydroxyl protecting group; and Base is an optionally protected adenine, guanine, cytosine, thymine, or uracil, or a derivative thereof.

In some aspects of Formula (VII), $R^1$ is —NHC(O)OR$^a$. In some aspects, $R^a$ is 9-fluorenylmethyl, benzyl, or allyl. In some aspects, $R^1$ is —OCH$_2$OSi(R$^b$)$_3$. In some aspects, each $R^b$ is isopropyl. In some aspects, each $R^b$ is independently methyl, ethyl, tert-butyl, or phenyl.

The disclosure also relates to methods of making diol linkers for incorporation into polynucleotides. In some aspects, the diol linker is a diol linker as described in U.S. Pat. No. 8,715,966. In some aspects, the diol linker has a structure of Formula (VIII):

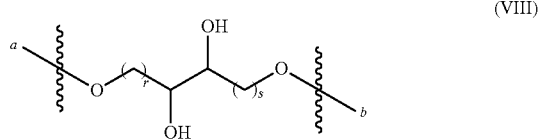

(VIII)

where r is 2, 3, 4, 5, or 6;
s is 2, 3, 4, 5, or 6;
the "a" oxygen is the 3' hydroxyl oxygen of a first nucleotide; and
the "b" oxygen is the 5' hydroxyl oxygen of a second nucleotide.

In some aspects, the diol linker has the structure of Formula (VIIIa):

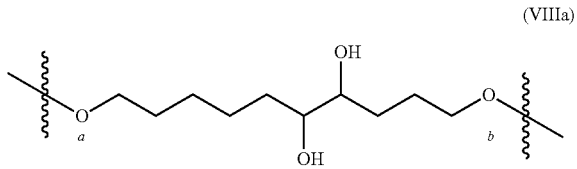 [SMILES: *OCCCCCC(O)C(O)CCCO*]

(VIIIa)

where "a" and "b" are as defined above.

The disclosure relates to methods of making a chemical reagent for incorporation of a linker of Formula (VIII) or (VIIIa) into a polynucleotide, where the chemical reagent is a compound of Formula (IX):

DETAILED DESCRIPTION OF THE EMBODIMENTS

Non-enzymatic chemical linearization strategies are an attractive alternative for cleaving the bridged double-stranded polynucleotide structures ahead of each sequencing read. In particular, chemicals can often be stored for prolonged periods at room temperature and are relative inexpensive compared to enzymes. The present application relates to methods of chemical linearization of clusters of double-stranded polynucleotides immobilized on a solid support for generating a template for sequencing. Each double-stranded polynucleotide comprises a first strand and a second strand. The first strand is generated by extending a first extension primer immobilized to the solid support and the second strand is generated by extending a second extension primer immobilized to the solid support. Each of the first and the second strand comprises a cleavage site. In some embodiments, the first strand comprises a cleavage site that is capable being cleaved by a palladium complex or a nickel complex, for example, a Pd(0) complex or a Ni(0) complex. In a particular embodiment, the cleavage site is located in the first extension primer portion of the first strand. In a further embodiment, the cleavage site comprises a thymine nucleoside or nucleotide analogue having an allyl functionality. In some embodiments, the second strand comprises a cleavage site that include an azobenzene linker that is capable of being cleaved by a chemical reagent, for example, $Na_2S_2O_4$. Alternatively, the second strand comprises a cleavage site that include a diol linker that is capable of being cleaved by a periodate, for example, $NaIO_4$. The methods described herein may be used as part of a sequencing by synthesis (SBS) reaction on a system such as the HiSeq®, MiSeq® or NextSeq® systems from Illumina (San Diego, CA).

Figure 1:
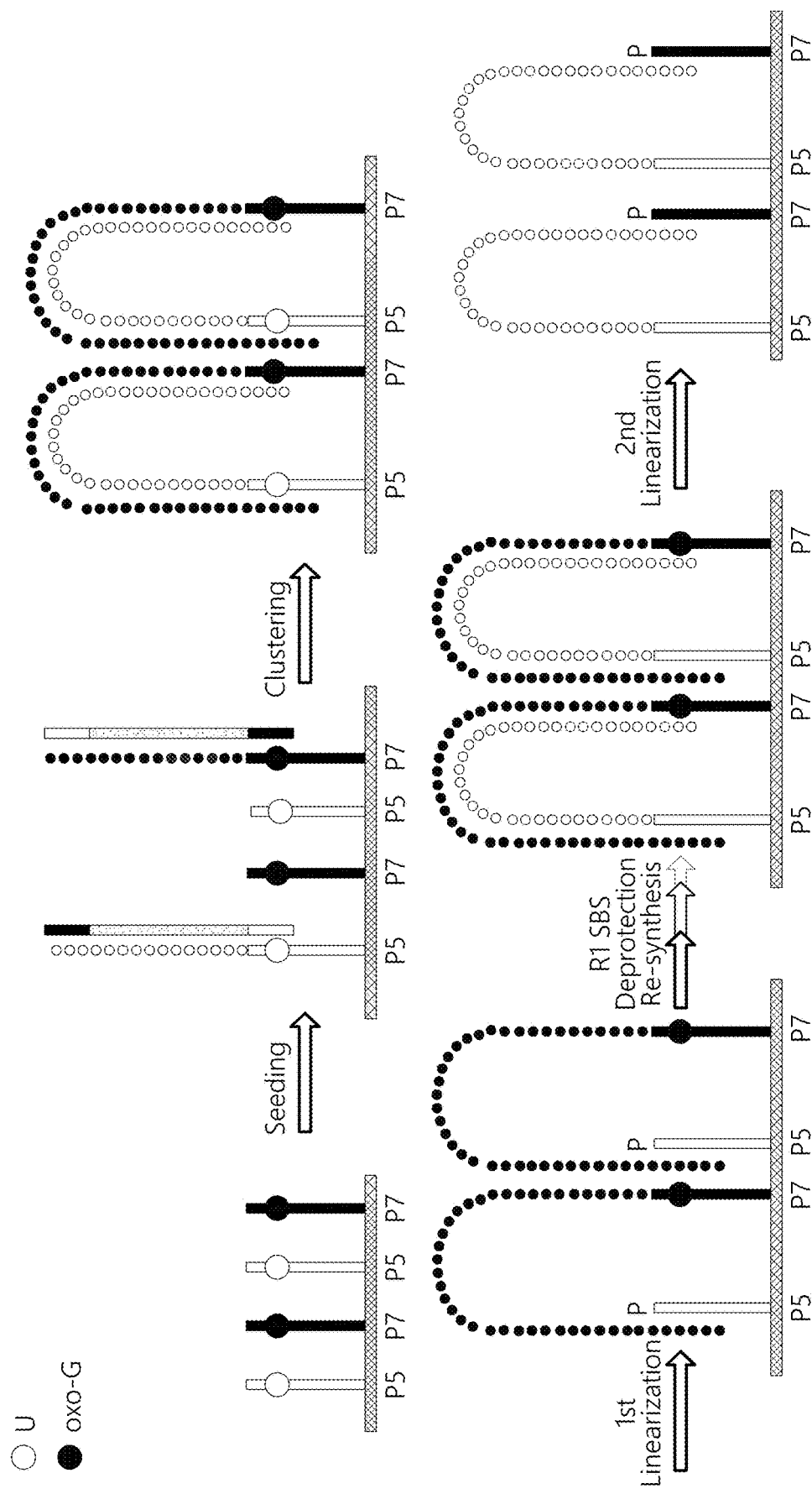
FIG. 1 illustrates an embodiment of a workflow of the Illumina's Sequencing-by-Synthesis (SBS) chemistry.

FIG. 1 describes an embodiment of a standard workflow of the Illumina SBS chemistry. First, a solid support comprising a plurality of P5/P7 primers immobilized on the surface of the solid support is provided. Each of the P5 and the P7 primers has a cleavage site within the sequence. In one embodiment, the cleavage site on the P5 primer is a deoxyuridine (U). In one embodiment, the cleavage site on the P7 primer is an 8-oxo-guanine nucleotide (oxo-G). A set of target DNA molecules to be sequenced is hybridized to the immobilized P5/P7 primers. After hybridization, the original target DNA molecules are removed, leaving only the complementary copies of the extended polynucleotides containing the P5/P7 primers. This step is also known as a "seeding" step. Then, the extended P5/P7 polynucleotides are amplified through a process called the "bridge amplification," forming double-stranded clusters with both strands being attached to the solid support at the 5' end. After the "clustering" step, the first linearization is performed to remove a portion of the extended polynucleotides containing the P5 primer. In one embodiment, such removal is facilitated by an enzymatic cleavage reaction using an enzyme USER to cleave the U position on the P5 primer. After a first round of SBS (Read 1), a re-synthesis is carried out to form the double-stranded polynucleotides again. Then, a second linearization is performed to remove a portion of the extended polynucleotides containing the P7 primer. In one embodiment, such removal is facilitated by an enzymatic cleavage reaction using enzyme FPG to cleave the oxo-G position of the P7 primer. Then a second round of SBS is carried out (Read 2) to sequence the target DNA.

The P5 and P7 primers are used on the surface of commercial flow cells sold by Illumina, Inc. for sequencing on the HiSeq®, MiSeq®, NextSeq® and Genome Analyzer® platforms. The primer sequences are described in U.S. Patent Publication No. 2011/0059865 A1, which is incorporated herein by reference in its entirety.

The standard P5 and P7 primer sequences for the paired-end sequencing comprise the following:

```
P5: paired end 5'→3'
                                        (SEQ ID NO. 1)
AATGATACGGCGACCACCGAGAUCTACAC P7: paired end 5'→3'
                                        (SEQ ID NO. 2)
CAAGCAGAAGACGGCATACGAG*AT
``` where G* is 8-oxo-guanine.

Optionally, one or both of the P5 and P7 primers can include a poly T tail. The poly T tail is generally located at the 5' end of the above sequences, but in some cases can be located at the 3' end. The poly T sequence can include any number of T nucleotides, for example, from 2 to 20.

The standard P5 and P7 primer sequences used on a PAZAM coated flow cell with a poly-T spacer comprise the following:

```
P5 primer with poly-T spacer:
                                        (SEQ ID NO. 3)
5'-alkyne-TTTTTTTTTTAATGATACGGCGACCACCGAGAUCTACAC P7 primer with poly-T spacer:
                                        (SEQ ID NO: 4)
51-alkyne-TTTTTTTTTCAAGCAGAAGACGGCATACGAG*AT
``` where G* is 8-oxo-guanine.

Additional primer sequences include a set of P5 and P7 primers for single read SBS:

```
P5: single read: 5'→3'
                                        (SEQ ID NO. 7)
AATGATACGGCGACCACCGA P7: single read 5'→3'
                                        (SEQ ID NO. 8)
CAAGCAGAAGACGGCATACGA
```

As used herein, when the standard P5/P7 primers or oligos are modified to incorporate a first or second cleavage site that is capable of undergoing chemical cleavage, for example, by a Pd complex or a Ni complex, the modification of the P5/P7 primers may refer to the replacement or substitution of an existing nucleotide (or nucleoside) in the P5/P7 sequence with a different chemical entity, for example, a modified nucleotide or nucleoside analogue with specific functionality to enable site-specific chemical cleavage. The modification may also refer to the insertion of a new chemical entity into the existing P5/P7 sequence, where the new chemical entity is capable of undergoing site specific chemical cleavage. In some embodiments, the modified P5/P7 primers are referred to as P15/P17 primers respectively, comprises the following:

```
P15 primer 5'→3'
                                        (SEQ ID NO. 5)
5'-Alkyne-TTTTTTAATGATACGGCGACCACCGAGAXCTACAC
``` where X=allyl T nucleoside as shown in Scheme 1.

```
P17 primer 5'→3'
                                        (SEQ ID NO. 6)
5'-Alkyne-TTTTTTYYYCAAGCAGAAGACGGCATACGAGAT
``` where Y is a diol linker subject to chemical cleavage, for example, by oxidation with a reagent such as periodate, as disclosed in U.S. Publication No. 2012/0309634, which is incorporated by preference in its entirety. In some embodiments, the diol linker comprises a Formula (VIII) or (VIIIa) as described herein.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:
  Ac Acetyl
  Ac20 Acetic anhydride
  Alloc Allyloxycarbonyl
  aq. Aqueous
  BOC or Boc tert-Butoxycarbonyl
  Bz Benzyl
  ° C. Temperature in degrees Centigrade
  Cbz Benzyloxycarbonyl
  CVD Chemical Vapor Deposition
  dATP Deoxyadenosine triphosphate
  dCTP Deoxycytidine triphosphate
  dGTP Deoxyguanosine triphosphate
  dTTP Deoxythymidine triphosphate
  ddNTP(s) Dideoxynucleotide(s)
  DCM Methylene chloride
  DMF Dimethylformamide
  DMT or DMTr Dimethoxytrityl
  EtOAc Ethyl acetate
  FC Flow cell
  Fmoc Fluorenylmethyloxycarbonyl
  g Gram(s)
  h or hr Hour(s)
  IPA Isopropyl alcohol
  LCMS Liquid chromatography-mass spectrometry
  mL Milliliter(s)
  Ni Nickel
  PE Petroleum ether
  PAZAM poly(N-(5-azidoacetamidylpentyl) acrylamide-co-acrylamide) of any acrylamide to Azapa ratio
  Pd Palladium
  rt Room temperature
  SBS Sequencing by Synthesis
  TBAF Tetra-n-butylammonium fluoride
  TBDMS Tributyldimethylsilyl
  TEA Triethylamine
  TFA Trifluoroacetic acid
  Tert, t tertiary
  THF Tetrahydrofuran
  THM Tris(hydroxymethyl)phosphine
  THP Tris(hydroxypropyl)phosphine
  TIPS Triisopropylsilyl
  TLC Thin Layer Chromatography
  TMS Trimethylsilyl
  TOM Triisopropylsilyloxymethyl
  Trityl Triphenylmethyl
  μL Microliter(s)

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction.

As used herein, the term "extension primer" refers to an oligonucleotide or polynucleotide immobilized on a solid support, where the oligonucleotide or polynucleotide is capable of specifically binding to a sequence of a target single strand nucleic acid molecule. After a hybridization process, the oligonucleotide or polynucleotide is extended to comprise sequence that is complimentary to the target nucleic acid molecule. In some instances, the term "extension primer" is used interchangeably with "amplification primer."

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g., found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

As used herein, the term "polynucleotide" refers to nucleic acids in general, including DNA (e.g., genomic DNA cDNA), RNA (e.g., mRNA), synthetic oligonucleotides and synthetic nucleic acid analogs. Polynucleotides may include natural or non-natural bases, or combinations thereof and natural or non-natural backbone linkages, e.g., phosphorothioates, PNA or 2'-O-methyl-RNA, or combinations thereof. In some instances, the term "polynucleotide," "oligonucleotide," or "oligo" are used interchangeably.

The term "cleavage site" as used herein refers to a position on the polynucleotide sequence where a portion of the polynucleotide may be removed by a cleavage reaction. The position of the cleavage site is preferably pre-determined, meaning the location where the cleavage reaction happens is determined in advance, as opposed to cleavage at a random site where there location of which is not known in advance.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (e.g., acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. Particularly useful solid supports for some embodiments are components of a flow cell or located within a flow cell apparatus. The solid support may have a planar surface, for example, a flow cell, or a non-planar surface, for example, a bead.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

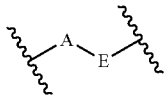

includes the substituent being oriented such that the A is attached at the leftmost attachment point of the molecule as well as the case in which A is attached at the rightmost attachment point of the molecule.

Methods of Palladium (Pd) or Nickel (Ni) Assisted First Chemical Linearization

Some embodiments of the present disclosure relate to methods of linearizing a plurality of immobilized double-stranded polynucleotides, comprising: providing a solid support comprising double-stranded polynucleotides, wherein each double-stranded polynucleotide comprises a first strand and a second strand, wherein the first strand and the second strand are each immobilized to the solid support at their 5' ends, and wherein each first strand comprises a first cleavage site capable of undergoing chemical cleavage in the presence of a cleavage reagent; contacting the double-stranded polynucleotides with the cleavage reagent, thereby cleaving one or more first strands at the first cleavage site, and generating one or more cleaved first nucleic acids and cleaved immobilized first strands; and removing the cleaved first nucleic acids from the solid support. In some aspects, the cleavage site is capable of undergoing cleavage in the presence of a Pd complex or a Ni complex. In some aspects, the cleavage reagent is an aqueous solution of the Pd complex or the Ni complex. In some aspects, the cleavage reagent is prepared in situ.

In some embodiments of the Pd/Ni linearization methods described herein, each first strand is extended from a first extension primer immobilized to the solid support. In some such embodiments, the first extension primer comprises a nucleotide sequence that is a P5 or P7 sequence as disclosed herein, or a sequence that is complementary to P5 or P7. In one embodiment, the first extension primer comprises a P5 nucleotide sequence (SEQ ID NO: 1). In a further embodiment, the first extension primer comprises a poly-T spacer P5 nucleotide sequence (SEQ ID NO: 3). In one embodiment, the first extension primer is a P5 primer. In a further embodiment, the first extension primer is a poly-T spacer P5 primer. In further embodiments, the first extension primer comprises a nucleotide sequence that is a P5 or P7 sequence as disclosed herein, or a sequence that is complementary to P5 or P7, wherein one nucleotide of the sequence is replaced by a modified nucleotide that is susceptible to cleavage in the presence of a palladium complex. In some aspects, the first extension primer comprises a nucleotide sequence of P15 as described herein (SEQ ID NO:5).

In some embodiments of the Pd/Ni linearization methods described herein, the first extension primer comprises the first cleavage site. In some further embodiments, the first cleavage site comprises a modified nucleotide or nucleoside that is capable of undergoing chemical cleavage, for example by the palladium complex. In some embodiments, the modified nucleoside or nucleotide has the structure of Formula (II):

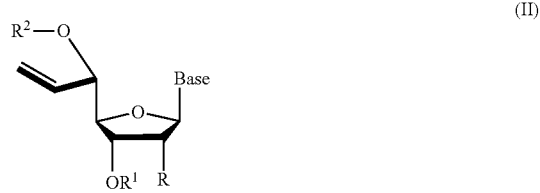

wherein R is H, OH or OPG; $R^1$ is H or PG; $R^2$ is H, PG, or —$OR^2$ is a phosphate group; PG is a hydroxyl protecting group; Base is adenine, guanine, cytosine, thymine, or uracil, or a derivative thereof. In some embodiments, the phosphate group may be negatively charged (e.g., —$PO_4^-$). In one aspect, the modified nucleoside or nucleotide has the structure of Formula (IIa):

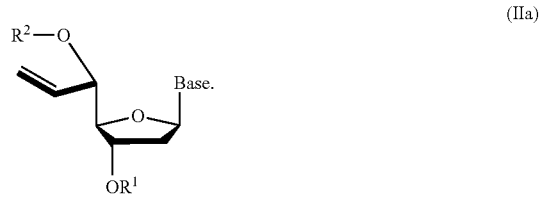

In some embodiments, the first cleavage site incorporating the modified nucleoside or nucleotide moiety comprises the structure of Formula (II'), where the 3' oxygen of the allyl modified nucleoside or nucleotide is covalently attached to the 5' end of another nucleotide (structure not shown):

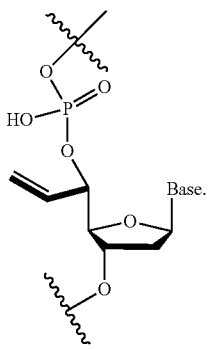
(II')

In some embodiments, the phosphate group may be negatively charged (e.g., —PO$_4^-$).

In some further embodiments, the modified nucleotide or nucleoside may further be labeled with a detectable label, for example, a fluorescent label. In some embodiments, the modified nucleotide comprises a vinyl substituent at the 5' carbon of the nucleotide or nucleoside, thus forming an allyl moiety with respect to the 5' hydroxyl group. In some embodiments, the 5' hydroxyl group connects to a 3' phosphate of a second nucleotide, such that the dinucleotide unit comprises a cleavage site with an allyl phosphate moiety. In some embodiments, the modified nucleotide or nucleoside is a thymine (T) nucleoside or nucleotide analogue. In some further embodiments, the 3' hydroxyl protecting (or blocking) group, for example, a phosphate moiety (as shown in Formula (II')), remains on the cleaved immobilized first strands after chemical cleavage of the first strands. In one such embodiment, the 3' phosphate moiety of the second nucleotide is covalently attached to the 5'-carbon position of the modified nucleoside analogue (i.e., the phosphate group includes the 5' hydroxyl of the modified nucleotide). In some embodiments, the cleavage site is located near the 3' end of the first extension primer, for example, within 1, 2, 3, 4, 5, 6, 7, 8, 9, or 10 nucleotide distance from the 3' end of the first extension primer. In some other embodiments, the cleavage site is located near the 5' end of the first extension primer, for example, within 1, 2, 3, 4, 5, 6, 7, 8, 9, or 10 nucleotide distance from the 5' end of the first extension primer. In some cases, to ensure efficient DNA resynthesis, the cleavage site is preferably located towards the 3' end of the first primer, for example, within 2 to 8, or 3 to 7, or 4 to 6 nucleotide distance. In one embodiment, the first extension primer is a P5 primer and the first cleavage site is located in the P5 primer sequence (e.g., the modified nucleotide is incorporated into the P5 primer sequence, by adding to or replacing one nucleotide). Therefore, the P5 sequence disclosed herein (SEQ ID NO: 1 or SEQ ID NO: 3) is modified to include the first cleavage site that is capable of undergoing chemical cleavage by the Pd/Ni complex, thus forming a modified P5 primer. In one embodiment, the modified P5 primer comprises or is a P15 primer disclosed herein (SEQ ID NO: 5).

Palladium Reagents

In some embodiments of the Pd linearization methods described herein, the Pd complex used in the chemical linearization method is water soluble. In some such embodiments, the Pd complex is a Pd(0) complex. In some instances, the Pd(0) complex may be generated in situ from reduction of a Pd(II) complex by reagents such as alkenes, alcohols, amines, phosphines, or metal hydrides. Suitable palladium sources include Na$_2$PdCl$_4$, (PdCl(C$_3$H$_5$))$_2$, [Pd(C$_3$H$_5$)(THP)]Cl, [Pd(C$_3$H$_5$)(THP)$_2$]Cl, Pd(OAc)$_2$, Pd(Ph$_3$)$_4$, Pd(dba)$_2$, and Pd(TFA)$_2$. In one such embodiment, the Pd(0) complex is generated in situ from Na$_2$PdCl$_4$. In another embodiment, the palladium source is allyl palladium (II) chloride dimer [(PdCl(C$_3$H$_5$))$_2$]. In some embodiments, the Pd(0) complex is generated in an aqueous solution by mixing a Pd(II) complex with a phosphine. Suitable phosphines include water soluble phosphines, such as tris(hydroxypropyl)phosphine (THP), tris(hydroxymethyl)phosphine (THM), 1,3,5-triaza-7-phosphaadamantane (PTA), bis(p-sulfonatophenyl)phenylphosphine dihydrate potassium salt, tris(carboxyethyl)phosphine (TCEP), and triphenylphosphine-3,3',3''-trisulfonic acid trisodium salt.

In some embodiments, the Pd(0) is prepared by mixing a Pd(II) complex [(PdCl(C$_3$H$_5$))$_2$] with THP in situ. The molar ratio of the Pd(II) complex and the THP may be about 1:2, 1:3, 1:4, 1:5, 1:6, 1:7, 1:8, 1:9, or 1:10. In some further embodiments, one or more reducing agents may be added, such as ascorbic acid or a salt thereof (e.g., sodium ascorbate).

In some embodiments, the Pd(0) is prepared by mixing a Pd(II) pre-catalyst such as [Pd(C$_3$H$_5$)(THP)]Cl, [Pd(C$_3$H$_5$)(THP)$_2$]Cl with additional THP. [Pd(C$_3$H$_5$)(THP)]Cl and [Pd(C$_3$H$_5$)(THP)$_2$]Cl may be prepared by reacting (PdCl(C$_3$H$_5$))$_2$ with 1 to 5 equivalents of THP and they may be isolated prior to use in the chemical linearization reaction.

In some other embodiments, the Pd(0) complex is Pd(THM)$_4$, Pd(THP)$_2$, Pd(THP)$_3$, or PD(THP)$_4$, or combinations thereof.

Nickel Reagents

In some embodiments of the Ni linearization methods described herein, the Ni complex used in the chemical linearization method is water soluble. In some such embodiments, the Ni complex is a Ni(0) complex. In some instances, the Ni complex may be generated in situ from reduction of a Ni(II) compound by reagents such as alkenes, alcohols, amines, phosphines, or metal hydrides. In some embodiments, the Ni(II) compound is NiCl$_2$. Suitable phosphines include water soluble phosphines, such as tris(hydroxypropyl)phosphine (THP), tris(hydroxymethyl)phosphine (THM), 1,3,5-triaza-7-phosphaadamantane (PTA), bis(p-sulfonatophenyl)phenylphosphine dihydrate potassium salt, tris(carboxyethyl)phosphine (TCEP), and triphenylphosphine-3,3',3''-trisulfonic acid trisodium salt. In one embodiment, the Ni complex is prepared by mixing NiCl$_2$ with 1 to 10 equivalents of THP.

Some embodiments of the present disclosure relate to a method of linearizing a plurality of immobilized double-stranded polynucleotides, comprising: providing a solid support comprising double-stranded polynucleotides, each double-stranded polynucleotide comprises a first strand and a second strand, wherein each first strand is extended from a modified P5 primer immobilized to the solid support, each second strand is extended from a P7 primer immobilized to the solid support, both the first strand and the second strand are immobilized to the solid support at their 5' ends, wherein each modified P5 primer comprises a first cleavage site capable of undergoing chemical cleavage by a Pd(0) complex; contacting the double-stranded polynucleotides with an aqueous solution of the Pd(0) complex, thereby cleaving one or more first strands at the first cleavage site, and generating one or more cleaved first nucleic acids and cleaved immobilized first strands; and removing the cleaved first nucleic acids from the solid support. In some embodiments, the first cleavage site comprises a modified T nucleoside or nucleotide having an allyl functionality. The cleavage site may further include a 3' blocking moiety, for example, a phosphate moiety, which remains on the first strand after the Pd cleavage reaction to block the 3'-OH of the cleaved immobilized first strands. In some embodiment, the 3' blocking moiety comprises a modified nucleoside or nucleotide containing a phosphate group, which can be deprotected by a chemical reaction or by an enzymatic reaction. In one embodiment, the modified P5 primer comprises or is P15.

3'-Deprotection

Some embodiments of the present disclosure relate to a method of removing a 3'end protecting group from an oligonucleotide, comprising: providing a solid support comprising a plurality of oligonucleotides immobilized thereon at their 5' ends, wherein the oligonucleotides each comprises a 3' end protecting group having a structure of Formula (I) as described herein; and contacting the oligonucleotides with a deprotecting reagent, thereby cleaving the 3' end protecting group to produce oligonucleotides each with a free 3' end hydroxyl group. The 3' end modified phosphate moiety having the structure of Formula (I):

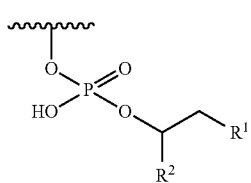

(I)

wherein $R^1$ is —$NH_2$, —OH, —NHC(O)$OR^a$ or —$OCH_2OSi(R^b)_3$; $R^a$ is $C_{1-4}$ alkyl, tert-butyl, allyl, benzyl, or 9-fluorenylmethyl; each $R^b$ is independently selected from the group consisting of $C_{1-4}$alkyl and phenyl; and $R^2$ is H, $C_{1-4}$ alkyl, an optionally substituted tetrahydrofuran, or a nucleotide.

In some further embodiments, the protecting group comprises the structure of Formula (V):

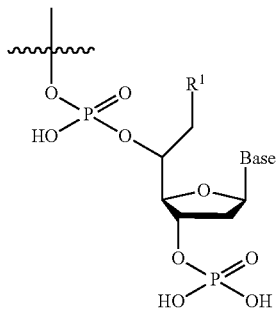

(V)

wherein Base is an optionally protected adenine, guanine, cytosine, thymine, or uracil, or a derivative thereof. In some embodiments, one or more phosphate groups in Formula (I) or (V) may be negatively charged (e.g., $PO_4^-$).

In some embodiments of Formula (I) or (V), $R^1$ is —NHC(O)$OR^a$. In some embodiments, $R^a$ is 9-fluorenylmethyl, benzyl, or allyl. In some embodiments, $R^1$ is —$OCH_2Si(R^b)_3$. In some embodiments, each $R^b$ is isopropyl. In some embodiments, each $R^b$ is independently methyl, ethyl, tert-butyl, or phenyl.

In some embodiments, the modified phosphate group of Formula (I) or (V) may be removed by a chemical deprotecting reagent, such as a fluoride containing reagent or a base. Non-limiting examples include tetra-n-butylammonium fluoride (TBAF), HF, $NH_4F$, CsF, NaOH, and KOH, and combination thereof.

In some embodiments of the Pd/Ni linearization methods described herein, after the first linearization, the remaining portion of the immobilized first strands has a unprotected 3'end hydroxyl group and the methods further include blocking the 3' end of the remaining portion of the cleaved immobilized first strands after the Pd/Ni cleavage reaction. In one such embodiment, the blocking comprises phosphorylating the 3' end of the cleaved immobilized first strands as a 3' hydroxyl protecting group. In some other embodiments, the 3' end of each cleaved immobilized first strands comprises a protecting group. In some such embodiments, the blocking effect may be achieved by a phosphate moiety or modified phosphate moiety remaining on the cleaved immobilized first strands after the cleavage reaction, which serves as a blocking group to the 3'-OH of the cleaved immobilized first strands. In some embodiments, the modified phosphate moiety comprises the structure of Formula (I) or (V) as described herein.

The phosphate group or modified phosphate group is removed before DNA resynthesis to generate derivative first strands that are complementary to the immobilized second strands. In some embodiments, the 3' end protecting group is a phosphate group, which may be removed by a phosphatase such as T4PNK. In some other embodiments, the 3' end protecting group is a modified phosphate group of Formula (I) or (V), which may be removed by a fluoride containing reagent or a base, such as tetra-n-butylammonium fluoride (TBAF), HF, $NH_4F$, CsF, NaOH, or KOH, or combination thereof.

Methods of Second Linearization

In some embodiments of the Pd/Ni linearization methods described herein, each second strand is extended from a second extension primer immobilized to the solid support, and each second strand comprises a second cleavage site. In some such embodiments, the second extension primer comprises a nucleotide sequence selected from the group consisting of a P5 or P7 sequence as disclosed herein, or a sequence that is complementary to P5 or P7. In one embodiment, the second extension primer comprises a P7 nucleotide sequence (SEQ ID NO: 2). In a further embodiment, the second extension primer comprises a poly-T spacer P7 nucleotide sequence (SEQ ID NO: 4). In some aspect, the second extension primer comprises a nucleotide sequence that is P5 or P7, with a modified nucleotide incorporated (added to or replacing a base in the sequence with a base that has a 3' hydroxyl protecting group). In a further embodiment, the second extension primer comprises a P17 primer (SEQ ID NO: 6). In one embodiment, the second extension primer is a P7 primer. In a further embodiment, the second extension primer is a poly-T spacer P7 primer. In another embodiment, the second extension primer is a P17 primer.

In some embodiments of the Pd/Ni linearization methods described herein, the second extension primer comprises the second cleavage site. In some embodiments, the second cleavage site is not capable of undergoing chemical cleavage by the palladium complex or the nickel complex. In some aspect, the second cleavage site may be cleaved by a method selected from the group consisting of chemical cleavage, photo cleavage, enzymatic cleavage, or a combination thereof. In one embodiment, the second cleavage site may be cleaved by an enzymatic cleavage reaction. In one embodiment, the second extension primer is a P7 primer disclosed herein (SEQ ID NO: 2 or SEQ ID NO: 4) and the second cleavage site is oxo-G. In some such embodiment, the enzyme used for the cleavage reaction is FPG.

In some other embodiments, the second cleavage site may be cleaved by a chemical cleavage reaction. In one such embodiment, the second extension primer comprises or is a P7 primer modified to include a modified nucleotide that is susceptible to chemical cleavage according to the modes described herein. In some embodiments, the second extension primer comprises or is a P17 primer disclosed herein (SEQ ID NO: 6) and the second cleavage site comprises one or more diol linkages that can be cleaved by treatment with periodate, for example, sodium periodate. In some such embodiments, the diol linker comprises the structure of Formula (VIII):

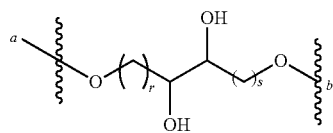

(VIII)

where r is 2, 3, 4, 5, or 6;
s is 2, 3, 4, 5, or 6;
the "a" oxygen is the 3' hydroxyl oxygen of a first nucleotide; and
the "b" oxygen is the 5' hydroxyl oxygen of a second nucleotide.

In some embodiments, the diol linker has the structure of Formula (VIIIa):

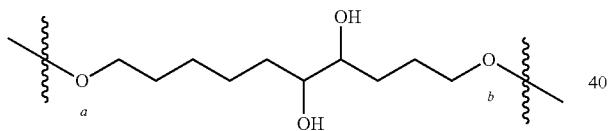

(VIIIa)

where "a" and "b" are as defined above.

In some other embodiments, the second cleavage site comprises an azobenzene linker, which may be cleaved by a chemical cleavage reagent, for example, $Na_2S_2O_4$. In some such embodiments, the azobenzene linker comprises a structure of Formula (X):

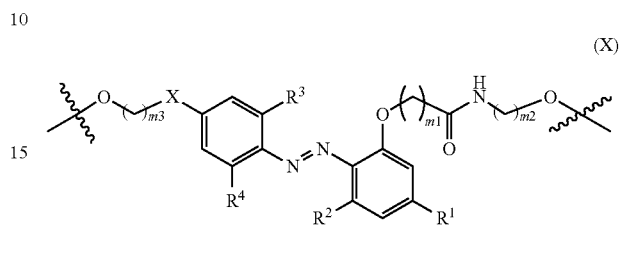

(X)

wherein $R^1$ is H, hydroxyl, or a protected hydroxyl; $R^2$ is H, $C_{1-6}$ alkyl, or $C_{1-6}$ alkoxy; each $R^3$ and $R^4$ is independently H, halo, —C(O)O$R^5$, or —C(O)NH$R^6$; each $R^5$ and $R^6$ is independently H, $C_{1-6}$ alkyl, or $C_{6-10}$ aryl; X is —C(O)—, —CH$_2$—, or —C(O)NH—; and each m1, m2 and m3 is independently 1, 2, 3, 4, 5, or 6. In some aspects, $R^1$ is hydroxyl. In some other aspects, $R^1$ is a protected hydroxyl, such as —OBz. In some aspects, $R^3$ is —C(O)O$R^5$. In some aspects, $R^3$ is —C(O)NH$R^6$. In some such aspects, $R^5$ and $R^6$ are independently $C_{1-6}$ alkyl, such as methyl, ethyl, isopropyl, or t-butyl. In some other aspects, $R^3$ is H. In some aspects, $R^2$ is H. In some aspects, $R^4$ is H. In some aspects, X is —CH$_2$—. In some other aspects, X is —C(O)NH—. In some aspects, m1 is 2, 3 or 4. In some aspects, m2 is 1, 2 or 3. In some aspects, m3 is 1, 2 or 3.

In some embodiments of the azobenzene linker of Formula (X), one end oxygen atom is further connected to a phosphate group, for example, with a structure of Formula (Xa) or Formula (Xb):

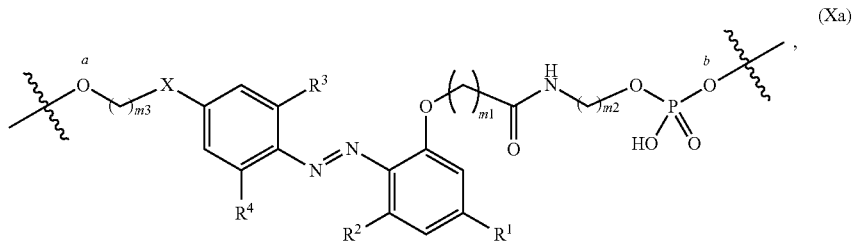

(Xa)

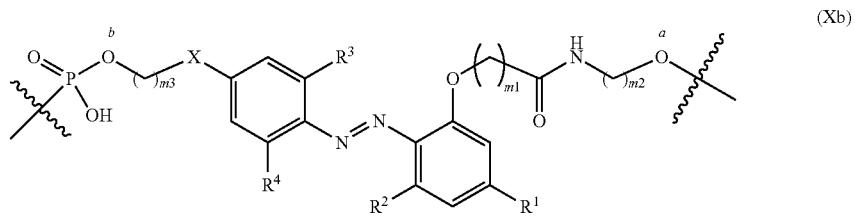

(Xb)

In some aspects, the "a" oxygen is the 3' hydroxyl oxygen of a first nucleotide. In some aspects, the "b" oxygen is the 5' hydroxyl oxygen of a second nucleotide. In some other aspects, the "b" oxygen is the 3' hydroxyl oxygen of a first nucleotide. In some other aspects, the "a" oxygen is the 5' hydroxyl oxygen of a second nucleotide.

The azobenzene linker of Formula (Xa) or (Xb) may be incorporated into an oligonucleotide or polynucleotide by a chemical reagent, where the chemical reagent is a phosphoramidite compound of Formula (XIa) or (XIb):

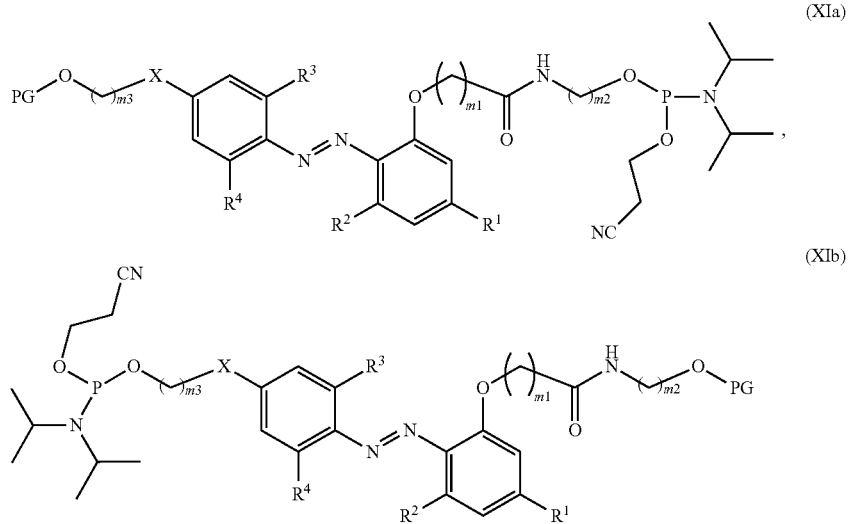

where $R^1$-$R^4$, X, m1, m2, and m3 are defined in (X); and PG is a protecting group removable under weakly acidic conditions (for example, trityl or dimethoxytrityl).

Some additional embodiments of the present disclosure relate to a method of linearizing a plurality of immobilized double-stranded polynucleotides, comprising: providing a solid support comprising double-stranded polynucleotides, each double-stranded polynucleotide comprises a first strand and a second strand, wherein the first strand and the second strand are immobilized to the solid support at their 5' ends, wherein each first strand comprises a first cleavage site, and wherein each second strand comprises a second cleavage site comprising an azobenzene linker; cleaving one or more first strands at the first cleavage site, and generating one or more cleaved first nucleic acids and cleaved immobilized first strands; removing the cleaved first nucleic acids from the solid support; sequencing the immobilized second strands; resynthesizing derivative first strands that are complementary to the second strands; and cleaving one or more second strands at the second cleavage site, and generating one or more cleaved second nucleic acids and cleaved immobilized second strands. In some embodiments of such methods, each first strand is extended from a first extension primer immobilized to the solid support, and wherein the first extension primer comprises the first cleavage site. In some embodiments of such methods, the first cleavage site may be cleaved by a method selected from the group consisting of chemical cleavage, photo cleavage, enzymatic cleavage, and a combination thereof, for example, the first cleavage site may be cleaved by the Pd/Ni methods described herein, or an enzymatic method (e.g., UDG). In some such embodiments, the first extension primer comprises P5, modified P5 or P15. In some embodiments, each second strand is extended from a second extension primer immobilized to the solid support, and wherein the second extension primer comprises the second cleavage site. In some such embodiments, the azobenzene linker comprises the structure of Formula (X), (Xa) or (Xb) as described herein. In some embodiments, the azobenzene linker is cleaved by $Na_2S_2O_4$. In some embodiments, the sequencing of the immobilized second strands comprises successively incorporating labeled nucleotides complementary to the immobilized second strands and detecting the labeled nucleotides. In some embodiments, 3' end of each cleaved immobilized first strands comprises a protecting group, for example, a phosphate group or a modified phosphate moiety comprising the structure of Formula (I) or (V) as described herein. The protecting group may be removed either by an enzymatic reaction (e.g., enzyme T4PNK) or a chemical deprotection, for example, a fluoride containing reagent or a base as described herein for the deprotection of the modified phosphate moiety comprising the structure of Formula (I) or (V). In some embodiments, the method further comprise removing the cleaved second nucleic acids from the solid support, and sequencing the derivative first strands. In some embodiments, the immobilized derivative first strands remain on the solid support following removal of the cleaved second nucleic acids from the solid support, and remain hybridized to the cleaved immobilized second strands.

In some embodiments of the first and the second linearization methods described herein, the double-stranded polynucleotides are immobilized to the solid support through covalent bonding. In one embodiment, the double-stranded polynucleotides are covalently bonded to a hydrogel or polymer coating on the solid support. In one embodiment, the hydrogel or polymer coating comprises PAZAM. In some embodiments, the hydrogel or polymer coating is also covalently attached to the surface of the solid support, for example, through reaction with a functionalized silane deposited on the surface. In one embodiment, the functionalized silane is a norbornene derived silane. Non-limiting examples of hydrogel or polymer coatings on silanized solid support, and methods of grafting polynucleotides or primers to hydrogel or polymer coated solid support are disclosed in U.S. Publication Nos. 2014/0079923 and 2015/0005447, which are incorporated by references in their entireties.

Grafted Solid Support for Pd Linearization

Some embodiments of the present disclosure relate to a solid support comprising a plurality of first strand polynucleotides immobilized thereon, each first strand polynucleotide comprises a first cleavage site capable of undergoing chemical cleavage (e.g., by a palladium complex or a nickel complex as described herein), wherein the plurality of first strand polynucleotides are immobilized to the solid support at their 5' ends.

In some embodiments of the solid support described herein, each first strand comprises or is extended from a first extension primer immobilized to the solid support. In some such embodiments, the first extension primer comprises a nucleotide sequence selected from the group consisting of a P5 or P7 sequence as disclosed herein, or a sequence that is complementary to P5 or P7. In one embodiment, the first extension primer comprises a P5 nucleotide sequence (SEQ ID NO: 1). In a further embodiment, the first extension primer comprises a poly-T spacer P5 nucleotide sequence (SEQ ID NO: 3). In one embodiment, the first extension primer is a P5 primer. In a further embodiment, the first extension primer is a poly-T spacer P5 primer. In some embodiments, the P5 or P7 sequence is modified to include a modified nucleoside or nucleotide that forms at least part of the cleavage site.

In some embodiments of the solid support described herein, the first extension primer comprises the first cleavage site. In some further embodiments, the first cleavage site comprises a modified nucleotide or nucleoside that is capable of undergoing chemical cleavage, for example by the palladium complex or the nickel complex. In some such embodiments, the modified nucleotide or nucleoside is a T nucleoside or nucleotide analogue. In one such embodiment, the cleavage site comprises a T nucleoside analogue comprising an allyl functionality, for example, a vinyl substitution at the 5'-carbon position of the T nucleoside analogue, thus forming an allyl moiety with respect to the 5' hydroxyl group. In some such embodiments, the modified nucleoside or nucleotide comprises the structure of Formula (II) as described herein. In some embodiments, the 5' hydroxyl group connects to a 3' phosphate of a second nucleotide, such that the dinucleotide unit comprises a cleavage site with an allyl phosphate moiety. In some such embodiments, the modified nucleoside or nucleotide comprises the structure of Formula (II') as described herein. In some embodiments, the first extension primer comprises or is P15 primer. In some further embodiments, the cleavage site also comprises a 3' protecting (or blocking) moiety, for example, a phosphate moiety, on the second nucleotide. The blocking moiety remains on the cleaved immobilized first strands after chemical cleavage of the first strands. In one embodiment, the 3' phosphate moiety of the second nucleotide is covalently attached to the 5'-carbon position of the modified nucleoside analogue (i.e., the phosphate group includes the 5' hydroxyl of the modified nucleotide). In some embodiments, the blocking group remaining on the cleaved immobilized first strands comprises the structure of Formula (I) of (V) as described herein, which may be removed in a chemical deprotection reagent, such as a fluoride containing compound or a base. In some embodiments, the blocking group remaining on the cleaved immobilized first strands is a phosphate group, which may be removed by a phosphatase (e.g., T4PNK). In some embodiments, the cleavage site is located near the 3' end of the first extension primer, for example, within 1, 2, 3, 4, 5, 6, 7, 8, 9, or 10 nucleotide distance from the 3' end of the first extension primer. In some other embodiments, the cleavage site is located near the 5' end of the first extension primer, for example, within 1, 2, 3, 4, 5, 6, 7, 8, 9, or 10 nucleotide distance from the 5' end of the first extension primer. In some cases, to ensure efficient DNA resynthesis, the cleavage site is preferably located towards the 3' end of the first primer, for example, within 2 to 8, or 3 to 7, or 4 to 6 nucleotide distance. In one embodiment, the first extension primer is a P5 primer and the first cleavage site is located in the P5 primer sequence (e.g., the modified nucleotide is incorporated into the P5 primer sequence, by adding to or replacing one nucleotide). Therefore, the P5 sequence disclosed herein (SEQ ID NO: 1 or SEQ ID NO: 3) is modified to include the first cleavage site that is capable of undergoing chemical cleavage by the Pd/Ni complex, thus forming a modified P5 primer. In one embodiment, the modified P5 primer comprises or is a P15 primer disclosed herein (SEQ ID NO: 5). In some further embodiments, the modified nucleotide or nucleoside may further be labeled with a detectable label, for example, a fluorescent label. The detectable label enables direct quantification of the grafting reaction immediately after completion.

In some embodiments of the solid support described herein, the Pd complex used in the chemical linearization method is water soluble. In some such embodiments, the Pd complex is a Pd(0) complex. In some instances, the Pd(0) complex may be generated in situ from reduction of a Pd(II) complex by reagents such as alkenes, alcohols, amines, phosphines, or metal hydrides. Suitable palladium sources include $Na_2PdCl_4$, $(PdCl(C_3H_5))_2$, $[Pd(C_3H_5)(THP)]Cl$, $[Pd(C_3H_5)(THP)_2]Cl$, $Pd(Ph_3)_4$, $Pd(OAc)_2$, $Pd(dba)_2$, and $Pd(TFA)_2$. In one such embodiment, the Pd(0) complex is generated in situ from $Na_2PdCl_4$. In another embodiment, the palladium source is allyl palladium(II) chloride dimer $[(PdCl(C_3H_5))_2]$. In some embodiments, the Pd(0) complex is generated in an aqueous solution by mixing a Pd(II) complex with a phosphine. Suitable phosphines include water soluble phosphines, such as tris(hydroxypropyl)phosphine (THP), tris(hydroxymethyl)phosphine (THM), 1,3,5-triaza-7-phosphaadamantane (PTA), bis(p-sulfonatophenyl)phenylphosphine dihydrate potassium salt, tris(carboxyethyl)phosphine (TCEP), and triphenylphosphine-3,3',3"-trisulfonic acid trisodium salt. In some embodiments, Pd(0) may be generated by mixing $[(PdCl(C_3H_5))_2]$, $[Pd(C_3H_5)(THP)]Cl$, or $[Pd(C_3H_5)(THP)_2]Cl$ with THP in situ. One or more reducing agents may be added, such as ascorbic acid or a salt thereof (e.g., sodium ascorbate). In some embodiments, the Pd(0) complex is $Pd(THM)_4$, $Pd(THP)_2$, $Pd(THP)_3$, or $PD(THP)_4$, or combinations thereof.

In some embodiments of the solid support described herein, the Ni complex used in the chemical linearization is water soluble. In some such embodiments, the Ni complex is a Ni(0) complex. In some instances, the Ni complex may be generated in situ from reduction of a Ni(II) compound (such as $NiCl_2$) by reagents similar to those used in the reduction of Pd(II) to Pd(0) as described herein. In one embodiment, the Ni complex is prepared by mixing $NiCl_2$ with 1 to 10 equivalents of THP.

In some embodiments of the solid support described herein, the solid support further comprises a plurality of a second strand polynucleotides immobilized thereon, each second strand polynucleotide comprises a second cleavage site, wherein the plurality of second strand polynucleotides are immobilized to the solid support at their 5' ends. In some such embodiments, each second strand polynucleotide comprises or is extended from a second extension primer immobilized to the solid support. In some such embodiments, the second extension primer comprises a nucleotide sequence selected from the group consisting of a P5 or P7 sequence as disclosed herein, or a sequence that is complementary to P5 or P7. In one embodiment, the second extension primer comprises a P7 nucleotide sequence (SEQ ID NO: 2). In a further embodiment, the second extension primer comprises a poly-T spacer P7 nucleotide sequence (SEQ ID NO: 4). In another embodiment, the second extension primer comprises a P15 sequence (SEQ ID NO: 6). In one embodiment, the second extension primer is a P7 primer. In a further embodiment, the second extension primer is a poly-T spacer P7 primer. In some embodiments, the P7 primer or poly-T spacer P7 primer is modified to remove the 8-oxo-guanine and insert a chemically cleavable linker, e.g., one or more diol units. In yet another embodiment, the second extension primer is a P17 primer. In some embodiments, the second extension primer comprises the second cleavage site. In some such embodiments, the P5, P7, or P17 sequences are modified to include a modified nucleotide with a cleavable linker. In some further embodiments, the second cleavage site is not capable of undergoing chemical cleavage by the palladium complex or the nickel complex used in the first chemical linearization reaction. The second cleavage site may be cleaved by a method selected from the group consisting of chemical cleavage, photochemical cleavage, enzymatic cleavage, or a combination thereof. In one embodiment, the second cleavage site may be cleaved by an enzymatic cleavage reaction. In one such embodiment, the second extension primer is a P7 primer disclosed herein (SEQ ID NO: 2 or SEQ ID NO: 4) and the second cleavage site is oxo-G. In another embodiment, the second cleavage site may be cleaved by a chemical cleavage reaction. For example, the second cleavage site may include one or more vicinal diol linkages (that can be cleaved by oxidation, such as treatment with a periodate reagent), disulfide linkages (cleavable, for example, under reducing conditions such as DTT, or in the presence of a phosphine), ortho-nitrobenzyl groups (cleavable, for example, by photolysis), azobenzene linkages (cleavable, for example, in the presence of $Na_2S_2O_4$), alkyl-selenium linkages (cleavable, for example, by oxidation such as hydrogen peroxide), silyl ether linkages (cleavable, for example, by fluoride ion, acid, or base), or allyl carbamate linkages (cleavable, for example, in the presence of a palladium complex). These linkages are capable of generating at least one free hydroxyl group after chemical cleavage. In one such embodiment, the second extension primer comprises or is a P17 primer disclosed herein (SEQ ID NO: 6) and the second cleavage site comprises one or more diol linkages that can be cleaved by oxidation, for example, by treatment with sodium periodate. In some embodiments, the diol linker comprises the structure of Formula (VIII) or (VIIIa) as described herein. In some embodiments, the azobenzene linker comprises the structure of Formula (X), (Xa) or (Xb) as described herein.

Some embodiments of the present disclosure relate to a solid support comprising a plurality of first strand polynucleotides and a plurality of second strand polynucleotides immobilized thereon, each first strand polynucleotides is extended from a modified P5 primer immobilized to the solid support, the modified P5 primer comprising a first cleavage site; each second strand polynucleotides is extended from a P7 primer immobilized to the solid support, the P5 primer comprising a second cleavage site; wherein both the first and the second strand polynucleotides are immobilized to the solid support at their 5' end, and wherein the first cleavage site capable of undergoing chemical cleavage by a Pd complex or a Ni complex, such as a Pd(0) complex or a Ni(0) complex. In some embodiments, the first cleavage site comprises a modified T nucleoside having an allyl functionality as described herein. The cleavage site may further include a moiety that may serve as 3' end blocking moiety, for example, a phosphate or a modified phosphate moiety, which remains on the first strand polynucleotides after the Pd/Ni cleavage reaction to block the 3'-OH of the cleaved immobilized first strand polynucleotides.

In some embodiments of the solid support described herein, the first and the second strand polynucleotides are immobilized to the solid support through covalent bonding with a polymer or hydrogel coating on a surface of the solid support. In one embodiment, the hydrogel or polymer coating comprises PAZAM. In some embodiments, the hydrogel or polymer coating is also covalently attached to the surface of the solid support, for example, through reaction with a functionalized silane deposited on the surface. In one embodiment, the functionalized silane is a norbornene derived silane. In one embodiment, the solid support comprises or is a flow cell.

Solid Support Surface

In some embodiments, the surface of the solid support before primer grafting comprises both regions coated with functionalized molecules and inert regions with no coatings. In some such embodiments, the functionalized molecule coatings are hydrogel or polymer coatings. The coated regions can comprise reactive sites, and thus, can be used to attach molecules through chemical bonding or other molecular interactions such as hybridization or covalent reaction. In some embodiments, the coated regions (e.g., reactive features, channels, pads, beads, or wells) and the inert regions (referred to as interstitial regions) can alternate so as to form a pattern or a grid. Such patterns can be in one or two dimensions. In some embodiments, the inert regions can be selected from glass regions, metal regions, mask regions or interstitial regions, or combinations thereof. Alternatively, these materials can form reactive regions. Inertness or reactivity will depend on the chemistry and processes used on the substrate. In one embodiment, the surface of the solid support comprises glass regions. In another embodiment, the surface comprises metal regions.

In some embodiments, a solid support described herein is forms at least part of a flow cell or is located in a flow cell. In some such embodiments, the flow cells further comprise polynucleotides attached to the surface of the solid support via the functionalized molecule coating, for example, a polymer or hydrogel coating. In some embodiments, the polynucleotides are present in the flow cells in polynucleotide clusters, wherein the polynucleotides of the polynucleotide clusters are attached to a surface of the flow cell via the hydrogel or polymer coating. In such embodiments, the surface of the flow cell body to which the polynucleotides are attached is considered the solid support. In other embodiments, a separate solid support having a hydrogel or polymer coated surface is inserted into the body of the flow cell. In preferred embodiments, the flow cell is a flow chamber that is divided into a plurality of lanes or a plurality of sectors, wherein one or more of the plurality of lanes or plurality of sectors comprises a surface that is coated with a covalently attached hydrogel or polymer coating described herein. In some embodiments of the flow cells described herein, the attached polynucleotides within a single polynucleotide cluster have the same or similar nucleotide sequence. In some embodiments of the flow cells described herein, the attached polynucleotides of different polynucleotide clusters have different or nonsimilar nucleotide sequences. Exemplary flow cells and substrates for manufacture of flow cells that can be used in method or composition set forth herein include, but are not limited to, those commercially available from Illumina, Inc. (San Diego, CA) or described in U.S. Publication Nos. 2010/0111768 A1 and 2012/0270305, each of which is incorporated herein by reference.

PAZAM

One embodiment of the hydrogel or polymer coating of the solid support surface comprises PAZAM, a polyacrylamide copolymer comprises the following two repeating units:

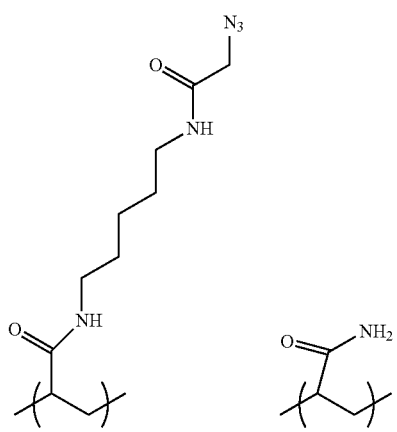

In some embodiments, PAZAM is a linear polymer. In some other embodiments, PAZAM is a lightly cross-linked polymer. PAZAM can be functionalized or modified for use in a composition or method set forth herein. The preparation of PAZAM and analogues thereof is disclosed in U.S. Pat. No. 9,012,022, which is hereby incorporated by reference in its entirety.

3' Blocking Groups

During SBS cycles, in order to ensure only a single incorporation occurs, a structural modification ("protecting group") is added to each labeled nucleotide that is added to the growing chain to ensure that only one nucleotide is incorporated. After the nucleotide with the protecting group has been added, the protecting group is then removed, under reaction conditions which do not interfere with the integrity of the DNA being sequenced. The sequencing cycle can then continue with the incorporation of the next protected, labeled nucleotide.

To be useful in DNA sequencing, nucleotides, and more usually nucleotide triphosphates, generally require a 3'-hydroxy protecting group so as to prevent the polymerase used to incorporate it into a polynucleotide chain from continuing to replicate once the base on the nucleotide is added. There are many limitations on types of groups that can be added onto a nucleotide and still be suitable. The protecting group should prevent additional nucleotide molecules from being added to the polynucleotide chain whilst simultaneously being easily removable from the sugar moiety without causing damage to the polynucleotide chain. Furthermore, the modified nucleotide needs to be tolerated by the polymerase or other appropriate enzyme used to incorporate it into the polynucleotide chain. The ideal protecting group therefore exhibits long term stability, be efficiently incorporated by the polymerase enzyme, cause blocking of secondary or further nucleotide incorporation and have the ability to be removed under mild conditions that do not cause damage to the polynucleotide structure, preferably under aqueous conditions.

Reversible protecting groups have been reported previously. For example, Metzker et al., (Nucleic Acids Research, 22 (20): 4259-4267, 1994) discloses the synthesis and use of eight 3'-modified 2-deoxyribonucleoside 5'-triphosphates (3'-modified dNTPs) and testing in two DNA template assays for incorporation activity. WO 2002/029003 describes a sequencing method which may include the use of an allyl protecting group to cap the 3'-OH group on a growing strand of DNA in a polymerase reaction. Other reversible protecting groups and methods of deprotecting them under DNA compatible conditions include azidomethyl or a modified azidomethyl group, which are disclosed in in International Application Publication Nos. WO 2004/018497 and WO 2014/139596, and are hereby incorporated by reference in their entireties.

One embodiment of the 3'-OH blocking group described herein is a phosphate group, which may be removed by a phosphatase.

Detectable Labels

Some embodiments described herein relate to the use of detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (Chem. Eur. J. 5(3):951-960, 1999) discloses dansyl-functionalised fluorescent moieties that can be used in the present invention. Zhu et al. (Cytometry 28:206-211, 1997) describes the use of the fluorescent labels Cy3 and Cy5, which can also be used in the present invention. Labels suitable for use are also disclosed in Prober et al. (Science 238:336-341, 1987); Connell et al. (BioTechniques 5(4):342-384, 1987), Ansorge et al. (Nucl. Acids Res. 15(11):4593-4602, 1987) and Smith et al. (Nature 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

In some embodiments, the detectable label may be used in the first cleavage site of a polynucleotide that is capable of undergoing Pd cleavage in the methods and the solid support described herein. In particular, the first cleavage site may comprise a labeled modified nucleotide or nucleoside. This approach may further streamline the currently Illumina manufacturing workflow. In one embodiment, the allyl modified P5 primer described herein can be modified to include a fluorescent tag that enables direct quantification of the grafting reaction immediately after it is completed, eliminating the requirement of a separate hybridization assay to perform such quantification step.

Linkers for Detectable Label

In some embodiments described herein, the nucleobase of the modified nucleotide or nucleoside can be linked to a detectable label as described above. In some such embodiments, the linkers used are cleavable. The use of a cleavable linker ensures that the label can, if required, be removed after detection, avoiding any interfering signal with any labeled nucleotide or nucleoside incorporated subsequently.

In some other embodiments, the linkers used are non-cleavable. Since in each instance where a labeled nucleotide of the invention is incorporated, no nucleotides need to be subsequently incorporated and thus the label need not be removed from the nucleotide.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidizing agents, light, temperature, enzymes, etc. The linker as discussed herein may also be cleaved with the same catalyst used to cleave the 3'-O-protecting group bond. Suitable linkers can be adapted from standard chemical protecting groups, as disclosed in Greene & Wuts, Protective Groups in Organic Synthesis, John Wiley & Sons. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from, e.g., the nucleotide base. Where the detectable label is attached to the base, the nucleoside cleavage site can be located at a position on the linker that ensures that part of the linker remains attached to the nucleotide base after cleavage.

Where the detectable label is attached to the base, the linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytosine, thymidine or uracil and the N-4 position on cytosine.

In some embodiments, the linker may consist of the similar functionality as the 3'-OH protecting group. This will make the deprotection and deprotecting processes more efficient, as only a single treatment will be required to remove both the label and the protecting group. Particularly preferred linkers are phosphine-cleavable azide containing linkers.

Cleavage Methods

Various cleavage methods may be used cleave one or both strands of the double-stranded nucleic acid molecule in the linearization step, for example for cleavage of the second strand polynucleotides described herein. Preferred but non-limited embodiments of suitable cleavage methods are discussed in further detail below.

A) Chemical Cleavage

The term "chemical cleavage" encompasses any method which utilizes a non-nucleic acid and non-enzymatic chemical reagent in order to promote/achieve cleavage of one or both strands of the double-stranded nucleic acid molecule. If required, one or both strands of the double-stranded nucleic acid molecule may include one or more non-nucleotide chemical moieties and/or non-natural nucleotides and/or non-natural backbone linkages in order to permit a chemical cleavage reaction at a specific cleavage site, preferably a pre-determined cleavage site. In one non-limiting embodiment, one strand of the double-stranded nucleic acid molecule may include a diol linkage which permits cleavage by treatment with periodate (e.g., sodium periodate). The diol linkage may be positioned at a cleavage site, the precise location of which may be selected by the user. It will be appreciated that more than one diol could be included at the cleavage site.

Diol linker units based on phosphoramidite chemistry suitable for incorporation into polynucleotide chains are commercially available from Fidelity Systems, Inc. (Gaithersburg, MD, USA). One or more diol units may be incorporated into a polynucleotide using standard methods for automated chemical DNA synthesis. In order to position the diol linker at an optimum distance from the solid support one or more spacer molecules may be included between the diol linker and the site of attachment to the solid support. The spacer molecule may be a non-nucleotide chemical moiety. Suitable spacer units based on phosphoramidite chemistry for use in conjunction with diol linkers are also supplied by Fidelity Systems, Inc. The diol linker is cleaved by treatment with a "cleaving agent", which can be any substance which promotes cleavage of the diol. The preferred cleaving agent is periodate, preferably aqueous sodium periodate ($NaIO_4$). Following treatment with the cleaving agent (e.g., periodate) to cleave the diol, the cleaved product may be treated with a "capping agent" in order to neutralize reactive species generated in the cleavage reaction. Suitable capping agents for this purpose include amines, such as ethanolamine. Advantageously, the capping agent (e.g., ethanolamine) may be included in a mixture with the cleaving agent (e.g., periodate) so that reactive species are capped as soon as they are formed.

The combination of a diol linkage and cleaving agent (e.g., periodate) to achieve cleavage of one strand of a double-stranded nucleic acid molecule is preferred for linearization of nucleic acid molecules on solid supported polyacrylamide hydrogels because treatment with periodate is compatible with nucleic acid integrity and with the chemistry of the hydrogel surface. However, the diol method may also be used for linearization of nucleic acids immobilized on other surfaces, including supports coated with functionalized silanes.

In a further embodiment, the strand to be cleaved (or the amplification primer from which this strand is derived if prepared by solid-phase amplification) may include a disulfide group which permits cleavage with a chemical reducing agent, e.g., Tris (2-carboxyethyl)-phosphate hydrochloride (TCEP).

B) Cleavage of Abasic Sites in a Double-Stranded Molecule

An "abasic site" is defined as a nucleoside position in a polynucleotide chain from which the base component has been removed. Abasic sites can occur naturally in DNA under physiological conditions by hydrolysis of nucleoside residues, but may also be formed chemically under artificial conditions or by the action of enzymes. Once formed, abasic sites may be cleaved (e.g., by treatment with an endonuclease or other single-stranded cleaving enzyme, exposure to heat or alkali), providing a means for site-specific cleavage of a polynucleotide strand.

In a non-limiting embodiment, an abasic site may be created at a pre-determined position on one strand of a double-stranded polynucleotide and then cleaved by first incorporating deoxyuridine (U) at a pre-determined cleavage site in the double-stranded nucleic acid molecule. This can be achieved, for example, by including U in one of the primers used for preparation of the double-stranded nucleic acid molecule by solid-phase PCR amplification. The enzyme uracil DNA glycosylase (UDG) may then be used to remove the uracil base, generating an abasic site on one strand. The polynucleotide strand including the abasic site may then be cleaved at the abasic site by treatment with endonuclease (e.g. EndoIV endonuclease, AP lyase, FPG glycosylase/AP lyase, EndoVIII glycosylase/AP lyase), heat or alkali.

Abasic sites may be used to generate a free 3'-hydroxyl moiety to act as a sequencing primer. If both amplification primers are modified such that they can be sequentially cleaved, the second cleavage can be used to cleave the first strand from the surface. The first (or second) primer could contain a uracil base, that can be cleaved by one enzyme (UDG), and the second (or first) primer could contain an 8-oxo-guanine base that can be cleaved by a second, orthogonal enzyme, FPG glycosylase. The second abasic site cleavage could be used to leave a sequencing primer attached to a surface, such that a G base is incorporated as the first cycle of sequencing, or the cleaved duplex strands can be denatured to allow hybridization of a sequencing primer in solution.

C) Cleavage of Ribonucleotides

Incorporation of one or more ribonucleotides into a polynucleotide strand which is otherwise comprised of deoxyribonucleotides (with or without additional non-nucleotide chemical moieties, non-natural bases or non-natural backbone linkages) can provide a site for cleavage using a chemical agent capable of selectively cleaving the phosphodiester bond between a deoxyribonucleotide and a ribonucleotide or using a ribonuclease (RNAse). Therefore, the invention also encompasses production of sequencing templates by cleavage of one strand (of a double-stranded nucleic acid molecule) at a site containing one or more consecutive ribonucleotides using such a chemical cleavage agent or an RNase. Preferably the strand to be cleaved contains a single ribonucleotide to provide a pre-determined site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$, or $Lu^{3+}$ (Chen et al., Biotechniques, 2002, 32: 518-520; Komiyama et al. Chem. Commun. 1999, 1443-1451)), Fe(3) or Cu(3), or exposure to elevated pH, e.g., treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions. The base composition of the ribonucleotide(s) is generally not material, but can be selected in order to optimize chemical (or enzymatic) cleavage. By way of example, rUMP or rCMP are generally preferred if cleavage is to be carried out by exposure to metal ions, especially rare earth metal ions.

The ribonucleotide(s) will typically be incorporated into one strand of the double-stranded nucleic acid molecule, and may be situated in a region thereof which is single-stranded when the two complementary strands of the double-stranded molecule are annealed (i.e. in a 5' overhanging portion). In particular, if the double-stranded nucleic acid molecule is prepared by solid-phase PCR amplification using forward and reverse amplification primers, one of which contains at least one ribonucleotide, the standard DNA polymerase enzymes used for PCR amplification are not capable of copying ribonucleotide templates. Hence, the products of the solid-phase PCR reaction will contain an overhanging 5' region comprising the ribonucleotide(s) and any remainder of the amplification primer upstream of the ribonucleotide(s).

The phosphodiester bond between a ribonucleotide and a deoxyribonucleotide, or between two ribonucleotides can also be cleaved by an RNase. Any endocytic ribonuclease of appropriate substrate specificity can be used for this purpose. If the ribonucleotide(s) are present in a region which is single-stranded when the two complementary strands of the double-stranded molecule are annealed (i.e. in a 5' overhanging portion), then the RNase will be an endonuclease which has specificity for single strands containing ribonucleotides. For cleavage with ribonuclease it is preferred to include two or more consecutive ribonucleotides, and preferably from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Polynucleotides incorporating one or more ribonucleotides can be readily synthesized using standard techniques for oligonucleotide chemical synthesis with appropriate ribonucleotide precursors. If the double-stranded nucleic acid molecule is prepared by solid-phase nucleic acid amplification, then it is convenient to incorporate one or more ribonucleotides into one of the primers to be used for the amplification reaction.

D) Photochemical Cleavage

The term "photo cleavage" or "photochemical cleavage" encompasses any method which utilizes light energy in order to achieve cleavage of one or both strands of the double-stranded nucleic acid molecule. A pre-determined site for photochemical cleavage can be provided by a non-nucleotide chemical spacer unit in one of the strands of the double-stranded molecule. Suitable photochemical cleavable spacers include the PC spacer phosphoramidite (4-(4,4'-Dimethoxytrityloxy) butyramidomethyl)-1-(2-nitrophenyl)-ethyl]-2-cyanoethyl-(N,N-diisopropyl)-phosphoramidite) supplied by Glen Research, Sterling, Virginia, USA. The spacer unit can be cleaved by exposure to a UV light source. This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable double-stranded nucleic acid molecule by solid-phase amplification.

E) PCR Stoppers

In another embodiment, the double-stranded nucleic acid may be prepared by solid-phase amplification using forward and reverse primers, one of which contains a "PCR stopper." A "PCR stopper" is any moiety (nucleotide or non-nucleotide) which prevents read-through of the polymerase used for amplification, such that it cannot copy beyond that point. The result is that amplified strands derived by extension of the primer containing the PCR stopper will contain a 5' overhanging portion. This 5' overhang (other than the PCR stopper itself) may be comprised of naturally occurring deoxyribonucleotides, with predominantly natural backbone linkages, i.e. it may simply be a stretch of single-stranded DNA. The molecule may then be cleaved in the 5' overhanging region with the use of a cleavage reagent (e.g., an enzyme) which is selective for cleavage of single-stranded DNA but not double stranded DNA, for example mung bean nuclease.

The PCR stopper may be essentially any moiety which prevents read-through of the polymerase to be used for the amplification reaction. Suitable PCR stoppers include, but are not limited to, hexaethylene glycol (HEG), abasic sites, and any non-natural or modified nucleotide which prevents read-through of the polymerase, including DNA analogues such as peptide nucleic acid (PNA).

Stable abasic sites can be introduced during chemical oligonucleotide synthesis using appropriate spacer units containing the stable abasic site. By way of example, abasic furan (5'-O-Dimethoxytrityl-1',2'-Dideoxyribose-3'-[(2-cyanoethyl)-(N,N-diisopropyl)]-phosphoramidite) spacers commercially available from Glen Research, Sterling, Virginia, USA, can be incorporated during chemical oligonucleotide synthesis in order to introduce an abasic site. Such a site can thus readily be introduced into an oligonucleotide primer to be used in solid-phase amplification. If an abasic site is incorporated into either forward or reverse amplification primer the resulting amplification product will have a 5' overhang on one strand which will include the abasic site (in single-stranded form). The single-stranded abasic site may then be cleaved by the action of a suitable chemical agent (e.g., exposure to alkali) or an enzyme (e.g., AP-endonuclease VI, Shida el al., Nucleic Acids Research, 1996, Vol. 24, 4572-4576).

F) Cleavage of Peptide Linkers

A cleavage site can also be introduced into one strand of the double-stranded nucleic molecule by preparing a conjugate structure in which a peptide molecule is linked to one strand of the nucleic acid molecule. The peptide molecule can subsequently be cleaved by a peptidase enzyme of the appropriate specificity, or any other suitable means of non-enzymatic chemical or photochemical cleavage. Typically, the conjugate between peptide and nucleic acid will be formed by covalently linking a peptide to one strand only of the double-stranded nucleic acid molecule, with the peptide portion being conjugated to the 5' end of this strand, adjacent to the point of attachment to the solid surface. If the double-stranded nucleic acid is prepared by solid-phase amplification, the peptide conjugate may be incorporated at the 5' end of one of the amplification primers. Obviously the peptide component of this primer will not be copied during PCR amplification; hence the "bridged" amplification product will include a cleavable 5' peptide "overhang" on one strand.

Conjugates between peptides and nucleic acids wherein the peptide is conjugated to the 5 1 end of the nucleic acid can be prepared using techniques generally known in the art. In one such technique the peptide and nucleic acid components of the desired amino acid and nucleotide sequence can be synthesized separately, e.g., by standard automated chemical synthesis techniques, and then conjugated in aqueous/organic solution. By way of example, the OPeC™ system commercially available from Glen Research is based on the "native ligation" of an N-terminal thioester-functionalized peptide to a 5'-cysteinyl oligonucleotide. Pentafluorophenyl S-benzylthiosuccinate is used in the final coupling step in standard Fmoc-based solid-phase peptide assembly. Deprotection with trifluoroacetic acid generates, in solution, peptides substituted with an N-terminal S-benzylthiosuccinyl group. O-trans-4-(N-a-Fmoc-S-tert-butylsulfenyl-1-cysteinyl) aminocyclohexyl O-2-cyanoethyl-N,N-diisopropylphosphoramidite is used in the final coupling step in standard phosphoramidite solid-phase oligonucleotide assembly. Deprotection with aqueous ammonia solution generates in solution 5'-S-tert-butylsulfenyl-L-cysteinyl functionalized oligonucleotides. The thiobenzyl terminus of the Modified Peptide is converted to the thiophenyl analogue by the use of thiophenol, whilst the Modified Oligonucleotide is reduced using the tris(carboxyethyl)phosphine. Coupling of these two intermediates, followed by the "native ligation" step, leads to formation of the Oligonucleotide-Peptide Conjugate.

The conjugate strand containing peptide and nucleic acid can be covalently attached to a solid support using any suitable covalent linkage technique known in the art which is compatible with the chosen surface. For example, covalent attachment to a solid supported polyacrylamide hydrogel surface can be achieved by inclusion of a thiophosphate group on the "free" end of the peptide component (i.e. the end not conjugated to the nucleic acid). If the peptide/nucleic acid conjugate structure is an amplification primer to be used for solid-phase PCR amplification, attachment to the solid support must leave the 3' end of the nucleic acid component free.

The peptide component can be designed to be cleavable by any chosen peptidase enzyme, of which many are known in the art. The nature of the peptidase is not particularly limited, it is necessary only for the peptidase to cleave somewhere in the peptide component. Similarly, the length and amino acid sequence of the peptide component is not particularly limited except by the need to be "cleavable" by the chosen peptidase.

The length and precise sequence of the nucleic acid component is also not particularly limited, it may be of any desired sequence. If the nucleic acid component is to function as a primer in solid-phase PCR, then its length and nucleotide sequence will be selected to enable annealing to the template to be amplified.

Denaturation

In any embodiments of method used for cleavage, the product of the cleavage reaction may be subjected to denaturing conditions in order to remove the portion(s) of the cleaved strand(s) that are not attached to the solid support. Suitable denaturing conditions will be apparent to the skilled reader with reference to standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds., Ausubel et al.). Denaturation (and subsequent re-annealing of the cleaved strands) results in the production of a sequencing template which is partially or substantially single-stranded. A sequencing reaction may then be initiated by hybridization of a sequencing primer to the single-stranded portion of the template.

In other embodiments, sequencing can be initiated directly after the cleavage step with no need for denaturation to remove a portion of the cleaved strand(s). If the cleavage step generates a free 3' hydroxyl group on one cleaved strand still hybridized to a complementary strand then sequencing can proceed from this point using a strand-displacement polymerase enzyme without the need for an initial denaturation step. In particular, strand displacement sequencing may be used in conjunction with template generation by cleavage with nicking endonucleases, or by hydrolysis of an abasic site with endonuclease, heat or alkali treatment.

Methods of Sequencing

In some embodiments, the solid support and the methods described herein can be used for determining a nucleotide sequence of a polynucleotide. In such embodiments, the method can comprise the steps of (a) contacting a polynucleotide polymerase with delinearized polynucleotide clusters attached to a surface of a substrate (e.g., via any one of the polymer or gel coatings described herein); (b) providing nucleotides to the surface of the substrate such that a detectable signal is generated when one or more nucleotides are utilized by the polynucleotide polymerase; (c) detecting signals at one or more attached polynucleotide (or one or more clusters produced from the attached polynucleotides); and (d) repeating steps (b) and (c), thereby determining a nucleotide sequence of a substrate-attached polynucleotide.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate (e.g., via any one of the polymer coatings described herein). In such a process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide.

Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

In some embodiments of the above-described method, which employ a flow cell, only a single type of nucleotide is present in the flow cell during a single flow step. In such embodiments, the nucleotide can be selected from the group consisting of dATP, dCTP, dGTP, dTTP and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises an optical signal. In other embodiments, the detectable signal comprises a non-optical signal. In such embodiments, the non-optical signal comprises a change in pH at or near one or more of the polynucleotide templates.

Applications and uses of substrates of the present disclosure have been exemplified herein with regard to nucleic acids. However, it will be understood that other analytes can be attached to a substrate set forth herein and analyzed. One or more analytes can be present in or on a substrate of the present disclosure. The substrates of the present disclosure are particularly useful for detection of analytes, or for carrying out synthetic reactions with analytes. Thus, any of a variety of analytes that are to be detected, characterized, modified, synthesized, or the like can be present in or on a substrate set forth herein. Exemplary analytes include, but are not limited to, nucleic acids (e.g., DNA, RNA or analogs thereof), proteins, polysaccharides, cells, antibodies, epitopes, receptors, ligands, enzymes (e.g., kinases, phosphatases or polymerases), small molecule drug candidates, or the like. A substrate can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules, and the like.

In some embodiments, analytes can be distributed to features on a substrate such that they are individually resolvable. For example, a single molecule of each analyte can be present at each feature. Alternatively, analytes can be present as colonies or populations such that individual molecules are not necessarily resolved. The colonies or populations can be homogenous with respect to containing only a single species of analyte (albeit in multiple copies). Taking nucleic acids as an example, each feature on a substrate can include a colony or population of nucleic acids and every nucleic acid in the colony or population can have the same nucleotide sequence (either single stranded or double stranded). Such colonies can be created by cluster amplification or bridge amplification as set forth previously herein. Multiple repeats of a target sequence can be present in a single nucleic acid molecule, such as a concatemer created using a rolling circle amplification procedure. Thus, a feature on a substrate can contain multiple copies of a single species of an analyte. Alternatively, a colony or population of analytes that are at a feature can include two or more different species. For example, one or more wells on a substrate can each contain a mixed colony having two or more different nucleic acid species (i.e. nucleic acid molecules with different sequences). The two or more nucleic acid species in a mixed colony can be present in non-negligible amounts, for example, allowing more than one nucleic acid to be detected in the mixed colony.

EXAMPLES

Additional embodiments are disclosed in further detail in the following examples, which are not in any way intended to limit the scope of the claims.
General Surface Preparation Protocol
Silanization of Cleaned HiSeq® Flow Cells Norbornene-functionalized flow cells are produced via a Chemical Vapor Deposition (CVD) method using either a YES (Yield Engineering Systems) silanization chamber or a desiccator. The CVD process is typically conducted at 60° C. for periods between 1-24 h.

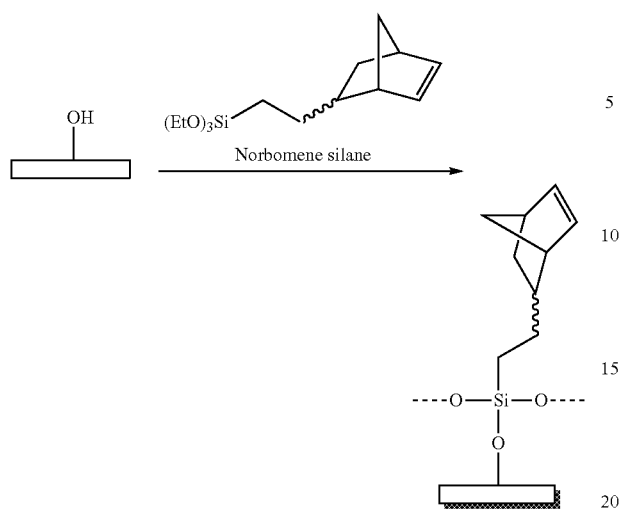

PAZAM Coupling

The silanized flow cell can then be coated and grafted using multiple tooling options. For example, a cBot fully automated clonal cluster generation system for Illumina sequencing (available from Illumina) can be used to perform these operations. In a typical procedure, the flow cell is initially flushed with IPA/H₂O (1:1; 100 μL/min, 2 min). Next, DI water is flushed through the channels (100 μL/min, 2 min). An aliquot of a 0.5 wt % PAZAM (aq.) solution is prepared (sufficient for 8 channels). The polymer is flowed into the channels (100 μL/min, 2 min). The PAZAM coupling step is completed over 1 h at 60° C. After completion of this step, the channels are flushed with water in readiness for the following grafting step. After completing the polymer coating steps, the flow cell can be stored at 4° C. in buffer (e.g., saline-sodium citrate (SSC) buffer). Alternatively, the grafting step can be completed immediately after PAZAM coating.

Grafting of PAZAM Coated Flow Cells and QC

This protocol describes the procedure for grafting a HiSeq® flow cell using a cBot system (ILMN). The grafting procedure furnished a flow cell surface where the allyl-modified P5 sequence oligo primer and the diol-modified P7 sequence primer are covalently attached to the PAZAM surface in approximately a 1:1 ratio. A typical grafting mix is prepared following the standard Illumina procedure and is dependent on the primer concentration to be used. The typical primer concentration employed is around 1-20 μM, targeting primer densities between 20-250000 units (fluorescence counts). The QC step is performed following the standard Illumina procedure using a cBot system before imaging on a Typhoon (fluorescence flatbed scanner).

After QC, the channels of the flow cell are flushed with 5×SSC (60 μL/min, total volume=300 μL/flow cell) to remove the sodium hydroxide (used to perform the dehybridization step).

The grafted flow cell is then stored at 4° C. prior to use in downstream biochemistry processes (clustering, sequencing).

Example 1

In this example, a modified oligonucleotide comprising a modified thymine nucleoside analogue was used as a specific site to be cleaved efficiently by chemical reagents under biological conditions without interfering with duplex pairing properties and PCR extension properties.

In particular, the oligonucleotide contains a single modified T-nucleoside with a vinyl group attached on the 5'-C position. When treated with a solution of Na₂PdCl₄ or (PdAllylCl)₂ and THP in aqueous buffer (in situ generating a palladium (0) complex), the oligonucleotide was cleaved at the modified T position with the resulting shorter oligo containing a phosphate group at 3'-end. This reaction is illustrated in Scheme 1 below, wherein Nu represents a nucleophile.

Scheme 1.

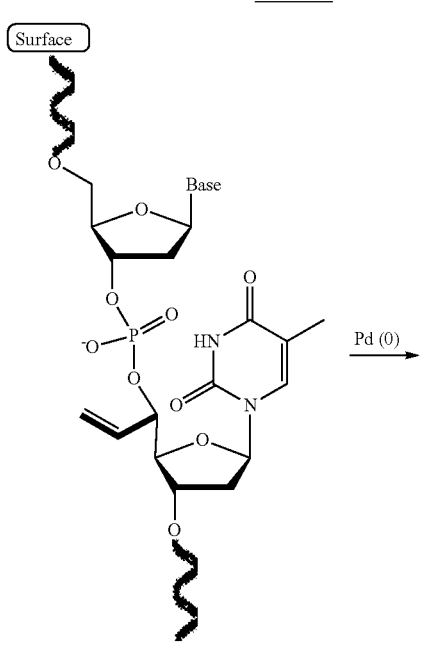

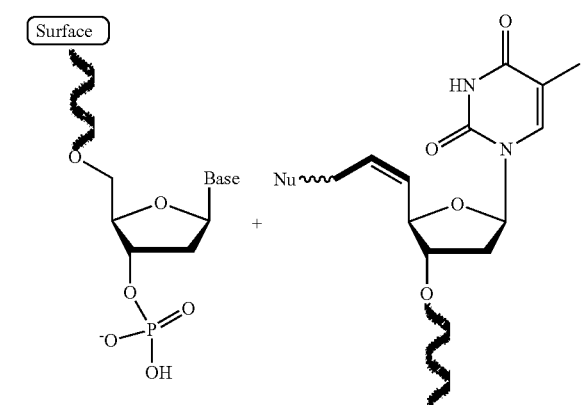

The synthesis of the modified T nucleoside phosphoramidite is described in Scheme 2. The starting material is commercially available. The majority of reaction steps gave >70% yield. Excellent yield of the final DNA oligonucleotide comprising the modified T nucleoside was also reported.

Scheme 2.
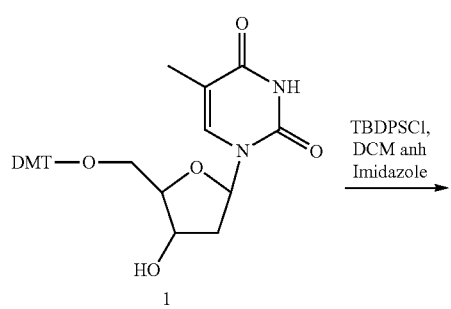
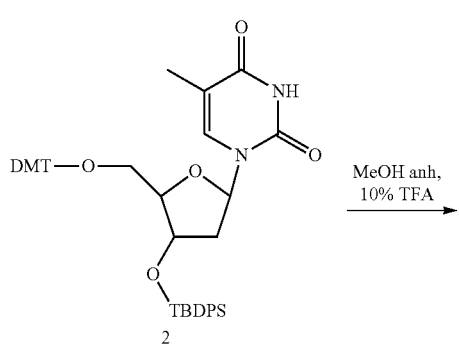
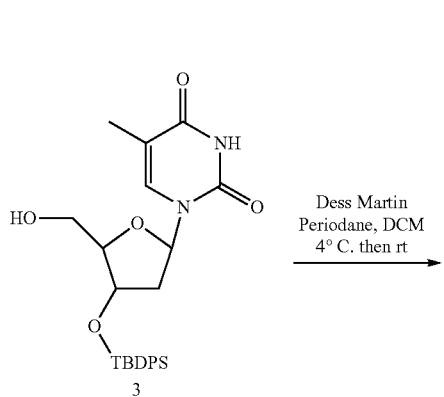
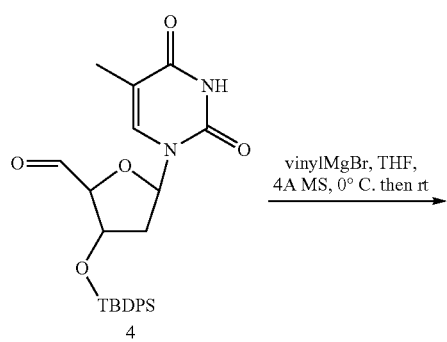
-continued
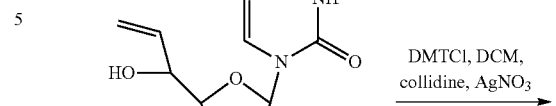
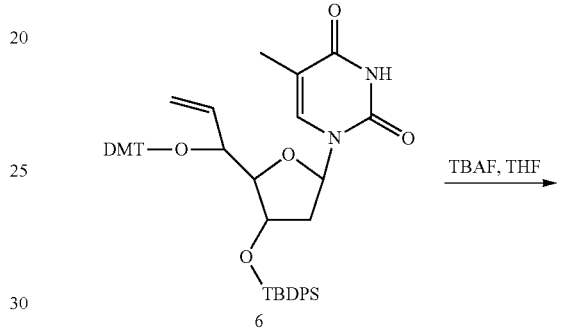
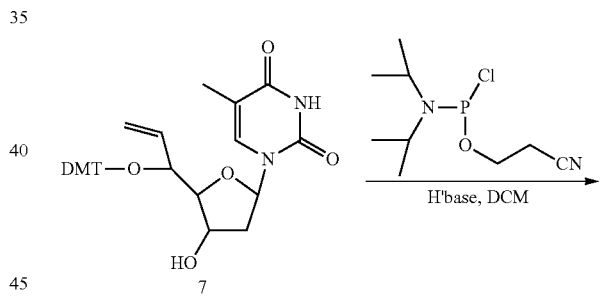
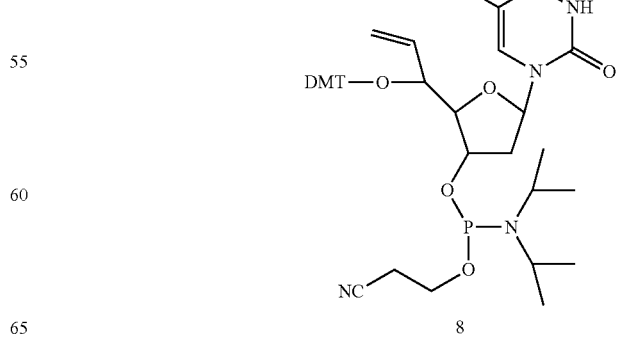

5'-O-dimethoxytrityl-thymidine-3'-O-TBDPS (2). 5'-O-dimethoxytrityl-thymidine (1) (15 g, 1 eq, 27.54 mmol) was dried under high vacuum for 1 h. DCM anhydrous (300 ml) was added under $N_2$. To this solution was added first imidazole (4.69 g, 2.5 eq, 69 mmol) as a solid then t-butyl diphenylsilylchloride (9.1 ml, 1.3 eq, 35.8 mmol). The reaction mixture was stirred under $N_2$ at rt for 1 h. The completion of reaction was checked by TLC. The reaction was quenched with sat. $NaHCO_3$ solution (100 ml) and stirred for 5 min. DCM (100 ml) was added to reaction mixture and the aqueous layer was extracted with DCM 2 times. The organic phase was washed with sat. $NaHCO_3$ (200 ml) then brine (200 ml). After drying the combined organics over $MgSO_4$ the solvent was removed under vacuum and dried very well under vacuum to give 2 as a white/light yellow foam. Compound 2 was used crude in the next step. LC-MS (ES and CI): (−ve) m/z 782 (M−H⁺), (−ve) m/z 817 (M+Cl⁻). ¹H NMR (CDCl₃) δ 0.99 (s, 9H, tBu), 1.27 (s, 3H, Me), 1.96-2.06 (m, 1H, H-2'), 2.25-2.35 (m, 1H, H-2'), 2.80 (dd, J=4, 12 Hz, 1H, H-5'), 3.15 (dd, J=4, 12 Hz, 1H, H-5'), 3.71 (s, 6H, OMe), 3.96-4.01 (m, 1H, H-4'), 4.45-4.50 (m, 1H, H-3'), 6.42 (dd, J=8, 12 Hz, 1H, H-1'), 6.79-6.72 (m, 4H, aromatics), 7.68-7.00 (m, 24H, aromatics+CH), 8.01 (s, 1H, NH).

3'-O-TBDPS-thymidine (3). Crude 5'-O-dimethoxytrityl-thymidine-3'-O-TBDPS (2) (27.54 mmol as a maximum) was dissolved in anhydrous MeOH (300 ml) under $N_2$. TFA (10% in vol, 30 ml) was added and the reaction was stirred at rt under $N_2$ for 2 h 30 min. Completion of reaction was followed by TLC. Reaction was quenched carefully with sat. $NaHCO_3$ (200 ml) and stir at rt for 10 min. MeOH was removed under vacuum. Residual mixture was diluted with DCM (300 ml) and partition with sat. $NaHCO_3$. Aqueous phase was extracted twice with DCM, then organic phases were washed with sat. $NaHCO_3$, dried with $MgSO_4$ and concentrated under vacuum. The crude material was purified by column (Biotage, 100 g Ultra-Si, PE/EtOAc) to give compound 3 as a white foam (13.15 g, 99%). LC-MS (ES and CI): (−ve) m/z 479 (M−H⁺), (+ve) m/z 481 (M+H⁺). ¹H NMR (d₆ DMSO) δ 1.46 (s, 9H, tBu), 2.15 (s, 3H, Me), 2.35-2.53 (m, 2H, H2'), 3.57-3.67 (m, 1H, H5'), 3.77-3.87 (m, 1H, H5'), 4.30-4.36 (m, 1H, H4'), 4.80-4.86 (m, 1H, H3'), 5.41 (t, J=5.2 Hz, 1H), 6.72 (dd, J=8.7, 5.7 Hz, 1H), 7.82-7.94 (m, 6H, aromatics+CH), 8.00-8.05 (m, 5H, aromatics), 11.73 (s, 1H, NH).

Alternative synthesis of Compound (3). 5'-O-dimethoxytrityl-thymidine (1, 40 g, 73.4 mmol) was treated with TBDPSCl (1.3 eq.) and imidazole (2.5 eq.), in DCM (0.127 M) at rt for 2 h, followed by PTSA (3 eq.) in methanol (0.097 M) for 1 h, to provide compound (3) in 100% yield in a one-pot preparation. No work-up was needed following the silylation step, solvent evaporation and overnight drying steps were removed, and the reaction was performed with exposure to air. Use of PTSA in place of TFA reduced acid-catalyzed rearrangement of the ribose of the thymidine nucleoside.

3'-O-TBDPS-5'aldehyde-thymidine (4). 3'-O-TBDPS-thymidine (3) (5.16 g, 1 eq, 10.75 mmol) was dried under high vacuum lane overnight as well as 4 Å MS. Then anhydrous DCM (250 ml) was added to compound 3 and 4 Å MS under $N_2$, and then cooled down to 4° C. with an ice batch. Dess Martin Periodane was added by portion under $N_2$ (3×1.823 g, 1.2 eq, 12.9 mmol) and the reaction was stirred at 4° C. under $N_2$ for 1 h 30 min. Reaction was checked by LCMS. The reaction was allowed to warm at rt and the reaction was stirred under $N_2$ for 4 h, or until completion of reaction. Once completed a $Na_2SO_3$ solution was added to the reaction (100 ml) and stirred at rt for 10 min. The 2 phases were separated and the aqueous phase was extracted 2 times with DCM. The organic phase was then washed with $Na_2CO_3$ and sat. $NaHCO_3$, dried with $MgSO_4$ and concentrated under vacuum. The crude material was dried under high vacuum overnight ready for next step. Co-evaporation with toluene can be done as well to improve dryness. LC-MS (ES and CI): (−ve) m/z 477 (M−H⁺), (−ve) m/z 513 (M+Cl⁻), (+ve) m/z 479 (M+H⁺), (+ve) m/z 501 (M+Na⁺); (−ve) m/z 495 (hydrate-H⁺), (+ve) m/z 519 (hydrate+Na⁺).

Alternative Synthesis of Aldehyde (4). Compound (3, 0.5 g) was treated with EDC (3 eq.) and DCA (0.5 eq.) in DMSO at rt for 6 h to provide compound (4) via a Pfitzner-Moffat oxidation, without over-oxidation to the carboxylic acid that was observed with the Dess-Martin periodinane method (and required the addition of a large excess of Grignard reagent in the subsequent step to quench the carboxylic acid contaminant).

3'-O-TBDPS-5'vinyl-thymidine (5). 3'-O-TBDPS-5'aldehyde-thymidine (4) (5.16 g, 1 eq, 10.75 mmol) was dried under high vacuum lane overnight as well as 4 A MS. Then anhydrous THF (150 ml) was added to compound 3 and 4 A MS under $N_2$. A solution of 1M vinyl magnesium bromide in THF (21.5 ml, 2 eq, 21.5 mmol) was added very slowly at rt over 30 min. The reaction was stirred at rt under $N_2$ for 2 h, and checked by LCMS. If needed, some extra vinyl magnesium bromide can be added dropwise (0.3 eq, 3.22 ml) and the reaction stirred for a further 1 h. Once completed a solution of 1M AcOH in water (60 ml, pH=6) was added to the reaction and stirred at rt for 10 min. The reaction was diluted with DCM and the 2 phases were separated. The aqueous phase was extracted 2 times with DCM. The organic phases were then washed 2× with sat. $NaHCO_3$, dried with $MgSO_4$ and concentrated under vacuum. The residue was purified by column (Biotage, 100 g kpSi, PE/EtOAc) to give compound 5 as a cream foam (2.01 g, 37% over 2 steps). LC-MS (ES and CI): (−ve) m/z 505 (M−H⁺), (−ve) m\z 541 (M+Cl⁻), (+ve) m/z 507 (M+H⁺). ¹H NMR (400 MHz, Chloroform-d) δ 1.01 (d, J=10.1 Hz, 9H, tBu), 1.80 (s, 3H, Me), 2.02-2.22 (m, 2H, H2'), 3.48-3.54 (m, 0.6H, H5'), 3.81 (t, J=2.2 Hz, 0.6H, H4'), 3.97-4.02 (m, 0.4H, H4'), 4.13-4.22 (m, 0.4H, H5'), 4.33-4.50 (dm, 1H, H3'), 4.82-5.17 (m, 2H, CH2=CH—), 5.24-5.43 (m, 0.4H, CH2=CH—), 5.52-5.75 (m, 0.6H, CH2=CH—), 6.04-6.29 (ddd, J=21.2, 8.3, 6.0 Hz, 1H, H1'), 7.26-7.46 (m, 7H, Arom+CH), 7.50-7.66 (m, 4H, Arom), 8.23 (s, 1H, NH).

Alternative Synthesis of Allyl Alcohol (5). Aldehyde (4) was treated with vinyl magnesium chloride (2.5 eq.) in THF at rt to provide compound (5). Use of the chloride reagent in place of the bromide reduced the production of a brominated analog of the desired product (14% in above method) without introduction of a chloride variant of the desired product.

3'-O-TBDPS-5'vinyl-5'DMT-thymidine (6). 3'-O-TBDPS-5'vinyl-thymidine (5) (2.01 g, 1 eq, 3.97 mmol) was dried under high vacuum lane overnight. AgNO₃ was added and solids were dried under high vacuum for another 30 min. Anhydrous DCM was added under $N_2$ to the reaction, then collidine (1.05 ml, 2 eq, 7.94 mmol) and finally DMT-Cl (2.02 g, 1.5 eq, 5.96 mmol) as a solid. The reaction was stirred at rt under $N_2$ for 3 h; completion was checked by TLC (PE/EtOAc, 6:4 +1% NEt₃). The reaction was then diluted with DCM and filter onto celite and the solid washed with more DCM. The solution was then partitioned with 1% $H_2SO_4$ (60 ml) and extracted with DCM. The organic phases were washed 2× with sat. $NaHCO_3$, dried over $MgSO_4$ and concentrated under vacuum to give the crude 6 as a foam. It will be used without further purification in next step. LC-MS (ES and CI): (−ve) m/z 807 (M−H⁺), (+ve) m/z 809 (M+H⁺).

Alternative Procedure: A solution of compound (5, 6.7 g, 13.2 mmol) and 2,3,5-collidine in anhydrous DCM was dried for 30 min on molecular sieves. The resulting solution was then added to a flask containing 4,4'-dimethoxytriphenylmethyl chloride (6.7 g) and molecular sieves. AgNO$_3$ was added and the reaction was stirred for 1 h. The resulting mixture was diluted with DCM (40 mL) and was filtered through diatomaceous earth, rinsing with DCM (3×40 mL). MeOH was added (240 mL) to the filtrate and the mixture was stirred for 10 min, then was transferred to a separatory funnel, washed with satd. aq. NaHCO$_3$ (2×400 mL), dried (Na$_2$SO$_4$), and concentrated under vacuum to give the crude product as a yellow foam.

5'Vinyl-5'DMT-thymidine (7). 3'-O-TBDPS-5'allyl-5'DMT-thymidine (6) (1 eq, 3.97 mmol from previous step) was dried under high vacuum lane. Anhydrous THF (12 ml) was added under N$_2$ and cooled down to 4° C. A solution of 1M TBAF in THF (4.37 ml, 1.1 eq, 4.37 mmol) was added dropwise at 4° C. After 5 min at 4° C., the reaction was allowed to warm at rt and stirred under N$_2$ for 3 h. Completion of reaction was followed by TLC (PE/EtOAc, 3:7+1% NEt$_3$). The reaction was diluted with EtOAc and partitioned with sat. NaHCO$_3$. Aqueous phase was extracted with EtOAc, then organic phase was washed with sat. NaHCO$_3$ then brine, dried over MgSO$_4$ and concentrated under vacuum. The residue was purified by column (Biotage, 25 g KpSi, PE/EtOAc+1% NEt$_3$) to give compound 7 as a white foam (1.81 g, 80% over 2 steps). LC-MS (ES and CI): (−ve) m/z 569 (M−H⁺), (+ve) m/z 571 (M+H⁺). $^1$H NMR (400 MHz, DMSO-d6) δ 1.46 (s, 1H, Me), 1.65 (s, 2H, Me), 1.97-2.13 (m, 2H, H2'), 3.64 (m, 1H, H4'), 3.85 (dd, J=8.0, 4 Hz, 0.4H, H5'), 3.92 (dd, J=8.0, 4 Hz, 0.6H, H5'), 4.31-4.45 (m, 1H, H3'), 4.55-4.86 (m, 2H, CH=CH2-), 5.27 (dd, J=7.4, 4.8 Hz, 1H, OH), 5.52-5.71 (m, 1H, CH=CH2-), 6.11 (dt, J=8.1, 5.8 Hz, 1H, H1'), 6.86 (dd, J=8, 4 Hz, 4H, Arom.), 7.13-7.35 (m, 7H, Arom.+CH), 7.40-7.50 (m, 3H, Arom.), 11.35 (s, 1H).

5'Vinyl-5'DMT-thymidine-phosphoramidite (8). 5'Vinyl-5'DMT-thymidine (800 mg, 1.4 mmol) was dried under high vacuum lane. Anhydrous DCM (7 ml) was added under N$_2$ and stirred with molecular sieves for 10 min at rt. To the solution, Hunig's base (0.74 ml, 4.2 mmol) was added and followed by 2-cyanoethyl N,N-diisopropylchlorophosphoramidite (407 ul, 0.52 mmol). The reaction was stirred at rt under N$_2$ for 3 h. Completion of reaction was followed by TLC (PE/EtOAc, 4:6). The reaction concentrated under vacuum. The residue was purified by column (Biotage, 25 g KpSi, PE/EtOAc+1% NEt$_3$) to give compound 8 as a white foam (930 mg). LC-MS (ES and CI): (−ve) m/z 770 (M−H⁺), (+ve) m/z 771 (M+H⁺). $^1$H NMR (400 MHz, DMSO-d6) δ 0.96-1.27 (m, 21H), 1.50 (d, J=5.9 Hz, 1H), 1.66 (s, 3H), 2.02-2.37 (m, 3H), 2.58-2.74 (m, 2H), 2.78 (td, J=5.8, 3.9 Hz, 1H), 3.46-3.69 (m, 6H), 3.76-3.93 (m, 2H), 3.96-4.10 (m, 2H), 4.61 (ddd, J=17.5, 14.2, 8.6 Hz, 2H), 4.68-4.98 (m, 3H), 5.43-5.79 (m, 1H), 6.04 (dt, J=9.6, 5.1 Hz, 1H), 6.13 (dt, J=10.7, 6.9 Hz, OH), 6.85 (ddt, J=8.2, 5.2, 2.4 Hz, 6H), 7.09-7.34 (m, 11H), 7.34-7.50 (m, 4H), 11.37 (d, J=6.1 Hz, 1H). $^{31}$P NMR (162 MHz, DMSO) δ 147.94, 147.16, 147.03.

Cleavage Efficiency Analysis

The cleavage efficiency was assessed on a high primer density PAZAM surface (40-60 k). A (non-patterned) HiSeq® flow cell was prepared following standard procedures described herein. Norbornene derived silane was deposited on the substrate surface using CVD method, followed by click coupling of the polymer (PAZAM) to the substrate surface followed by a second Click coupling procedure to graft the polymer surface with the modified P7 oligos containing the allyl T nucleoside analog (5'-Alkyne-TTTTTTTTTXCAAGCAGAAGACGGCATACGAGAT, where X indicates the site where the modified T nucleoside described above was incorporated).

The modified P7 oligos were grafted on the PAZAM flow cell with similar density to the standard P7 oligos. The grafting efficiency for the modified P7 oligo was also similar to the standard 5'-functionalized P5 and P7 oligos. The flow cell surface was treated with 1 mM Na$_2$PdCl$_4$, 10 mM THP in 1×EA incorporation mix (containing 50 mM ethanol amine-HCl (pH 9.9), 50 mM NaCl and 0.05% Chaps) at 60° C. for 10 min. The TET-QC assay was used to demonstrate successful cleavage of the allyl T modified P5 oligos from the surface after treatment with the in situ generated Pd(0) complex.

Figure 2A:
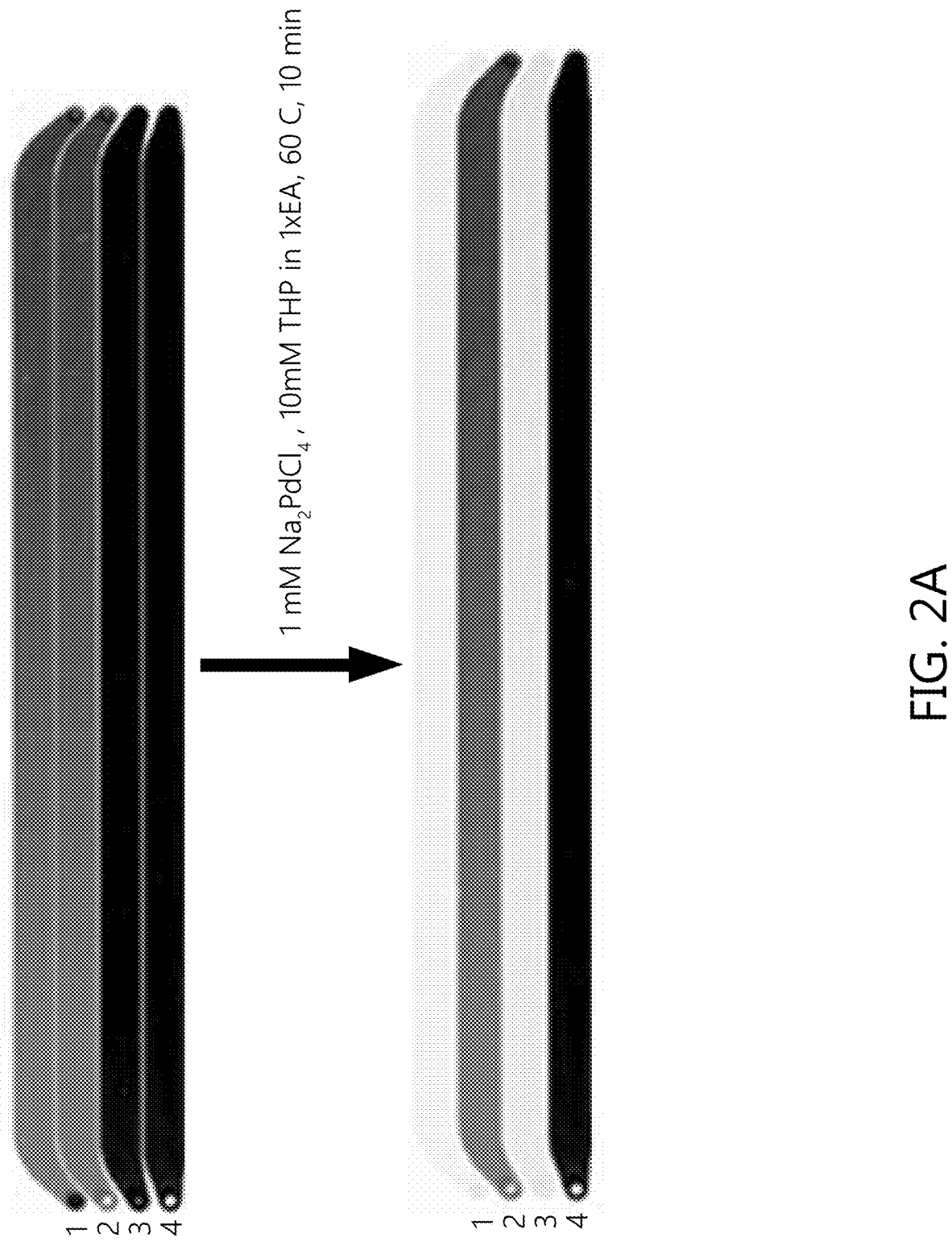
FIG. 2A illustrates Typhoon images of a non-patterned high primer density flow cell surface before and after treatment with a Pd(0) complex, where the flow cell surface is grafted with allyl modified primers.
Figure 2B:
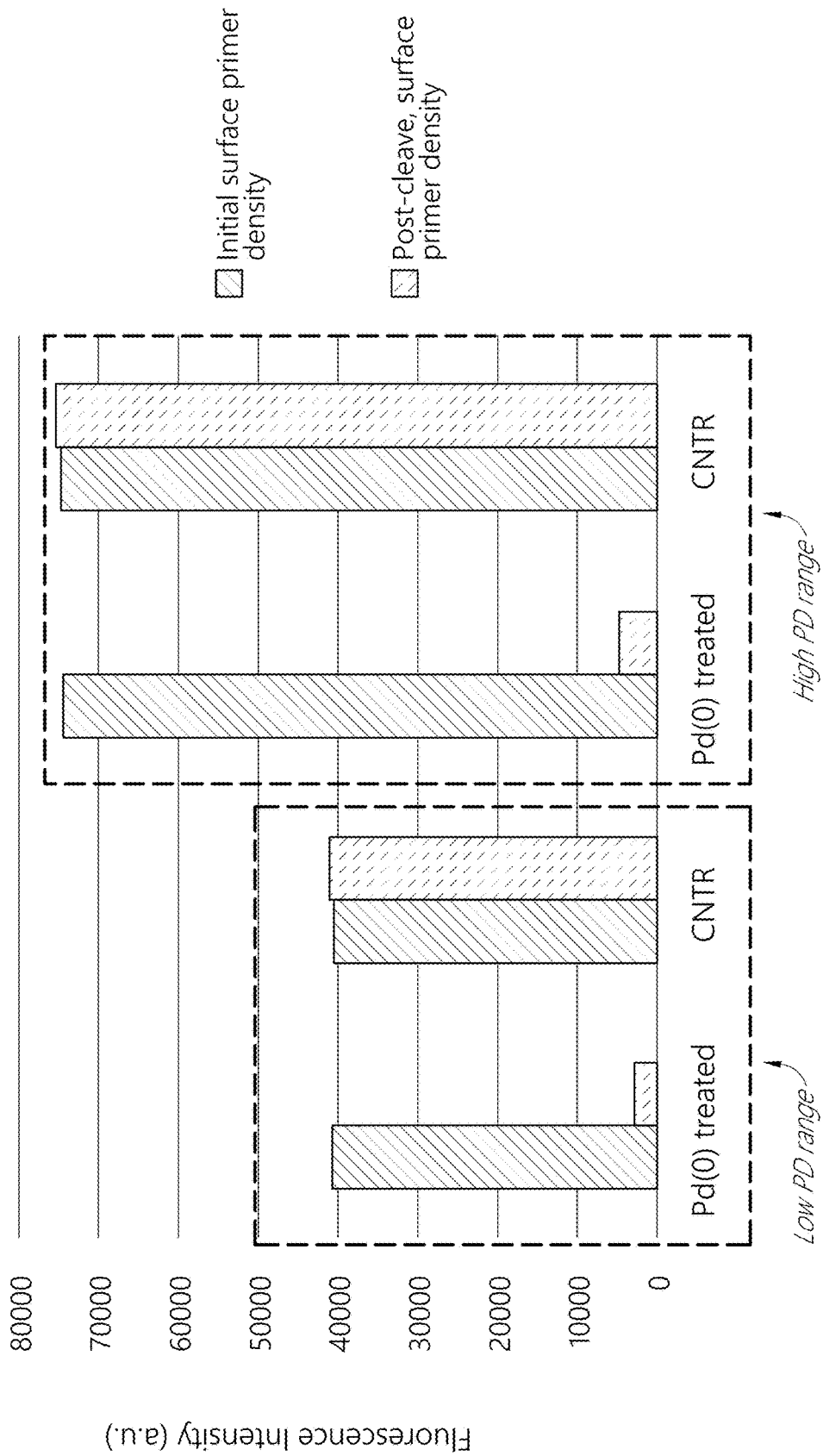
FIG. 2B is a bar chart demonstrating the change in primer density after the Pd(0) treatment described in FIG. 2A as compared flow cell surface grafted with control primers without the allyl functionality.

FIG. 2A illustrates the Typhoon image of the flow cell surface before and after the Pd(0) treatment. FIG. 2B shows the change in primer density prior to and post Pd(0) treatment, comparing the flow cell surface treated with the modified P5 oligos with the standard control. At both the low primer density and high primer density ranges, the Pd(0) treated flow cell surface grafted with the modified P5 oligos indicated substantial changes in fluorescent intensity. The results suggested very efficient cleavage (~95%, fluorescence assay) using this method. In comparison, the standard P5 oligo granted flow cell surface did not show much variation in fluorescent intensity, indicating the standard P5 oligos were not cleaved by the Pd(0) complex.

Sequencing Run Results Analysis

The capability of the above described modified allyl T nucleoside to undergo effective cleavage was further analyzed by performing a short sequencing run. In this experiment, flow cells were fabricated following a similar method described above. Therefore, the allyl-T modified P5 alkyne oligo and a standard P7 alkyne oligo were graft onto PAZAM coated flow cells at various surface primer densities. To ensure efficient resynthesis, the position of the allyl modification was shifted further towards the 3' end of the modified P5 oligo. The sequence of the grafting primers used for SBS flow cell fabrication are described as following:

P5:
5'-Alkyne-TTTTTTTTTTAATGATACGGCGACCACCGAGAXCTACAC

P7:
5'-Alkyne-TTTTTTTTTTCAAGCAGAAGACGGCATACGA(8-oxo G)AT

X=allyl modification, as described in Scheme 1.

Typical cleavage conditions involve incubating the allyl-P5 grafted surface with a Na$_2$PdCl$_4$/THP solution at 60° C. for 10 min. The Pd(0) treated PAZAM surfaces were stable in these conditions and can go on to support several hundred cycles of sequencing. In addition, no other side reactions were detected and subsequent cleavage of the P7 oligo, as determined indirectly by the PET resynthesis, remains unaffected confirming the orthogonality and specificity of the allyl approach.

Figure 3A:
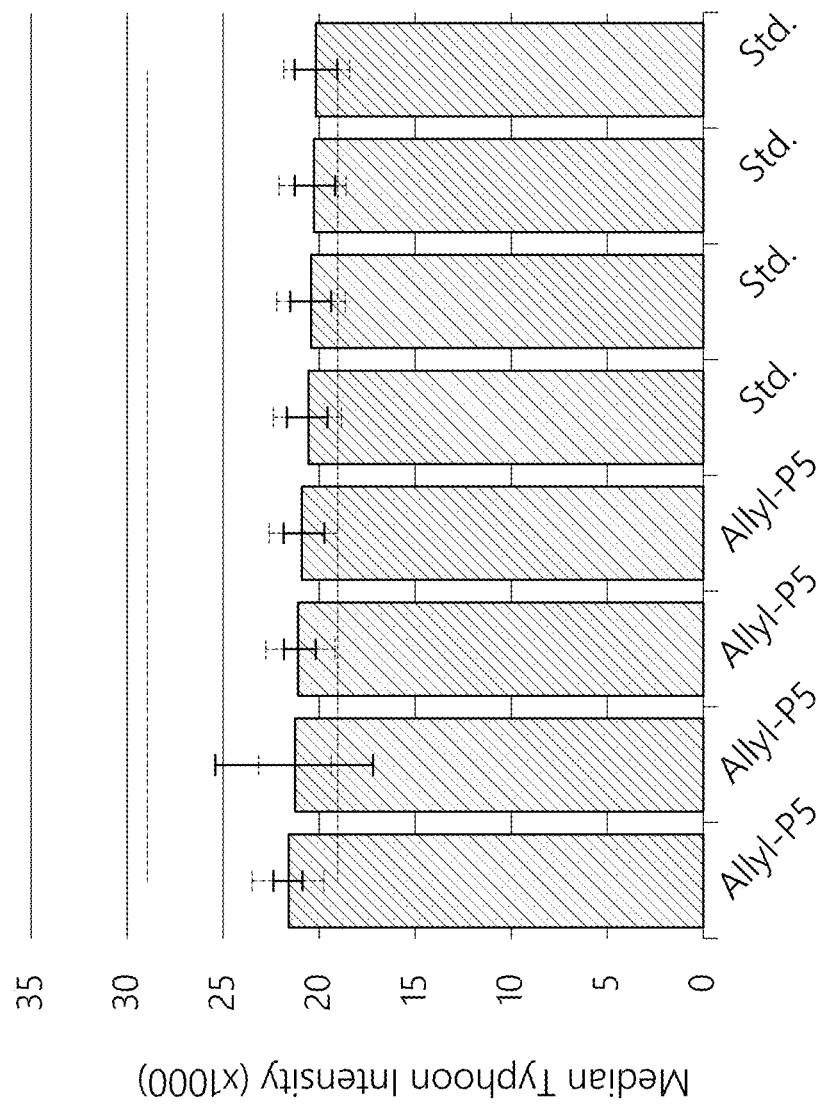
FIG. 3A is a bar chart demonstrating TET dye surface fluorescence QC assay (TET-QC) results from a non-patterned high primer density flow cell grafted with allyl modified P5 primers and standard P7 primers (Channels 1-4), as compared to flow cell grafted with standard P5/P7 primers (Channels 5-8).
Figure 3B:
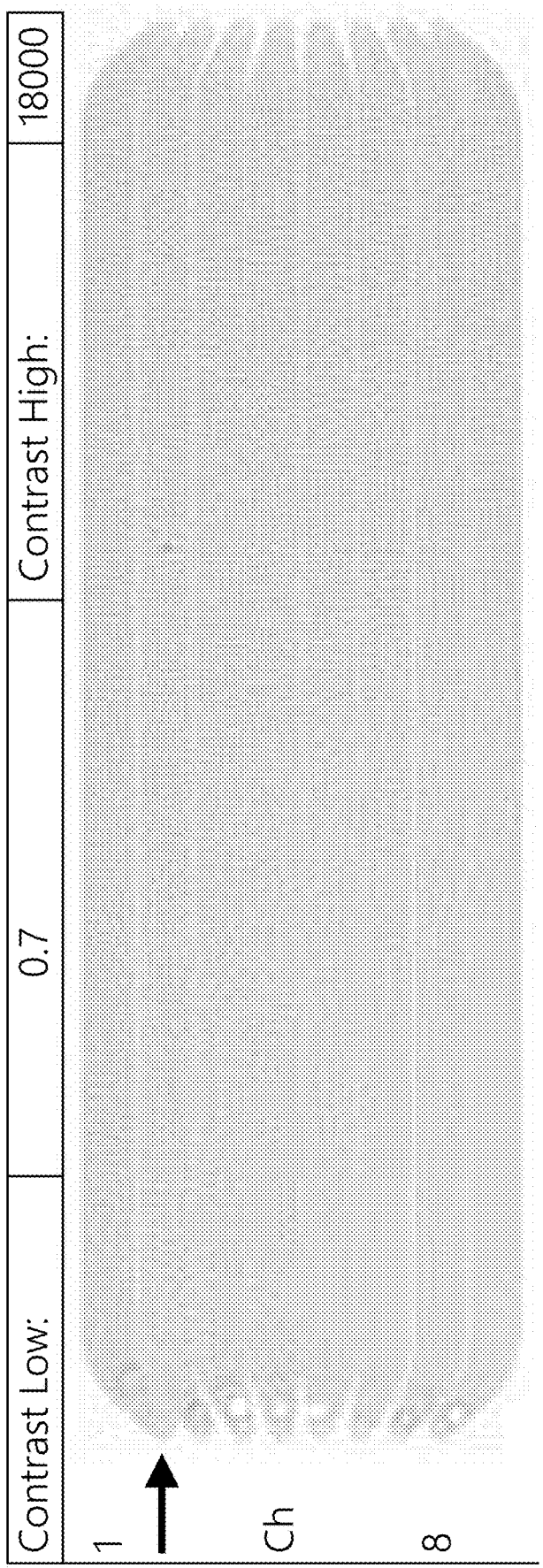
FIG. 3B illustrates the Typhoon image of the flow cell surface after the TET-QC described in FIG. 3A.

FIG. 3A is a bar chart demonstrating TET dye surface fluorescence QC assay (TET-QC) results from a non-patterned high primer density flow cell. In Channels 1-4, the surface was grafted with allyl modified P5 oligos and standard P7 oligos. In Channels 5-8, the surface was grafted with standard P5/P7 oligos. The results were comparable between the modified and the standard P5 oligos. FIG. 3B illustrates the Typhoon image of the flow cell surface after the TET-QC described in FIG. 3A. Again, no visible difference between the channels was identified as both showed no detectable signal left. The preliminary data suggested that there are no particular difference between the modified P5 oligos and the standard P5 oligos in terms of cluster density.

It was also observed that the cleavage solution containing $Na_2PdCl_4$/THP was stable when stored at room temperature for several days and aged mixes can still be used to cleave the allyl-modified P5 oligos.

Example 2

In this example, the Pd(0) linearization method and diol cleavage method described herein were tested on a new type of flow cell grafted with P15/P17 primers and sequencing data on a MiSeq® (configured as a 2-channel instrument) was collected and compared to the standard flow cell grafted with P5/P7 primers and used the enzymatic linearization described in FIG. 1. Both the new flow cell and the standard flow cell were coated with PAZAM polymer, and the primer density on the surface was aimed to be about 200K for both type of primers.

The sequencing was performed for both flow cells with NovaSeq™ incorporation mix, and imaging performed at 20° C. Before each linearization steps (Read 1 and Read 2), the flow cells were exo treated to remove any excess of unused surface primers. For the standard surface primers (P5/P7) linearization was done in Read 1 with USER enzyme (LMX1) at 38° C. for 20 min incubation and in Read 2 with FpG enzyme at 40° C. for 20 min incubation. For the new P15/P17 surface primers linearization was done in Read 1 with a Palladium mixture containing THP and sodium ascorbate (6 mM/60 mM/6 mM) at 60° C. for 2 min incubation and in Read 2 with a sodium periodate mixture at 20° C. for 10 min flush. The sequenced library presented in those data is PhiX, and the runs were 2×151 cycles. The sequencing results are summarized in the table below.

Figure 4:
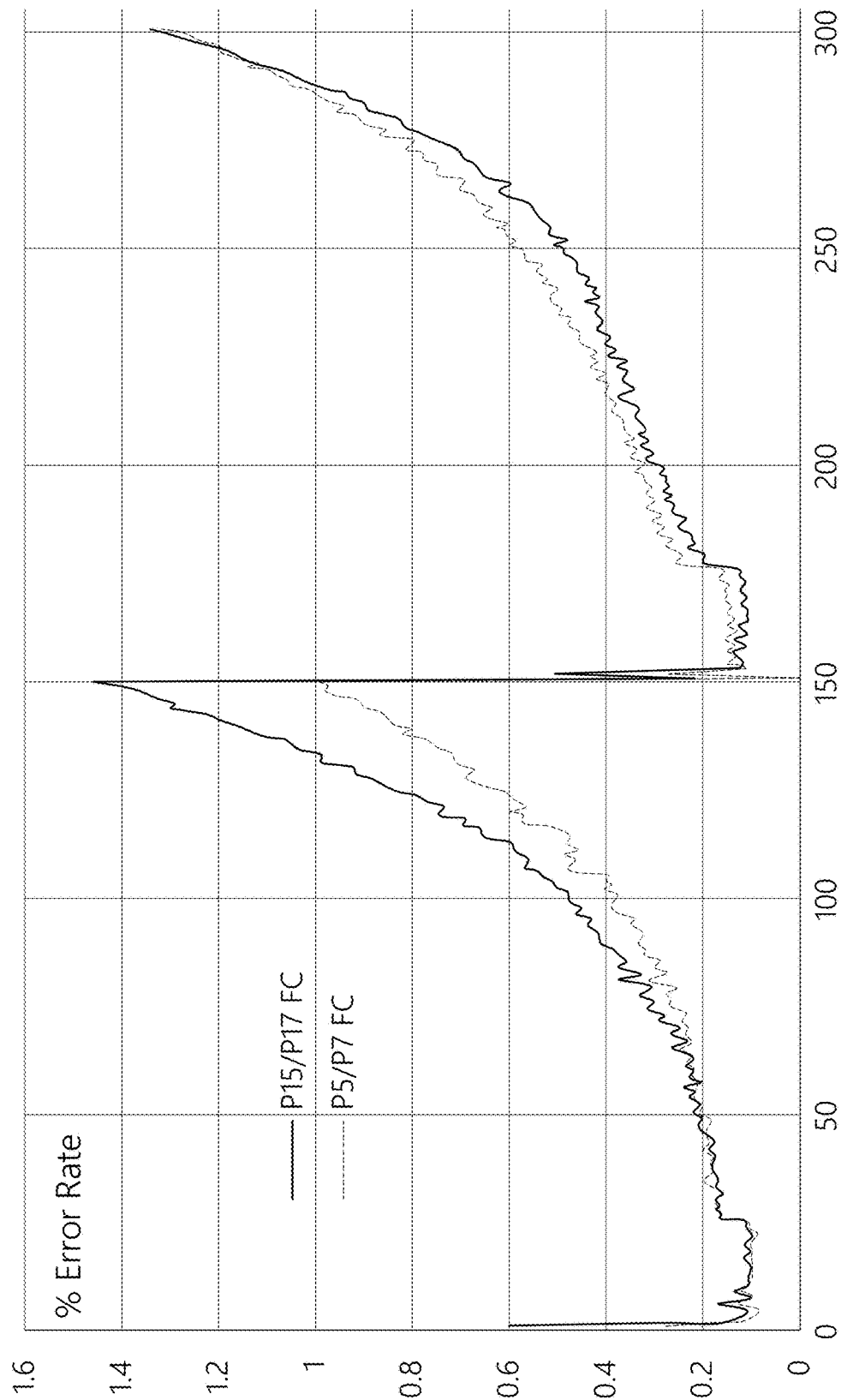
FIG. 4 illustrates the % Error Rate of the sequencing data on a Miseq® 2-channel instrument using the standard flow cell and a new type of flow cell.

The sequencing data suggests that Pd(0) assisted chemical linearization worked well in sequencing and the primary metrics are very similar as compared to the standard ones. Cluster passing filter (% PF), phasing/prephasing, % alignment are equivalent for both P5/P7 and P15/P17 surface primers. The % error was slightly higher in Read 1 for the P15/P17 grafted flow cell but was still quite good (as shown in FIG. 4) and flow cell to flow cell variation can occur as well. The % error rate in Read 2 is comparable. Furthermore, the time required for linearization decrease by 2 fold for Read 2 and by 10 fold for Read 1 when using the new type of flow cell.

Example 3

In this Example, the allyl T nucleoside described in Example 1 may be further tagged with a detectable label (i.e., a fluorescent label) to further streamline the current Illumina manufacturing workflow. Once the dye labeled allyl T nucleoside is incorporated into the P5 oligos, it enables direct quantification of the grafting reaction immediately after completion. In the current process, this step is performed as a separate hybridization assay.

The Pd(0) cleavage reaction using the dye labeled modified T nucleotide is illustrated in Scheme 3, using synthetic methods analogous to those described in the preceding examples.

Scheme 3

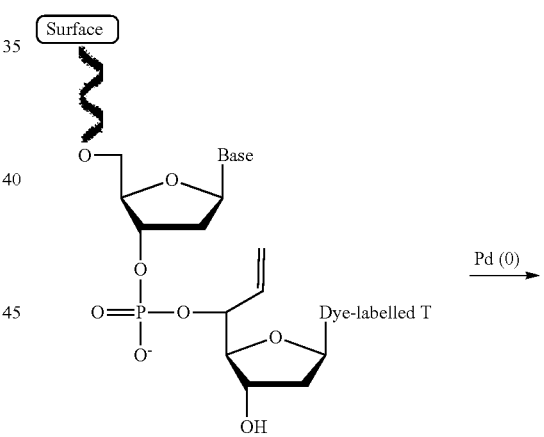

| Fc type | Density (K/mm2) | Clusters PF (%) | emp Ph/PPh R1 | Aligned (%) R1 | Error Rate (%) R1 | Intensity Cycle 1 | emp Ph/PPh R2 | Aligned (%) R2 | Error Rate (%) R2 | % resynth |
|---|---|---|---|---|---|---|---|---|---|---|
| P15/P17 FC | 183 +/− 37 | 90.57 +/− 6.86 | 0.05/0.06 | 96.24 +/− 3.75 | 0.45 +/− 0.03 | 3211 +/− 288 | 0.06/0.06 | 94.86 +/− 3.87 | 0.47 +/− 0.01 | 95.0 |
| P5/P7 FC | 237 +/− 2 | 89.37 +/− 0.40 | 0.07/0.06 | 97.86 +/− 0.08 | 0.36 +/− 0.01 | 3300 +/− 40 | 0.1/0.08 | 96.06 +/− 0.21 | 0.52 +/− 0.02 | 87 |

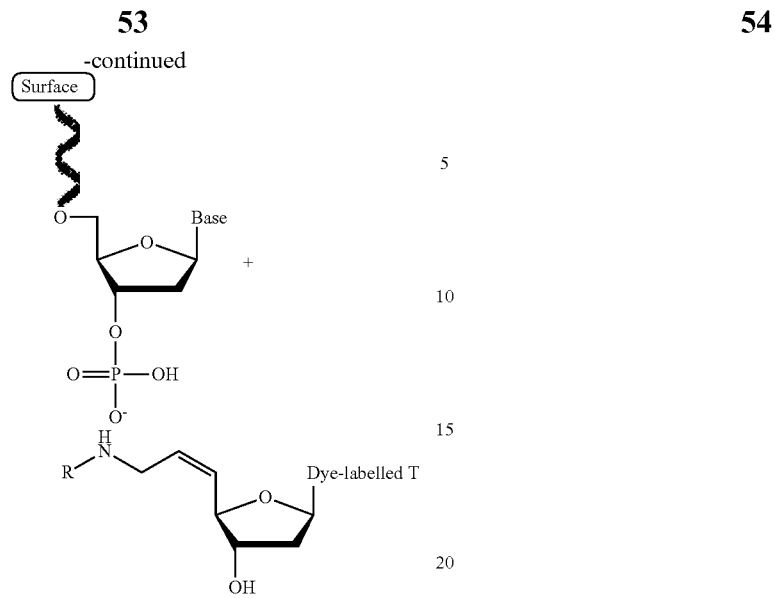
Example 4
In this Example, a diol linker reagent was prepared as shown in Scheme 4. The method improves upon the synthesis described in U.S. Pat. No. 8,715,966.

Scheme 4
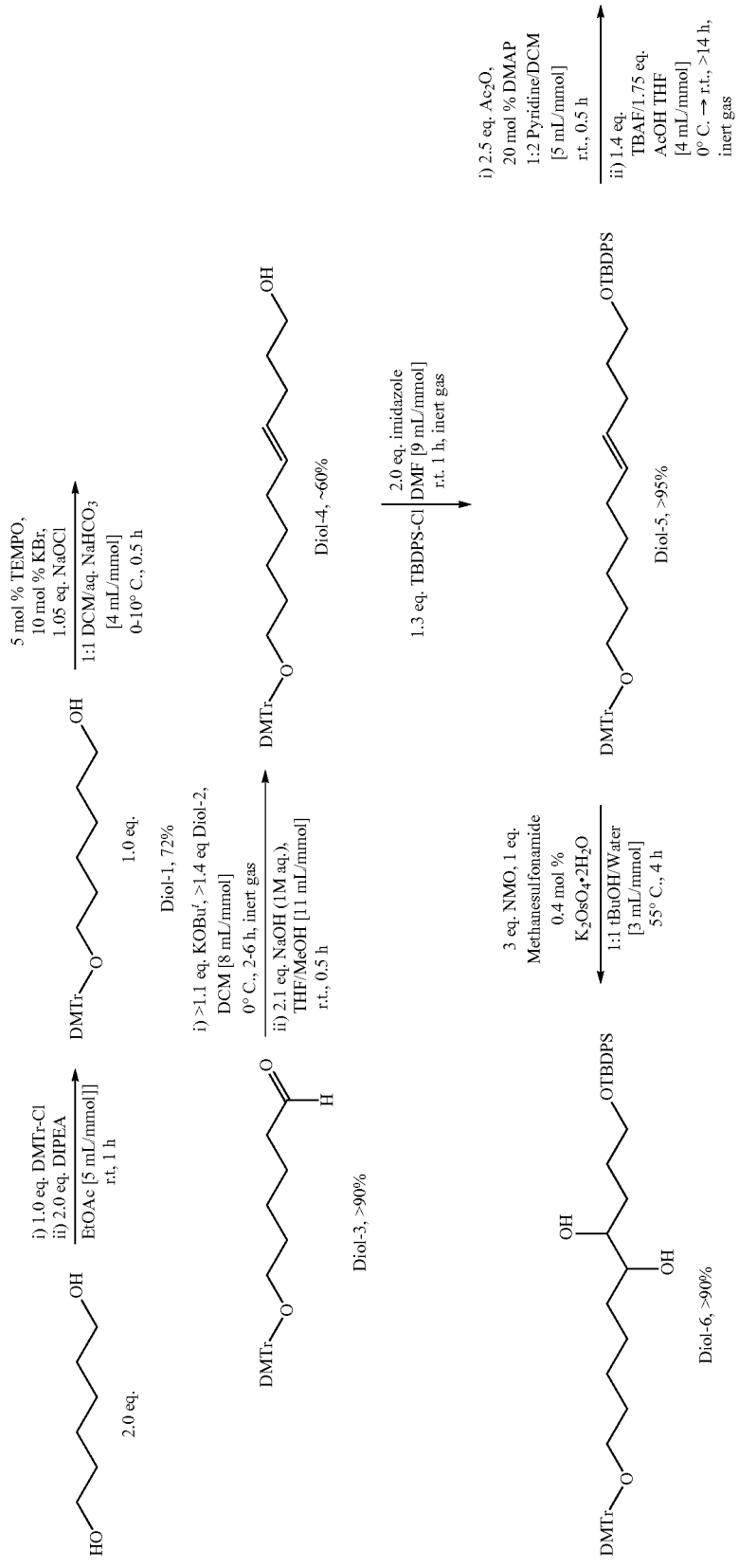

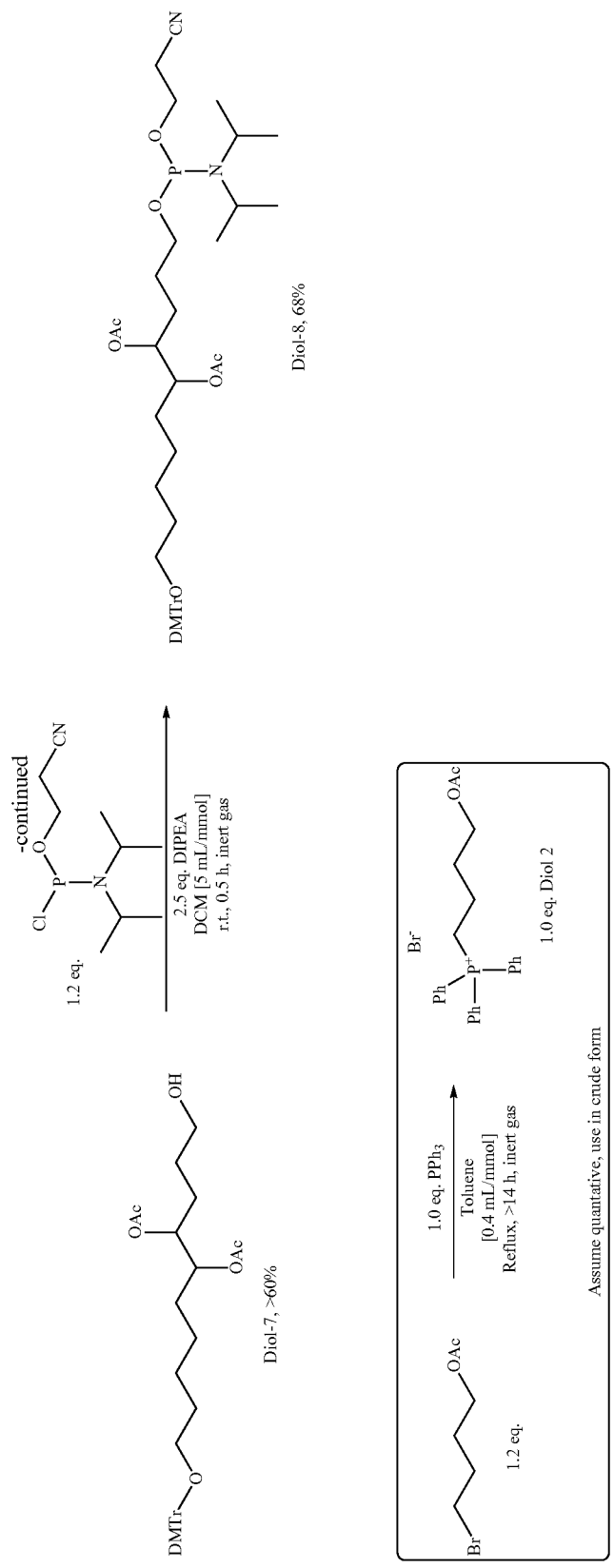

Diol-1. The present method removes DMF as a solvent in the synthesis of Diol-1. DMF complicates aqueous extractions due to formation of emulsions and undesirable partitioning of product into the aqueous phase, and in the prior-reported process, its removal before work-up was time-consuming. The prior DMF/DCM mixture was replaced with EtOAc, which reduced process time from 3 days to 1-2 days (including chromatography). In addition, the formation of the bis-tritylated side-product diminished the yield in the prior method. Changing the order of addition of reagents from the portionwise addition of solid DMTr-Cl to a mixture of hexanediol/DIPEA to the dropwise addition of liquid DIPEA to a mixture of hexanediol/DMTr-Cl improved the selectivity of the reaction for the desired product by about 10%. In some embodiments, the product of this reaction may be used crude, without chromatography to remove DMTr-OH and bis-tritylated side product.

Diol-3. The prior oxidation method using TPAP/cat. NMO led to over-oxidation to the corresponding carboxylic acid and required up to 3-4 days. Here, TPAP/NMO was replaced with TEMPO/bleach in a biphasic mixture of DCM and aq. NaHCO$_3$. The bleach was added dropwise to a mixture of the remaining reagents, and the reaction was complete once the bleach addition was done. The product was isolated by aqueous extraction, with minimal over-oxidation and yields of 66-92%, and faster overall process (1.5 days). In another embodiments, synthesis of Diol-3 and Diol-4 may be telescoped to remove the intermediate chromatography step. Excess tBuOK may be required to neutralize any carboxylic acid material in the starting material.

Diol-2. The prior method for the synthesis of Diol-2 included a 48 h reflux with some manipulations at 36 h to ensure complete reaction. Increasing the reaction concentration allowed a reduction in reflux time from 48 h to 12-24 h. In the prior protocol, crude Diol-2 was extracted into water. Removal of the water was required (as the subsequent step is moisture-sensitive), which was time-consuming on scale. The step was improved by extraction Diol-2 into DCM and washing with aq. NaHCO$_3$ to remove any acetic acid and minimize solvent removal time. The overall process time decreased from 3 days to 2 days. The product was stored as a stock solution in DCM. The solution was stored over 3 A molecular sieves overnight prior the Diol-4 reaction.

Alternatively, Diol-2 may be hydrolyzed to the corresponding alcohol to simplify purification. The alcohol would then be used in the subsequent step to provide Diol-4 directly.

Diol-5. The chromatography purification step was removed, saving 1 day in process time. In addition, DMF may be switched to DCM to improve the efficiency of the process by allowing for a decrease in solvent/wash solution volumes during aqueous work-up.

Diol-6. The chromatography purification step may be removed.

Diol-7. The synthesis of Diol-7 involves two telescoped processes, esterification and desilylation using TBAF. In the previously reported process, significant 1,4-acetyl migration was observed during desilylation with TBAF, leading to the formation of significant quantities of the undesired side-product, Diol-7M:

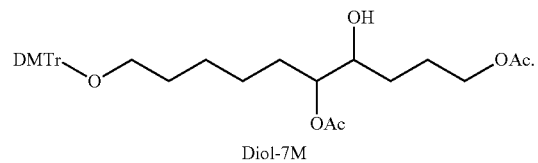

Diol-7M

This material reduced overall yields and purity of Diol-7. In addition, carry-through of Diol-7M to the subsequent step produced Diol-8M, with the phosphoramidite on the secondary rather than primary alcohol. Incorporation into a primer would result in an uncleavable linker. In the present method, the TBAF step was buffered with AcOH to remove undesired NaOH from commercial TBAF batches. Too much AcOH leads to loss of the DMTr protecting group. The reaction was run with 1.75 eq. AcOH, and pre-mixing of TBAF and AcOH prior to exposure of the starting material. In addition, the prior method included evaporation of THF before work-up; the current method removed that evaporation step, and included careful neutralization of the aqueous phase to pH 7 to reduce base-induced degradation of the product. Finally, the chromatographic purification following the esterification step has been removed.

Alternatively, the Diol-5 to Diol-7 synthetic procedures may be telescoped, eliminating additional chromatography steps. In sum, the process may be run to include three chromatography steps rather than six, and crude material would be purified at the Diol-4, Diol-7, and Diol-8 stages.

Example 5

This example describes the synthesis of A-TOM monomer, a modified 3' phosphate moiety that serves as a hydroxyl protecting group. (TOM=tri-isopropylsilyloxymethyl)

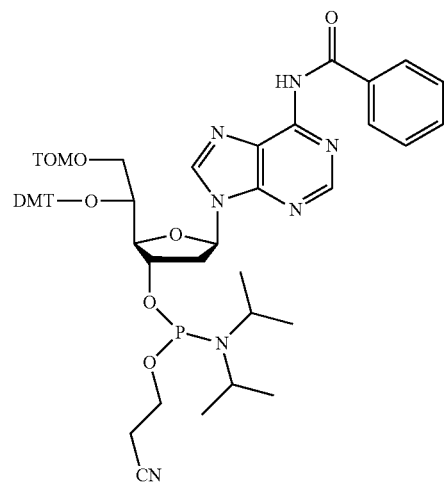

Step 1. Benzoylation of DMT Adenosine (A-OBz).

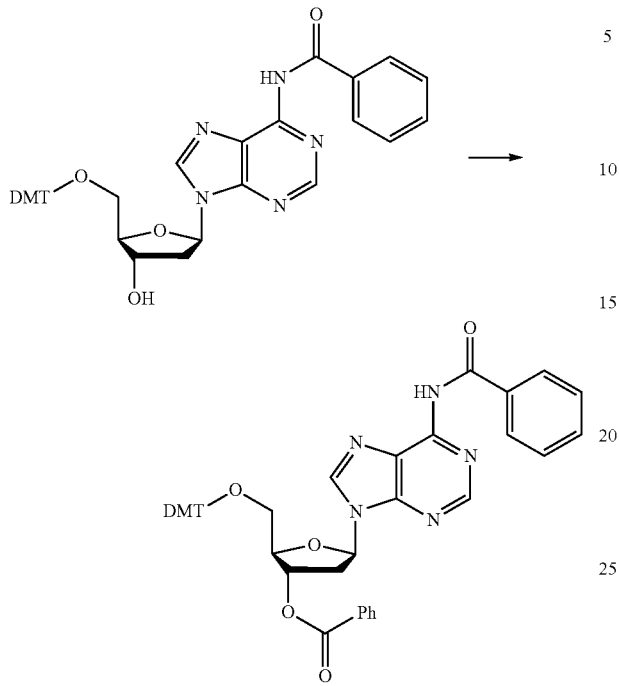

N6-Benzoyl-2'-deoxy-5'-ODMT-D-adenosine (11.2 g, 17 mmol) and solvent (pyridine/DCM mixture in 1:3 ratio, 11 ml pyridine, 33 ml DCM) were mixed at room temperature to give a solution. The reaction flask was cooled to 0° C. and to it was added DMAP (0.41 g, 3.41 mmol) and benzoyl chloride (3.9 g (3.2 ml), 34.1 mmol). Stirred while warming to room temperature overnight (TLC monitoring of reaction progress), resulting in a very pale orange mixture with some white solid precipitate. Solvent was removed in vacuo at temperature <40° C. The residue was diluted with AcOEt (~500 mL), washed twice with saturated aqueous sodium bicarbonate (2×250 mL), water (250 mL) and dried over MgSO₄. After evaporation of solvents and a co-evaporation with toluene, a white foam was obtained and dried in vacuo to a constant weight. The material was used in the next step without purification.

Step 2. Detritylation (A-OH).

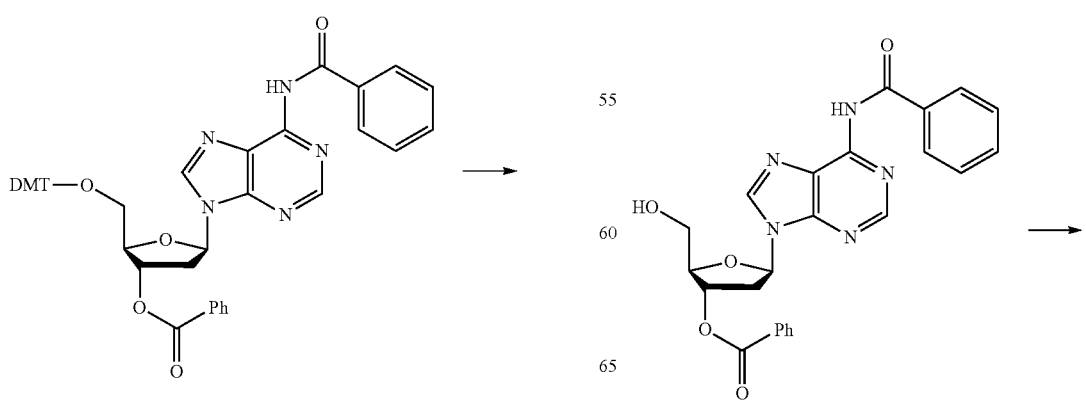

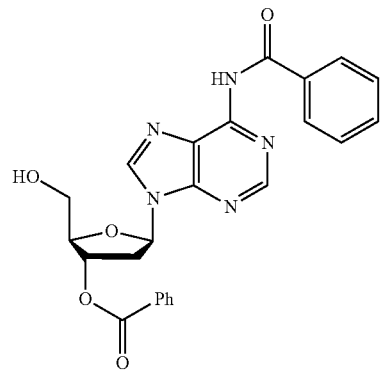

A-OBz (13.69 g, unpurified, 17 mmol) was dissolved in dichloromethane/methanol mixture (1:1, 300 ml) and cooled to 0° C. under nitrogen. Trifluoroacetic acid (2.75 ml, 36 mmol) was added via syringe. Reaction stirred while warming to room temperature for one hour. Monitored reaction progress by TLC. Reaction quenched at 0° C. by addition of solid NaHCO₃ (3 g, 36 mmol). Removed solvent in vacuo at temperature <40° C. and the residue was diluted with AcOEt (~800 mL), and washed five times with water (5×250 ml). Dried the organic layer over MgSO₄, filtered and dried in vacuo to yield a white foam. Purification by column chromatography (gradient elution with 1:1 petroleum ether/ethyl acetate to ethyl acetate) afforded the target product as a white powder. (5.0 g, 60% yield (2 steps), Rf=0.35 in 100% ethyl acetate) $^1$H NMR (400 MHz, DMSO-$d_6$) δ 11.25 (s, 1H), 8.78 (s, 1H), 8.75 (s, 1H), 8.07 (ddt, J=10.1, 7.0, 1.4 Hz, 4H), 7.75-7.68 (m, 1H), 7.68-7.62 (m, 1H), 7.62-7.51 (m, 4H), 6.64 (dd, J=8.6, 5.9 Hz, 1H), 5.68 (dt, J=6.1, 1.9 Hz, 1H), 5.28 (t, J=5.7 Hz, 1H), 4.31 (td, J=4.4, 1.8 Hz, 1H), 3.72 (tdd, J=11.8, 6.4, 4.7 Hz, 2H), 3.19 (ddd, J=14.4, 8.7, 6.1 Hz, 1H), 2.75 (ddd, J=14.1, 5.9, 1.8 Hz, 1H).

Step 3. Oxidation.

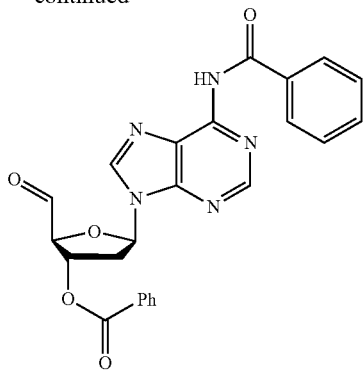

A solution of A-OH (1.0 g, 2.18 mmol) in dichloromethane (50 ml) containing molecular sieves (4 Å) was cooled to 0° C. under nitrogen gas. In a separate flask, Dess-Martin periodinane (1.11 g, 2.61 mmol) was dissolved in dichloromethane (10 ml) over molecular sieves. The Dess-Martin solution was added to A-OH and allowed to warm to room temperature. Reaction monitored by LCMS and after one hour the reaction was quenched with saturated sodium bicarbonate solution. The quenched mixture was diluted with dichloromethane (~250 ml) and washed with sodium bicarbonate solution (100 ml) and water (2×100 ml). Dried the organic layer over MgSO$_4$, filtered and dried in vacuo to yield a white foam which was used in the next step without further purification.

Step 4. Wittig Reaction (A-CH=CH$_2$).

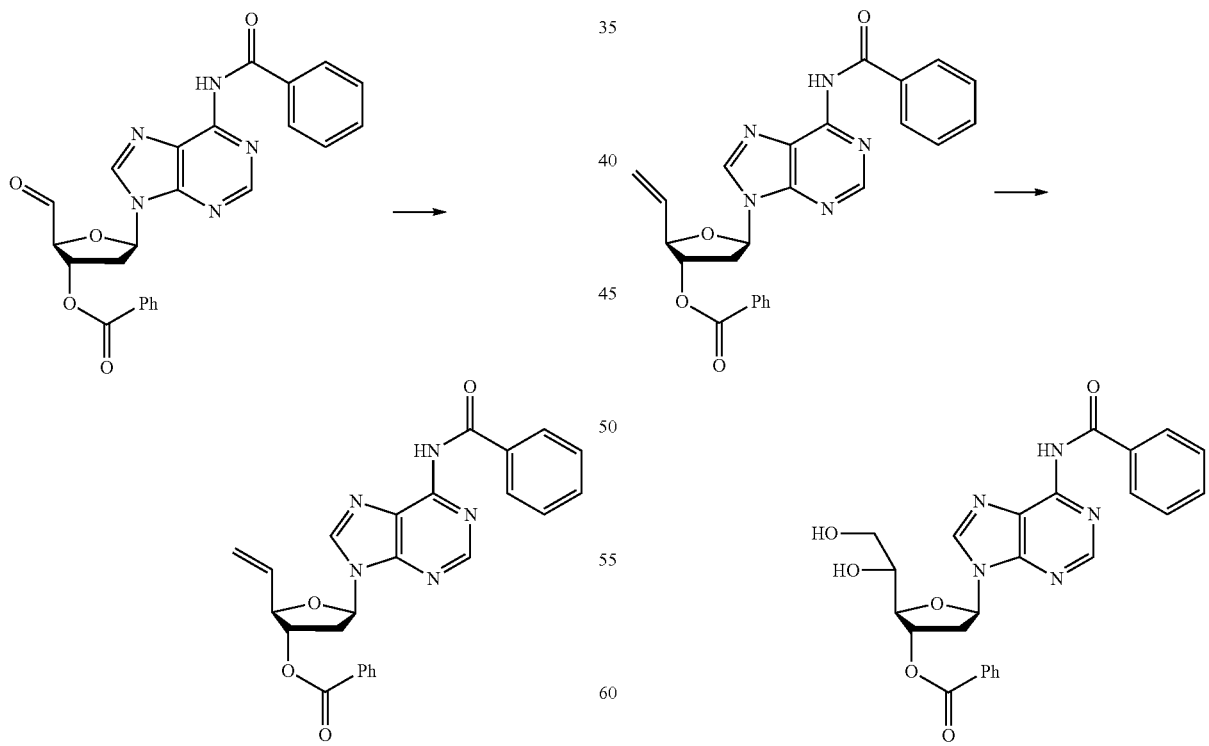

Methyltriphenylphosphonium bromide (5.83 g, 16 mmol) was mixed with dry THF (40 ml) in an oven-dried two-necked round-bottomed flask containing stir bar, molecular sieves and nitrogen line. One neck of the flask held potassium tert-butoxide in a solid addition tube. The solution was cooled to 0° C. Potassium tert-butoxide was added by turning the addition tube in the joint, allowing the solid to fall into the stirring solution without exposure to air or opening the system. Solution turns from cloudy white to yellow. Stirred at 0° C. for one hour. Note: All solid reagents for this step dried under high vacuum overnight in the presence of phosphorus pentoxide. Syringes, needles, stir bars, activated molecular sieves also dried in the same tank.

The yellow solid was added to a solution of A-CHO (2.5 g, 5.44 mmol) in THF (15 ml) at 0° C. via a wide-gauge needle and syringe. Color change from yellow to orange. Stirred at 0° C. for three hours, monitoring by LCMS.

Worked up reaction by pouring the reaction mixture into a flask containing water (300 ml) and AcOEt (300 mL) in a 1 L beaker at 0° C. Stirred for ten minutes before transferring to a separatory funnel. Washed the organic layer with saturated sodium bicarbonate solution (3×100 ml) and brine (100 ml). Dried the organic layer over MgSO$_4$, filtered and dried in vacuo to yield a brown-yellow foam. Purification by column chromatography (gradient elution with dichloromethane to 5% methanol/DCM) afforded the target product as a creamy yellow foam. (2.59 g, Rf=0.53 in 5% MeOH/DCM) $^1$H NMR (400 MHz, DMSO-d$_6$) δ 11.21 (s, 1H), 8.77 (s, 1H), 8.66 (s, 1H), 8.05 (d, J=7.2 Hz, 2H), 7.65 (t, J=7.4 Hz, 1H), 7.57 (q, J=7.9, 7.3 Hz, 3H), 6.50 (t, J=6.7 Hz, 1H), 6.06 (ddd, J=17.2, 10.4, 6.7 Hz, 1H), 5.55 (d, J=4.4 Hz, 1H), 5.29-5.10 (m, 2H), 4.42 (p, J=4.2 Hz, 1H), 4.30 (dd, J=6.7, 3.6 Hz, 1H), 2.94 (dt, J=13.1, 6.4 Hz, 1H), 2.40 (ddd, J=13.3, 6.5, 4.3 Hz, 1H).

Step 5. Diol Oxidation (A-OHOH).

A solution of A-CH$_2$CH$_2$ (0.68 g, 1.49 mmol) in THF (7 ml) was placed in a flask fitted with stir bar and under nitrogen. 4-Methylmorpholine N-oxide (0.262 g, 2.235 mmol) was weighed out as a solid and added to the reaction flask. Water (7 ml) was also added. Osmium tetroxide (4% solution in water, 285 μl, 0.045 mmol) was added to the reaction flask. The reaction was heated at 40° C. overnight. TLC and LCMS monitoring of reaction progress. Quenched reaction by adding sodium thiosulfate as a solid. Stirred the mixture for 30 minutes before workup in ethyl acetate (150 ml) and sodium bicarbonate solution. The organic layer was washed three times with saturated sodium bicarbonate solution (3×100 ml). Dried the organic layer over MgSO$_4$, filtered and dried in vacuo to yield an off-white slowly crystallizing solid. Purification by column chromatography (gradient elution with dichloromethane to 10% methanol/DCM) afforded the target product as a colorless oil. (0.13 g, 19% yield, Rf=0.28 in 5% MeOH/DCM) $^1$H NMR (400 MHz, DMSO-d$_6$) δ 11.25 (s, 1H), 8.78 (s, 1H), 8.73 (s, 1H), 8.07 (ddt, J=9.6, 7.2, 1.4 Hz, 4H), 7.74-7.68 (m, 1H), 7.68-7.62 (m, 1H), 7.62-7.47 (m, 5H), 6.62 (dd, J=8.9, 5.8 Hz, 1H), 5.82 (dt, J=5.8, 1.5 Hz, 1H), 5.48 (d, J=5.1 Hz, 1H), 4.69 (t, J=5.5 Hz, 1H), 4.31 (dd, J=5.0, 1.5 Hz, 1H), 3.81 (p, J=5.3 Hz, 1H), 3.48 (dh, J=22.3, 5.5 Hz, 2H), 3.18 (ddd, J=14.4, 9.0, 5.9 Hz, 1H), 2.70 (ddd, J=14.4, 6.0, 1.5 Hz, 1H).

Step 6. Silylation (A-OHTOM).

A solution of A-OHOH (0.128 g, 0.262 mmol) in DCM was dissolved in DCM (1.5 ml) in a flask containing stir bar and nitrogen line. Di-tert-butyltin dichloride (80 mg, 0.262 mmol) and N,N-diisopropylethylamine (182 μl, 1.05 mmol) were added at room temperature for 30 minutes. Tri-isopropylsilyloxymethyl chloride (TOM-Cl, 79 μl, 0.341 mmol) was added via micropipette. TLC and LCMS monitoring of reaction progress. Reaction left overnight at room temperature. Reaction workup carried out in ethyl acetate (200 ml). Washed with saturated sodium bicarbonate solution (3×100 ml). Dried the organic layer over MgSO$_4$, filtered and dried in vacuo to yield a yellow/brown oil. Purification by column chromatography (gradient elution with dichloromethane to 8% methanol/DCM) afforded the target product as a yellow-white foam (0.14 g, 79% yield, Rf=0.5 in 5% MeOH/DCM) $^1$H NMR (400 MHz, DMSO-d$_6$) δ 11.25 (s, 1H), 8.76 (s, 1H), 8.73-8.65 (m, 1H), 8.06 (tt, J=7.5, 1.4 Hz, 4H), 7.76-7.62 (m, 2H), 7.62-7.46 (m, 4H), 6.61 (dd, J=8.9, 5.7 Hz, 1H), 5.82 (d, J=5.7 Hz, 1H), 5.65 (d, J=5.3 Hz, 1H), 4.84 (s, 2H), 4.27 (dd, J=5.4, 1.5 Hz, 1H), 4.06-3.93 (m, 1H), 3.62 (ddd, J=42.1, 10.3, 5.2 Hz, 2H), 3.22 (ddd, J=14.7, 9.1, 5.8 Hz, 1H), 2.74-2.65 (m, 1H), 0.94 (m, 21H, TOM).

Step 7. Tritylation (A-TOM-DMT).

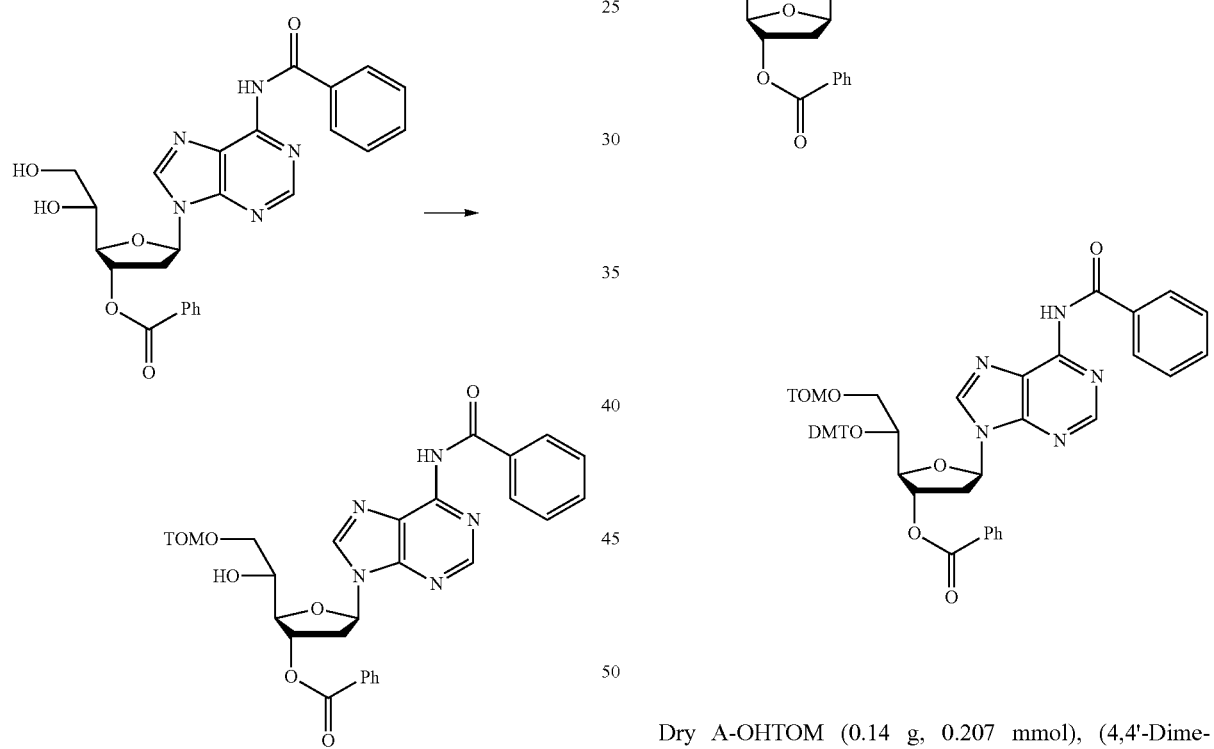

Dry A-OHTOM (0.14 g, 0.207 mmol), (4,4'-Dimethoxytriphenylmethyl chloride (DMT-Cl, 0.105 g, 0.311 mmol) and silver nitrate (53 mg, 0.311 mmol) were placed in a flask with dry DCM (1.5 ml) and collidine (2,4,6-trimethylpyridine) (55 μl, 0.414 mmol). Reaction stirred at room temperature for three hours. TLC and LCMS monitoring of reaction progress. Diluted reaction mixture with DCM (100 ml) and filtered through a sintered glass funnel. The DCM solution was washed with saturated sodium bicarbonate solution (5×100 ml). Dried the DCM layer over MgSO$_4$, filtered and dried in vacuo to yield a yellow/brown oil. Purification by column chromatography (gradient elution with dichloromethane to 10% methanol/DCM) afforded the target product as a viscous yellow oil (0.17 g, 85% yield, Rf=0.46 in 5% MeOH/DCM).

Step 8 (A-3'OH).

Step 9. Phosphoramidite Formation (ATOM Monomer).

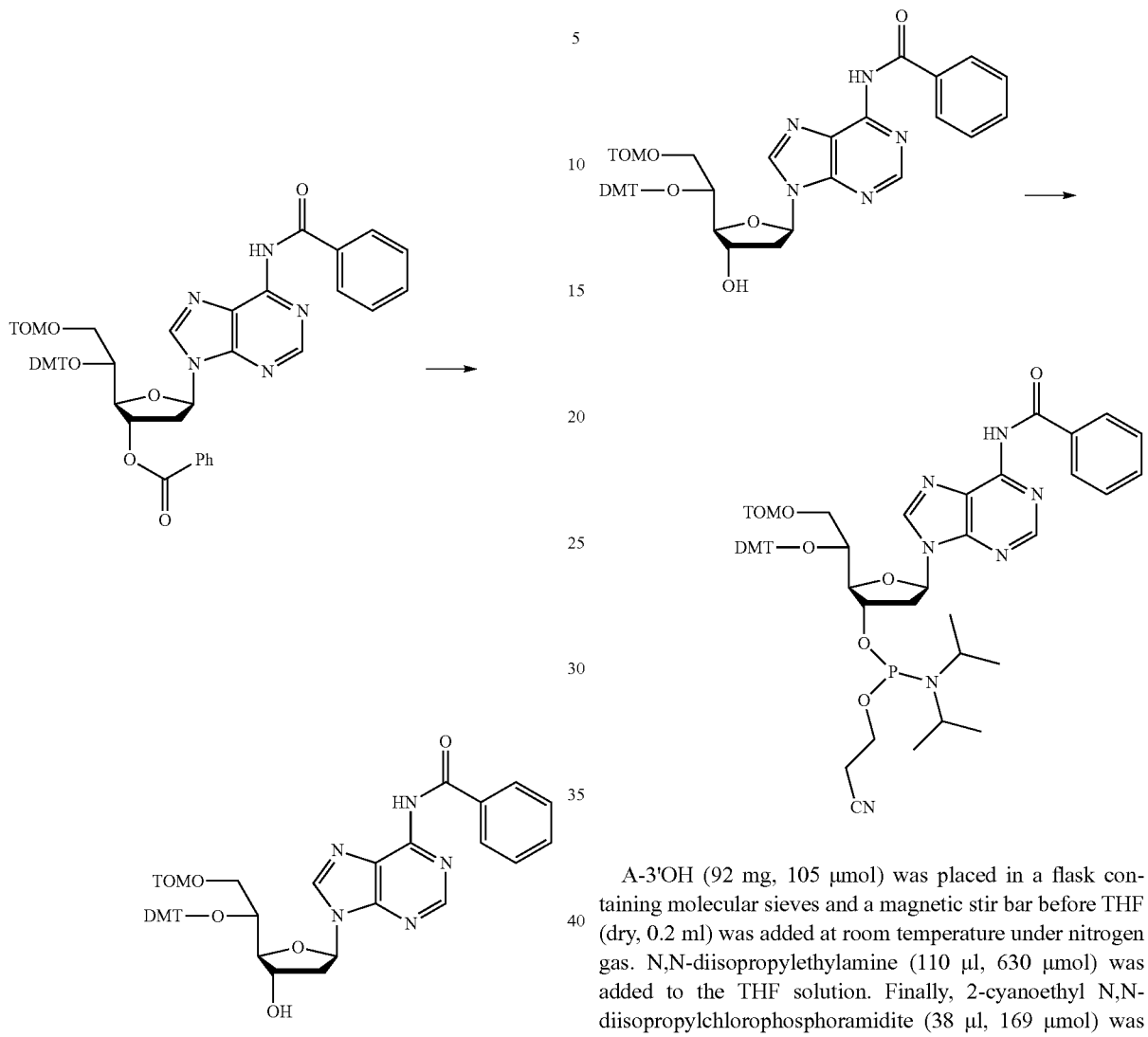

A solution of A-TOM-DMT (56 mg, 56 µmol) in a mixture of methanol and THF (4:5, 0.9 ml total) was cooled to 0° C. Added sodium hydroxide (4M, 0.1 ml, excess) and stirred at 0° C. for 15 minutes. Monitored reaction by TLC and LCMS. The reaction was quenched using acetic acid (1M, 0.5 ml), ensuring pH does not go below pH8. Diluted reaction mixture with ethyl acetate (EA, 100 ml) and washed the solution with saturated sodium bicarbonate solution (3×50 ml). Dried the EA layer over MgSO$_4$, filtered and dried in vacuo. The residue was purified by column chromatography (gradient elution with EA/petroleum ether (25%) to 100% EA) to give a white foam (0.02 g, 40% yield, Rf=0.38 in 100% EA).

A-3'OH (92 mg, 105 µmol) was placed in a flask containing molecular sieves and a magnetic stir bar before THF (dry, 0.2 ml) was added at room temperature under nitrogen gas. N,N-diisopropylethylamine (110 µl, 630 µmol) was added to the THF solution. Finally, 2-cyanoethyl N,N-diisopropylchlorophosphoramidite (38 µl, 169 µmol) was added via micropipette. Reaction stirred at room temperature under nitrogen. Reaction was monitored by TLC. When the reaction was complete, solvent was removed in vacuo. The residue was washed with petroleum ether (3×20 ml) at room temperature. The residue was then dissolved in DCM and filtered to remove the molecular sieves. Dried in vacuo again before purification by column chromatography (gradient elution with EA/petroleum ether (20%) to 75% EA) provided a viscous colorless oil (80 mg, 70% yield) $^1$H NMR (400 MHz, DMSO-d$_6$) δ 11.17 (s, 1H), 8.57 (s, 1H), 8.39 (s, 1H), 8.06-7.99 (m, 2H), 7.64 (td, J=7.1, 1.2 Hz, 1H), 7.58-7.46 (m, 4H), 7.36 (ddd, J=15.4, 9.0, 2.8 Hz, 4H), 7.29 (t, J=7.4 Hz, 2H), 7.27-7.17 (m, 1H), 6.92-6.83 (m, 4H), 6.34 (dd, J=9.0, 5.9 Hz, 1H), 4.78-4.71 (m, 1H), 4.68 (q, J=6.6, 4.6 Hz, 1H), 4.52 (dd, J=8.5, 4.9 Hz, 1H), 4.27 (d, J=7.1 Hz, 1H), 3.85-3.69 (m, 8H), 3.62 (dp, J=10.4, 6.7 Hz, 1H), 3.34-3.22 (m, 1H), 2.78 (td, J=5.8, 1.9 Hz, 2H), 2.64 (td, J=8.8, 4.7 Hz, 1H), 2.26-2.16 (m, 1H), 2.08 (d, J=0.7 Hz, 6H), 1.21 (dd, J=15.4, 5.6 Hz, 9H), 1.12 (d, J=6.7 Hz, 6H), 0.99-0.88 (m, 2H), 0.83 (dd, J=6.3, 4.5 Hz, 18H).

Example 6

Synthesis of Model Dinucleotide (C-Tom-A).

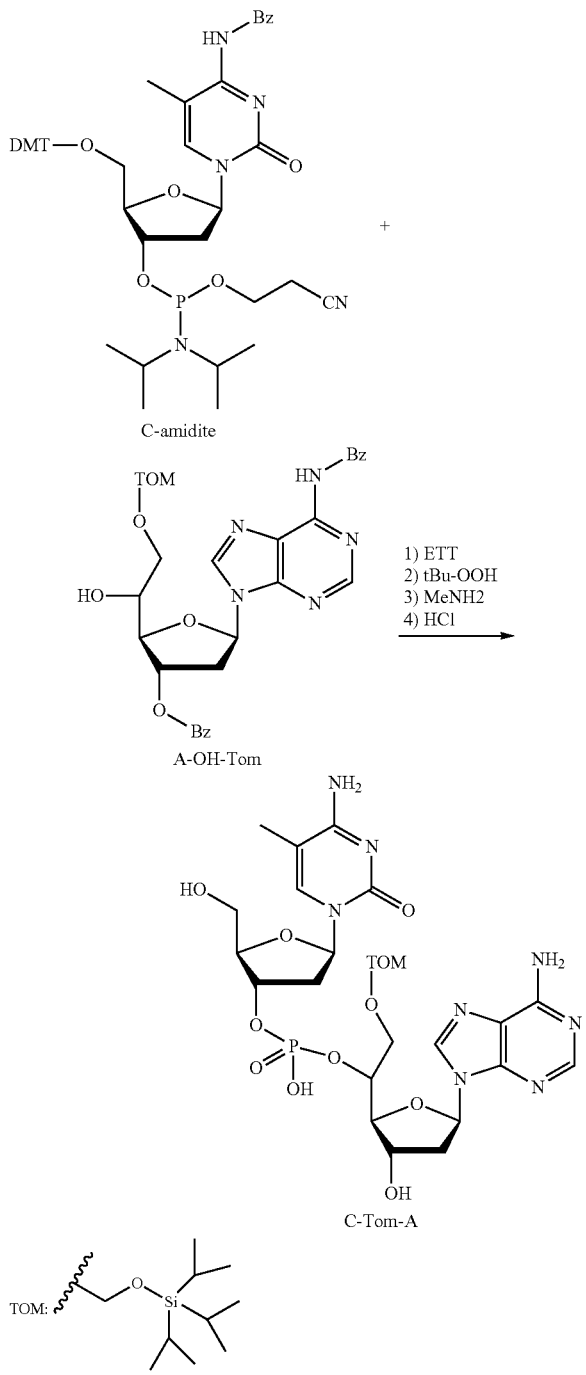

Compounds C-amidite (125 mg, 0.15 mmol) and A-OH-Tom (64 mg, 0.1 mmol) were dried over $P_2O_5$ under the vacuum overnight and dissolved in anhydrous acetonitrile (1 ml). Under $N_2$, ethylthiotetrazole (ETT, 32.5 mg, 0.25 mmol) was added. The mixture was stirred at rt for 15 min. TLC and LC-MS indicated complete consume of starting material A-OH-Tom. The solution of t-BuOOH in decan (5 M, 0.1 ml) and DCM (1 ml) was added to the reaction mixture and stirred for 15 min at rt. The reaction mixture was poured into aq. $NaHCO_3$ and aq. phase extracted with EtOAc. The combined organic phase was evaporated down and treated with NaOH (0.1 M, 1 ml in $H_2O$/THF/MeOH=1/4/5 v/v) at rt for 1 h. The mixture was then treated with HCl (1 M) in THF/MeOH (5 ml/4 ml) for 0.5 h. The reaction mixture was concentrated down and partition in $H_2O$ and EtOAc. The desired product was recovered from the aq. phase and further purified with RP HPLC (TEAB 0.1M/$CH_3CN$).

Cleavage Study on Model Compound C-TOM-A.

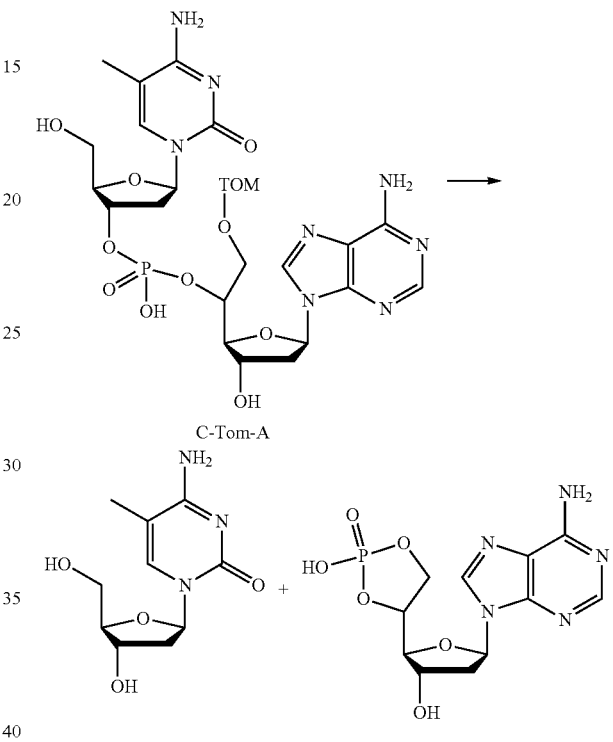

A stock solution of C-TOM-A was treated under various deprotection conditions. The reaction progress was monitored by RP HPLC. Intermediate C-A is the compound in which the TOM group has been removed from C-TOM-A, but the phosphate bond has not been cleaved. Table 1 below summarizes the deprotection results under various reaction condition and deprotection reagents.

TABLE 1

| Conditions | Results |
| --- | --- |
| 0.5 mM C-TOM-A, 0.5M TBAF, 1:1 THF/$H_2O$, pH ~7 | 60% interm. C-A/2.5 h |
| 0.5 mM C-TOM-A, 0.5M $Et_3N$—3HF, $Et_3N$, pH ~7 | 100% interm. C-A/2.5 h |
| 0.5 mM C-TOM-A, 0.25M $NH_4F$, pH ~7 | 80% interm. C-A/2.5 h |
| 0.5 mM C-TOM-A, 0.25M CsF, Tris-HCl, pH 7.4 | 70% interm. C-A/2.5 h |
| 0.5 mM C-TOM-A, 0.25M CsF, Tris-HCl, pH 9 | 70% interm. C-A/2.5 h |
| 0.5 mM C-TOM-A, 0.5M $Et_3N$—3HF, pH ~1 | 80% interm. C-A + 20% prod/1 h |
| 0.33 mM C-TOM-A, 0.17M $NH_4F$, 0.33M NaOH, pH ~14 | 50% interm. C-A + 50% prod/1 h |
| 0.33 mM C-TOM-A, 0.33M CsF, 0.33M NaOH, pH ~14 | completed at 1 h |
| 0.5 mM C-TOM-A, 1M NaOH, pH 14 | completed at 20 min |

Example 7

In this example, alternative methods to generate Pd(0) complex are described and their chemical cleavage activities were compared to the in situ generated Pd(0) complex from allyl palladium(II) chloride dimer $(Pd(C_3H_5)Cl)_2$ and THP as described in Example 1. In contrast to an in situ generated Pd(0) complex, some palladium (II) pre-catalysts were prepared and isolated prior to use in the chemical linearization reaction, for example, chemical cleavage of P15 primer. These Pd(II) pre-catalysts are inactive in the isolated form but can be conveniently reduced to the active Pd(0) in situ in presence of THP. These alternative Pd pre-catalysts may improve product stability and longer shelf life.

Preparation Method $(Pd(C_3H_5)Cl)_2$ was dissolved in dry, degassed tetrahydrofuran under nitrogen and treated with 1 to 10 equivalents of THP added as a tetrahydrofuran solution. Oiling out was observed and the oils were isolated by decanting the supernatant. The material was dried under vacuum to obtain yellow-to-brown or orange viscous oils. These materials were highly soluble in water. When 1 to 2 equivalents of THP were added, a mixture of $[Pd(C_3H_5)(THP)]Cl$ and $[Pd(C_3H_5)(THP)_2]Cl$ was isolated, both of which are Pd(II) complexes. When 5 equivalents THP was added, a clean sample of $[Pd(C_3H_5)(THP)_2]Cl$ was obtained. These two Pd(II) complexes were isolated and characterized. When 10 equivalents THP was added, Pd(0) material that is active for P15 linearization was obtained.

$[Pd(C_3H_5)(THP)]Cl$: $^{31}P$ NMR (162 MHz, D2O): d 14 (s) ppm. $^{13}C$ NMR (101 MHz, $D_2O$): d 118.7 (d, J=5.0 Hz), 81.7 (d, J=29 Hz), 62.1 (d, J=15 Hz), 26.5 (s), 20.5 (d, J=25.0 Hz) ppm. LC-MS: [AllylPd(THP)]+; Expected: 355 Da, Found: 355 Da.

$[Pd(C_3H_5)(THP)_2]Cl$: $^{31}P$ NMR (162 MHz, D2O): d 10 (s) ppm. $^{13}C$ NMR (101 MHz, $D_2O$): d 122.7 (t, J=5.3 Hz), 71.2 (t, J=14 Hz), 61.8 (t, J=7.6 Hz), 26.7 (s), 22.1 (t, J=13 Hz) ppm. LC-MS: [AllylPd(THP)_2]+; Expected: 563 Da, Found: 563 Da.

Use for P15 Cleavage

Materials isolated from treatment of $(Pd(C_3H_5)Cl)_2$ with 1, 2, 5, and 10 equivalents THP were formulated in aqueous buffer at 10 mg/mL. The activity of these formulations towards P15 cleavage was assessed using a HPLC-based assay. In this assay, a solution of P15 primer (10 µM) was treated with 10% v/v of each formulation, incubated for 10 minutes at 38° C., then quenched by dilution and spin column treatment and analyzed by HPLC. Percentage cleavage is calculated from the ratio of the P15 and cleavage product peak areas.

Figure 5A:
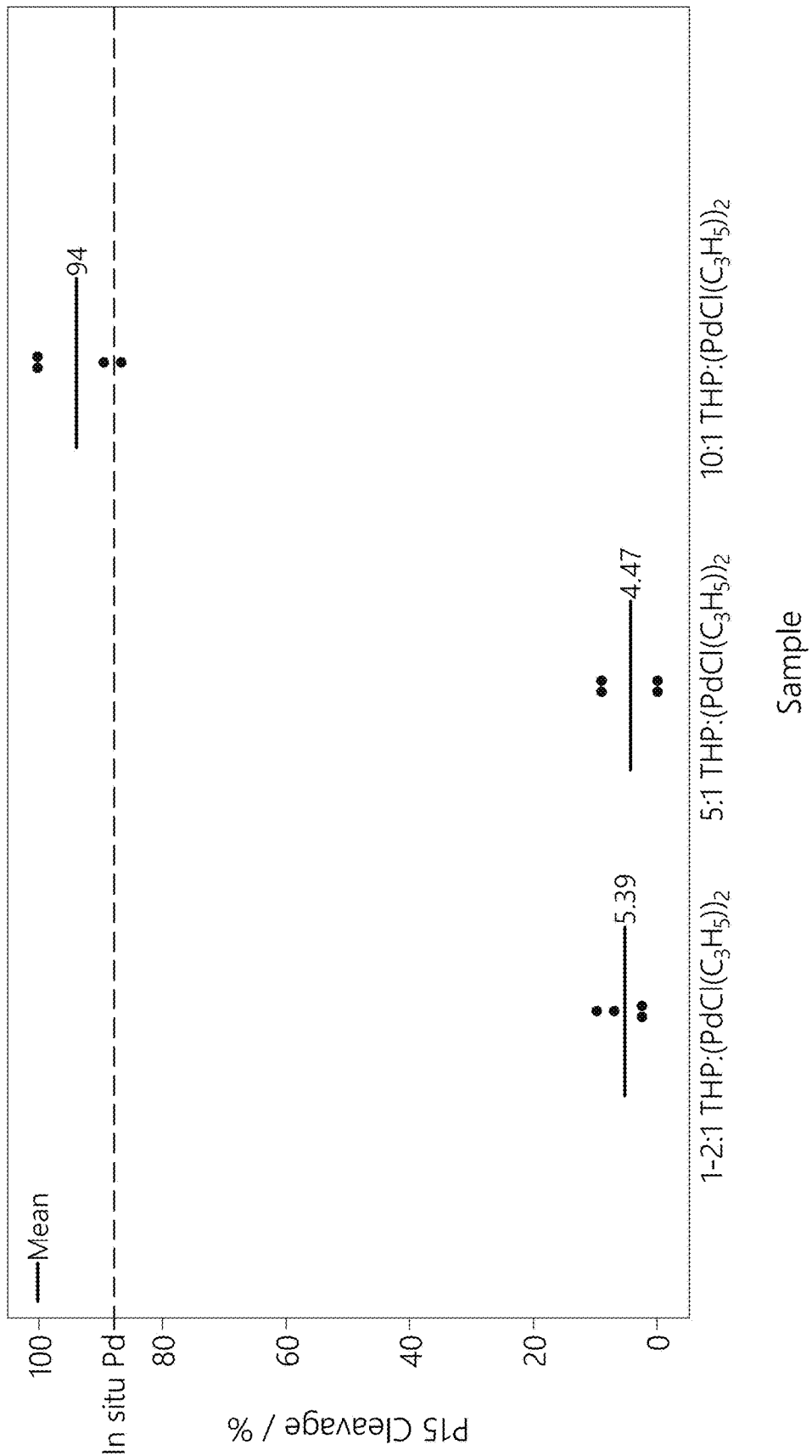
FIG. 5A illustrates the P15 cleavage activities of formulations isolated from Pd(C$_3$H$_5$)Cl)$_2$ in presence with 1 to 10 equivalents THP (10 mg/mL, N=4 for each condition) compared to a formulation of (Pd(C$_3$H$_5$)Cl)$_2$ (6 mM), THP (60 mM), and sodium ascorbate (6 mM) (N=2).
Figure 5B:
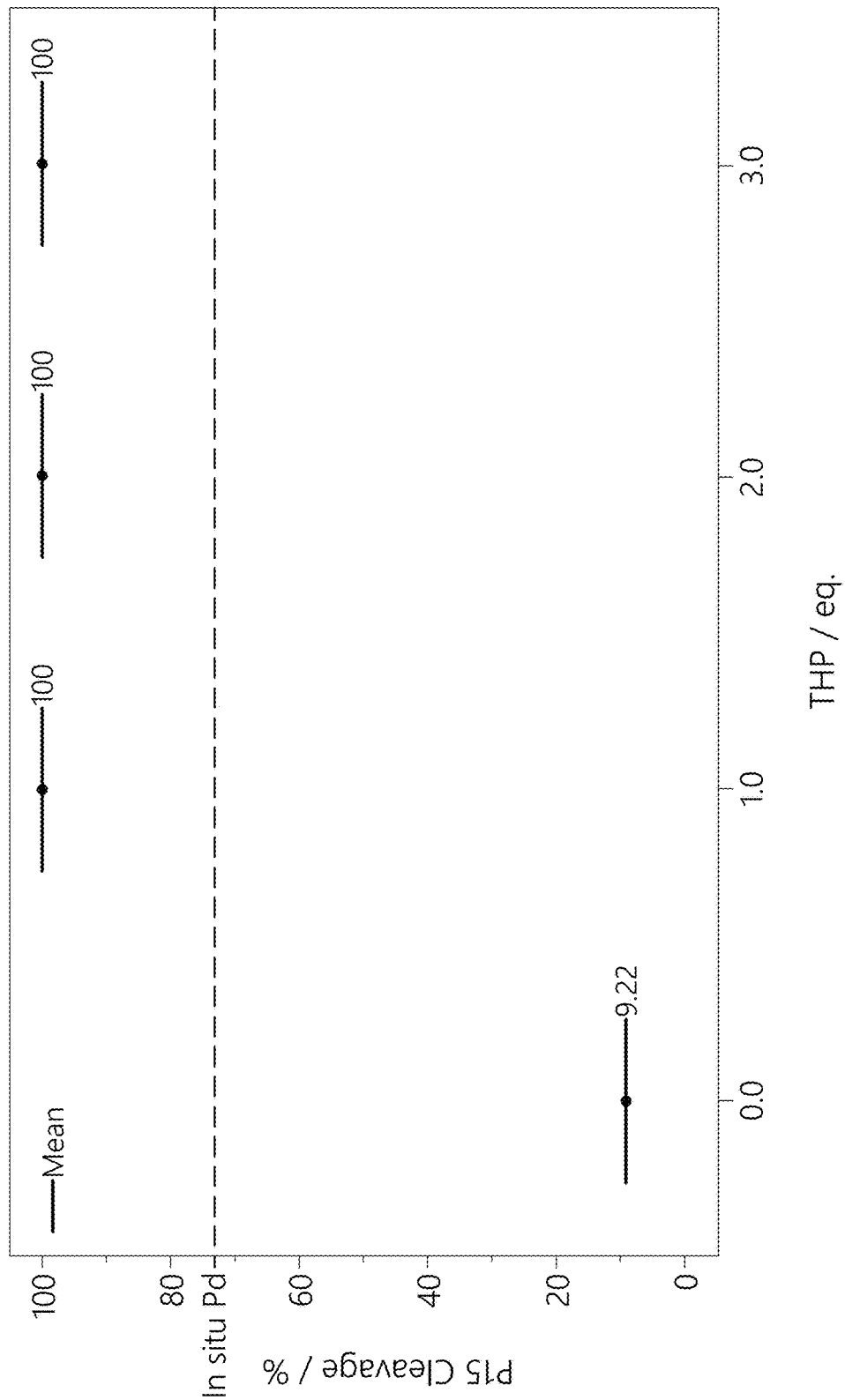
FIG. 5B illustrates the P15 cleavage activities of a formulation containing [Pd(C$_3$H$_5$) (THP)$_2$]Cl and 1 or more equivalents THP (12 mM Pd, N=2 for each condition) compared to a formulation of (Pd(C$_3$H$_5$)Cl)$_2$ (6 mM), THP (60 mM), and sodium ascorbate (6 mM) (N=2).

Aqueous formulations of $[Pd(C_3H_5)(THP)]Cl$ and $[Pd(C_3H_5)(THP)_2]Cl$ (obtained from mixing $(Pd(C_3H_5)Cl)_2$ with 1 to 5 equivalents THP) were inactive for P15 cleavage in absence of other additives. However, aqueous formulations of material isolated from mixing $(Pd(C_3H_5)Cl)_2$ with 10 equivalents THP provided comparable P15 cleavage activity to a Pd mixture prepared in situ from $(Pd(C_3H_5)Cl)_2$ (6 mM), THP (60 mM), and sodium ascorbate (6 mM). The results were shown in FIG. 5A. It was observed that Pd(II) pre-catalysts $[Pd(C_3H_5)(THP)]Cl$ and $[Pd(C_3H_5)(THP)_2]Cl$ were conveniently activated in situ either during preparation or at their point of use by treatment with additional aqueous THP solution. $[Pd(C_3H_5)(THP)_2]Cl$ was demonstrated to become active when treated with 1 or more equivalents THP when formulated in aqueous solution (12 mM Pd). P15 cleavage performance exceeded the point of reference sample a Pd(0) mixture prepared in situ from a mixture of $(Pd(C_3H_5)Cl)_2$ (6 mM), THP (60 mM), and sodium ascorbate (6 mM) (FIG. 5B).

Example 8

In this example, an alternative isolatable Pd(0) complex $Pd(THM)_4$ was prepared by using a phosphine ligand tris (hydroxymethyl)phosphine (THM). Its cleavage activity was compared to the in situ generated Pd(0) complex from allyl palladium(II) chloride dimer $(Pd(C_3H_5)Cl)_2$ and THP as described in Example 1.

Preparation: $Pd(THM)_4$ was prepared and isolated using the protocol described by Ellis, et al., *Inorg. Chem.*, 1992, 31, 14. An aqueous solution was formulated at 10 mM concentration and its performance was assessed relative to the Pd(0) generated in situ using $(Pd(C_3H_5)Cl)_2$ (10 mM) and THP (100 mM).

Figure 6A:
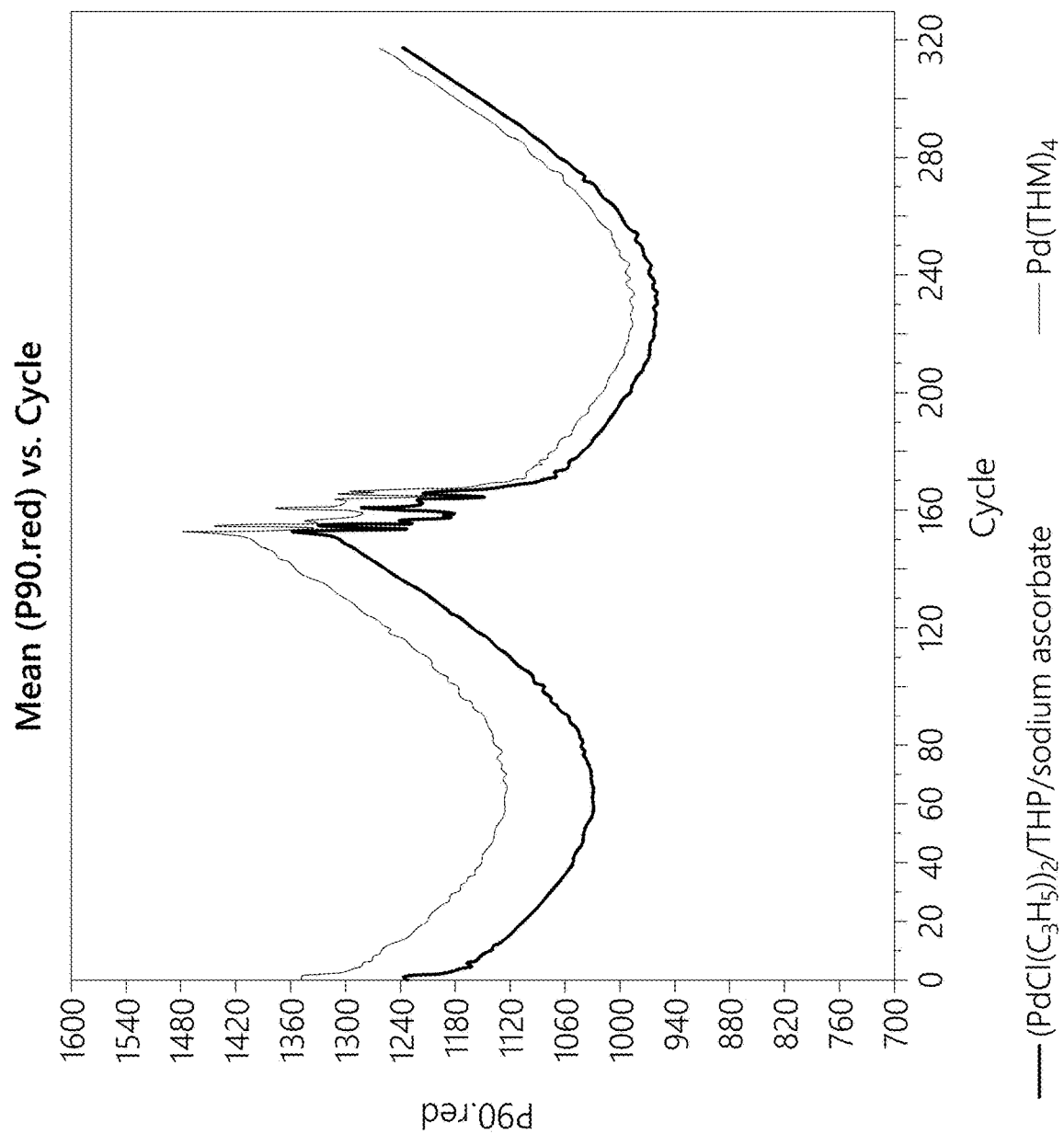
FIG. 6A shows NovaSeq™ mean read 1 intensities for 10 mM Pd(THM)$_4$ compared to a Pd(0) reagent generated in situ.
Figure 6B:
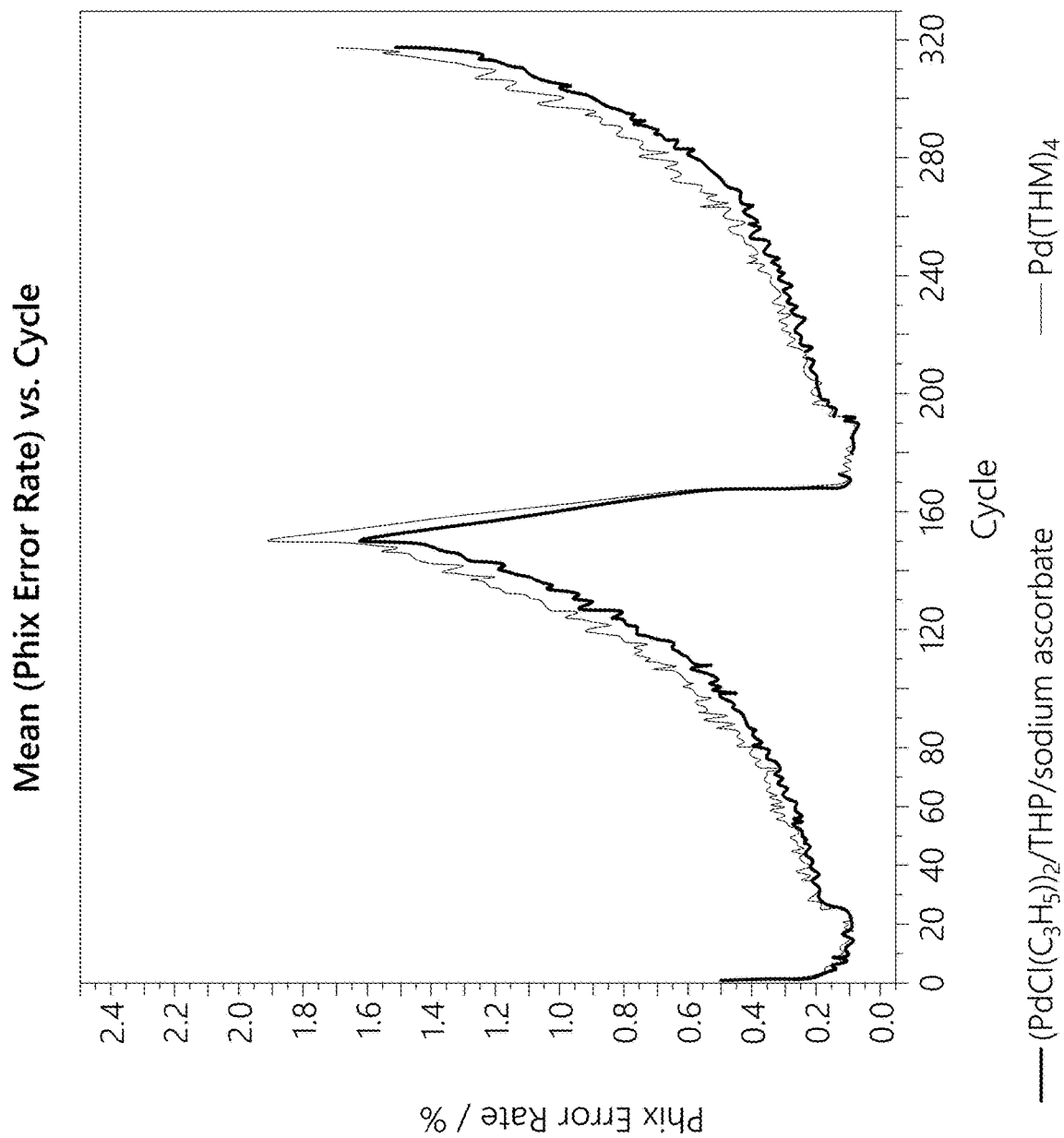
FIG. 6B shows NovaSeq™ mean PhiX error rate for 10 mM Pd(THM)$_4$ compared to a Pd(0) reagent generated in situ.

To demonstrate Pd(0)-induced linearization, sequencing was performed on a NovaSeq™ instrument using an S4 flow cell grafted with P15/P7 surface primers (2×151 with dual indexing cycles). The Xp workflow was used with nano (lanes 1 and 3) and PCR-free (lanes 2 and 4) libraries (450 bp inserts). Prior to read 1 SBS chemistry, linearization was performed using either a Pd mixture composed of $(Pd(C_3H_5))Cl)_2$ (10 mM), THP (100 mM), and sodium ascorbate (10 mM) [in lanes 1-2]; or an aqueous solution of $Pd(THM)_4$ (10 mM) [in lanes 3-4]. Read 2 linearization was performed using a reagent containing the FpG enzyme. It was observed that sequencing metrics were generally comparable for both Pd linearization methods. The high read 1 intensities and percentage resynthesis with $Pd(THM)_4$ indicated that successful linearization was achieved (FIG. 6A). Human and PhiX error rates were comparable for both methods (FIG. 6B). The sequencing results are summarized in the table below (Table 2).

TABLE 2

| Metric | $(PdCl(C_3H_5))_2$/THP/ sodium ascorbate Mean ± Std Dev | $Pd(THM)_4$ Mean ± Std Dev |
|---|---|---|
| Clusters PF (%) | 74.6925 ± 8.13 | 74.23 ± 8.90 |
| R1 Error Rate (%) | 0.4725 ± 0.12 | 0.52 ± 0.11 |
| R2 Error Rate (%) | 0.43 ± 0.08 | 0.475 ± 0.08 |
| R1 Intensity Cycle 1 | 1249.25 ± 179.06 | 1404.5 ± 119.50 |
| R2 Intensity Cycle 1 | 1328.25 ± 195.68 | 1496 ± 140.01 |
| R3 Intensity Cycle 1 | 1194.75 ± 160.90 | 1339 ± 101.82 |
| R4 Intensity Cycle 1 | 1123 ± 125.10 | 1208 ± 86.27 |
| Mismatches read 1 (%) | 0.4525 ± 0.08 | 0.475 ± 0.09 |
| Mismatches read 2 (%) | 0.5975 ± 0.10 | 0.615 ± 0.11 |
| Resynthesis (%) | 89.8939 | 86.009 |

Example 9

In this example, an alternative route for the preparation of the active Pd (0) complex is described. $Pd(THP)_{2-4}$ was prepared and isolated by reacting $Pd(PPh_3)_4$ with THP in a ligand exchange reaction. Its cleavage activity was compared to the in situ generated Pd(0) complex from allyl palladium(II) chloride dimer $(Pd(C_3H_5)Cl)_2$ and THP as described in Example 1.

Preparation Method

Under nitrogen, $Pd(PPh_3)_4$ was dissolved in dry, degassed dichloromethane to give a yellow solution. Aqueous THP solution (4.1 equivalents) was added to obtain a biphasic mixture, which was stirred for 2.5 hours. The yellow color transferred from the organic to the aqueous layer. The reaction was worked-up by siphoning off the organic layer and rinsing the aqueous phase with additional DCM. The aqueous phase was dried down under reduced pressure and co-evaporated with tetrahydrofuran, and the resulting orange oil was dried under high vacuum. The yield was almost quantitative. Product LC-MS analysis indicated the presence of Pd(THP)$_2$ [Pd(THP)$_2$+H+; Expected: 523 Da, Found: 523 Da].

Use for P15 Linearization

Figure 7:
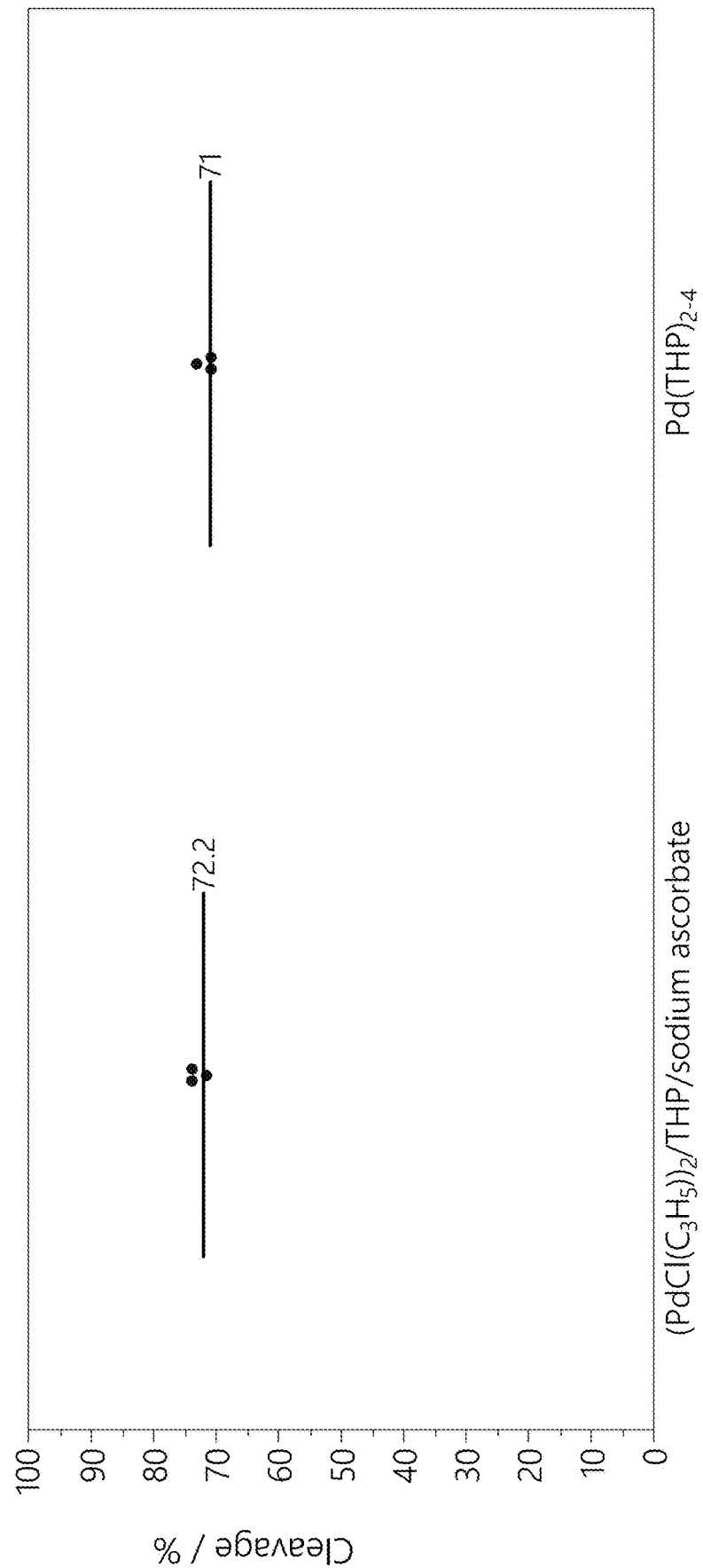
FIG. 7 shows the P15 cleavage activity of Pd(THP)$_{2-4}$ (10 mg/mL) compared to a formulation of (Pd(C$_3$H$_5$)Cl)$_2$ (6 mM), THP (60 mM), and sodium ascorbate (6 mM).

Pd(THP)$_{2-4}$ was formulated in aqueous buffer at 10 mg/mL, and its P15 cleavage activity was assessed using a plate-based assay. This assay utilizes a 96-well plate grafted with P15/P17 surface primers. An intercalating fluorescent dye is used to quantify double-stranded DNA present before and after read 1 linearization; percentage cleavage can be calculated from the amount of double-stranded DNA remaining. For formulations of Pd(THP)$_{2-4}$, P15 cleavage activity was comparable to a Pd mixture prepared in situ from (Pd(C$_3$H$_5$)Cl)$_2$ (6 mM), THP (60 mM), and sodium ascorbate (6 mM) (FIG. 7). It was observed that the two methods had comparative cleavage performance.

Example 10

In this example, alternative nickel based chemical cleavage reagent were prepared and tested in the cleavage of an allyl dT nucleotide containing DNA strand.

First, both THP and THM phosphine ligands were used in various equivalents to react with NiCl$_2$ in the preparation of nickel complexes. The Ni-THP (1:4 or 1:10 ratio) yielded the same cleavage product as the palladium containing reagent described in Example 1. Interestingly, Ni-THM where the phosphine ligand has shorter alkyl chain (thus smaller cone angle) did not demonstrate the same cleavage activity when complexed with nickel.

Figure 8:
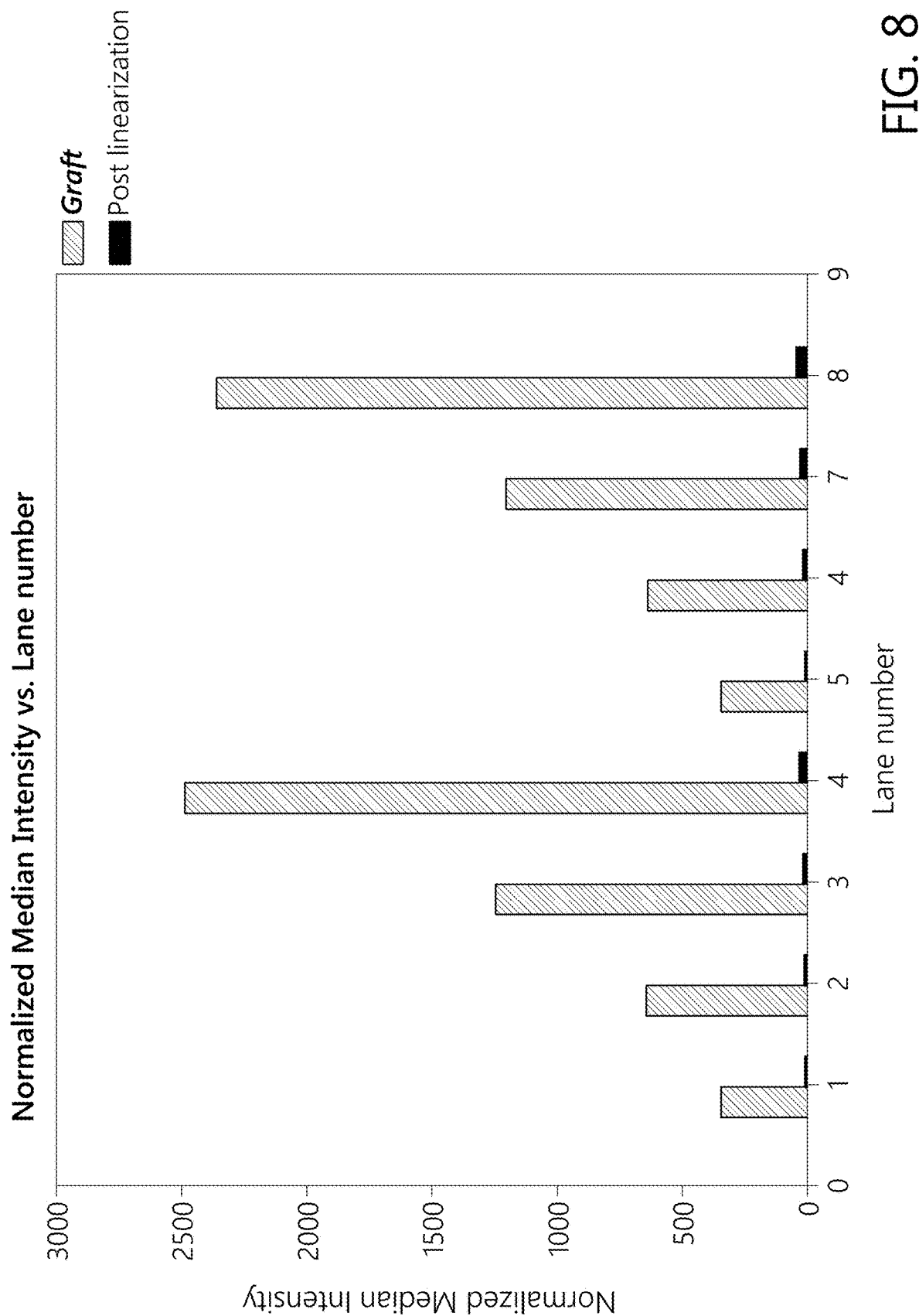
FIG. 8 is a bar chart of fluorescent intensity of the flow cell grafted with P15/P7 primers after treatment with Pd-THP or Ni-THP.

The cleavage activity of Ni-THP on surface was tested and compared with that of Pd-THP. The experiment was carried out in a HiSeq™ flow cell grafted with P15/P7 primers and tracer oligos. The tracer oligos have four allyldT in the sequence and 3' fluorescent label. Upon cleavage of the allyldT by the Ni-THP or Pd-THP complexes, the fluorescent signal from the flowcell would be eliminated. Flow cell was grafted with 1.1 μM P15/P7 and additional 5% to 40% tracer oligos, then scanned on Typhoon to confirm the success of grafting. Chemical linearization was performed at 60° C. for 10 min. Lanes 1 to 4 were treated with Pd-THP complex (generated in situ from (Pd(C$_3$H$_5$)Cl)$_2$ (10 mM), THP (100 mM), and sodium ascorbate (10 mM)) as control, lanes 5 to 8 were treated with 10 mM Ni-THP (1:10) complex. Fluorescence intensity was then obtained on Typhoon to assess the extent of chemical linearization. Lane layout: 5% tracer=55 nM (Lanes 1, 5); 10% tracer=110 nM (Lanes 2, 6); 20% tracer=220 nM (Lanes 3, 7); 40% tracer=440 nM (Lanes 4, 8). FIG. 8 shows the normalized median fluorescent intensity before and after cleavage and Ni-THP has demonstrated efficient cleavage activity that was comparable to Pd-THP.

Example 11

In this example, an alternative azo-arene based linker as a bioorthogonal cleavable linker for chemical linearization by an aqueous sodium dithionite (Na$_2$S$_2$O$_4$) solution is described.

Schemes 5 and 6 illustrate the preparation of azo-phosphoramidites 1 and 2 respectively.

Scheme 5

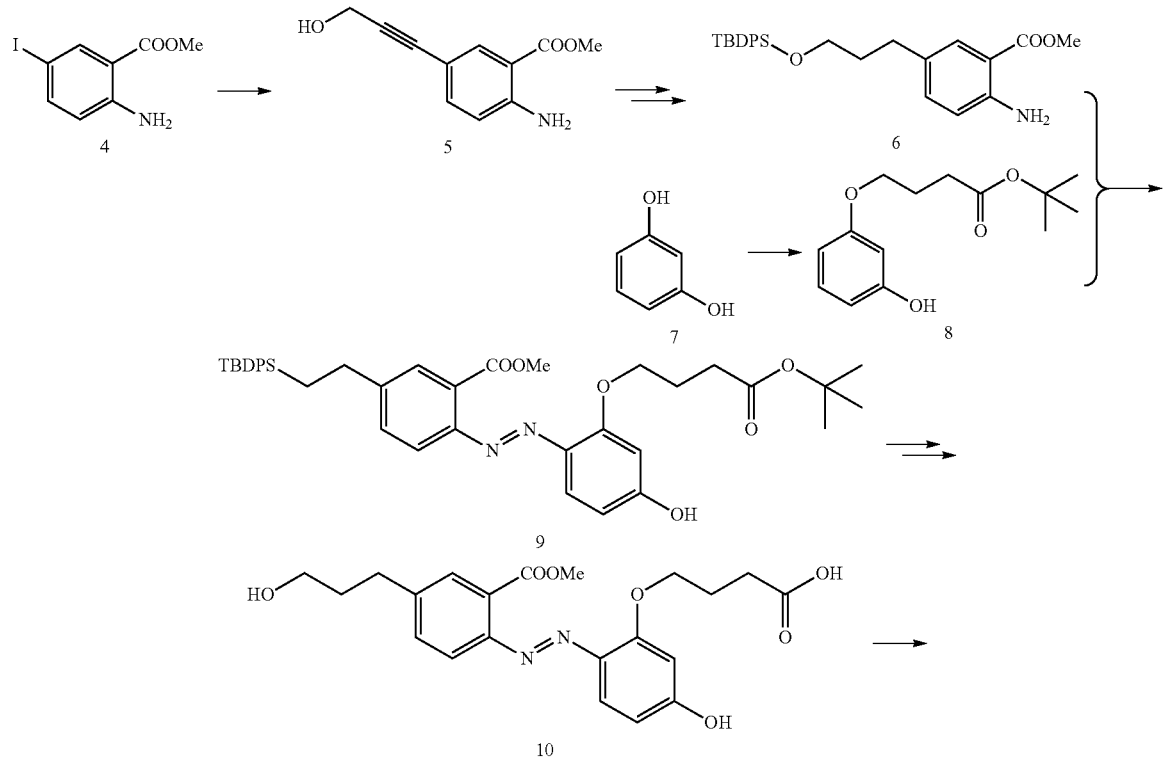

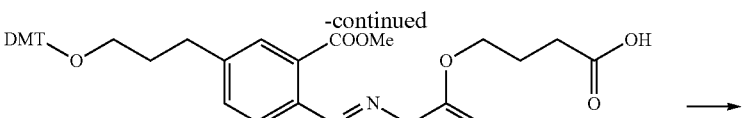
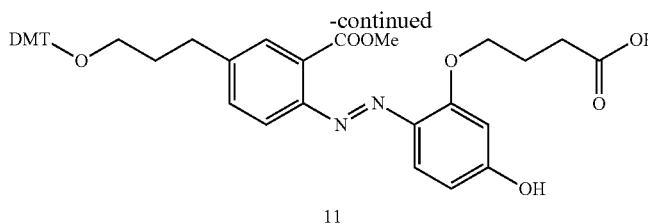

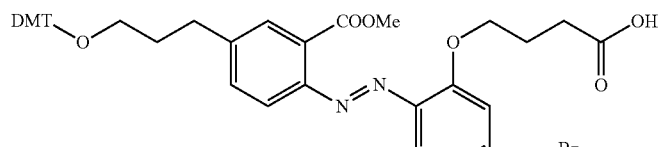

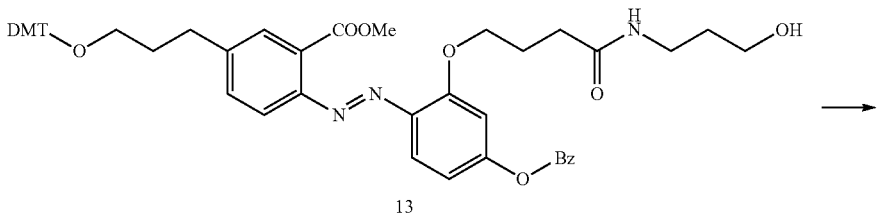

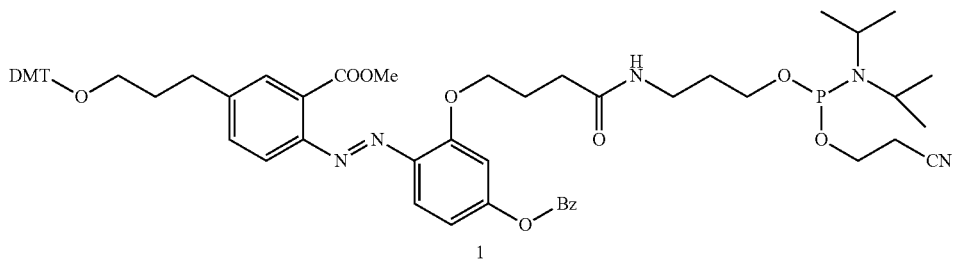

Compound 5. Under $N_2$, a suspension of methyl 2-amino-5-iodobenzoate (4) (2.77 g, 10 mmol), Pd(PPh$_3$)$_4$ (1.159 mg, 1 mmol), CuI (381 mg, 2 mmol), Et$_3$N (4.2 mL, 30 mmol) and propargyl alcohol (1.75 ml, 30 mmol) in DMF (20 mL) was stirred at rt for 15 h. TLC analysis (petrol ether:ethyl acetate 1:1) indicated the fully consumption of starting material. The reaction was quenched with 200 ml sat. NaCl solution. Ethyl acetate:petrol ether 1:1 (200 ml) was added to the mixture and the aqueous layer was extracted with ethyl acetate:petrol ether 1:1 three times. After drying the combined organics over MgSO$_4$, the solution was concentrated and purified by silica gel chromatography (petrol ether:ethyl acetate 80:20 to ethyl acetate), giving Compound 5 as a yellow oil (1.88 g, 92%). $^1$H NMR (CDCl$_3$) δ 3.78 (s, 3H), 4.25 (s, 2H, ≡CCH$_2$), 7.27-7.36 (m, 2H, arom.H), 7.58-7.65 (m, 1H, arom.H).

Compound 6. Under $N_2$, a solution of Compound 5 (1.88 mg, 9.2 mmol) and imidazole (1.83 g, 27.6 mmol) in dry DMF (25 ml) was added t-butyldiphenylsilylchloride (1.06 g, 12 mmol). The reaction was followed by TLC and completed after stirring for 1 hour at room temperature. The reaction was quenched with sat. NaHCO$_3$ solution and extracted with Ethyl acetate:petrol ether 1:1 (2×). After drying the combined organics over MgSO$_4$, the solvent was removed under vacuum. The crude mixture was then dissolved in EtOH and treated with EtSiH and Pd—C(10%). The reaction mixture was refluxed under $N_2$ for 16 hours. TLC analysis (petrol ether:ethyl acetate 8:2) indicated the fully consumption of starting material. The reaction mixture was filtered, concentrated down and purified by silica gel chromatography (petrol ether to petrol ether:ethyl acetate 1:1), giving Compound 6 as a yellow oil (3.37 g, 82%). $^1$H NMR (CDCl$_3$) δ 1.04 (s, 9H, 3×CH3), 1.70-1.77 (m, 2H, CH$_2$), 2.56 (t, 2H, CH$_2$), 3.58 (t, 2H, OCH$_2$), 3.60 (s, 3H, OCH$_3$), 6.62-6.65 (m, 1H, arom.H), 7.03-7.06 (m, 1H, arom.), 7.27-7.63 (m, 11H, arom.H).

Compound 8. To a suspension of resorcinol (2.2 g, 20 mmol) and K$_2$CO$_3$ (2.76 g, 20 mmol) in DMF (40 ml) tert-butyl 4-bromobutanoate (2.2 g, 10 mmol) was added under N$_2$. The reaction mixture was stirred at rt for 15 h. TLC analysis (petrol ether:ethyl acetate 7:3) indicated the 90% consumption of starting material resorcinol. The reaction was quenched with 300 ml sat. NaCl solution. Ethyl acetate:petrol ether 1:1 (300 ml) was added to reaction mixture and the aqueous layer was extracted with ethyl acetate:petrol ether 1:1 three times. After drying the combined organics over MgSO$_4$, the solution was concentrated and purified by silica gel chromatography (petrol ether to petrol ether:ethyl acetate 50:50), giving Compound 8 as a yellow oil (2.2 g, 88%). $^1$H NMR (CDCl$_3$) δ 1.27 (s, 9H), 1.91-1.98 (m, 2H, CH$_2$), 2.22 (t, 2H, CH$_2$), 3.27 (t, 2H, OCH$_2$), 6.36-6.46 (m, 3 arom.H), 7.09 (t, 1 arom.H)

Compound 9. Compound 5 (450 mg, 1 mmol) was dissolved in a solution of acetone/water (1:1) (2.5 mL). The mixture was cooled to 0° and concentrated HCl (0.5 mL) was added. After 5 minutes sodium nitrite (93 mg, 1.2 mmol) in water (1 mL) was added dropwise and the mixture was stirred for 1 hour at 0° C. In the same time, were solubilized Compound 8 (252 mg, 1 mmol), Na$_2$CO$_3$ (210 mg, 2 mmol) and NaOH (160 mg, 4 mmol) in a solution of acetone/water (1:1) (3 mL). The first solution was added dropwise at the second at 0° C. After the addition was completed, the mixture was warmed up to rt and stirred for an additional hour. Reaction mixture was neutralized with 1M HCl and then extracted with DCM (3×50 mL). Organic phase was dried over MgSO$_4$, concentrated and purified by silica gel chromatography (petrol ether to petrol ether:ethyl acetate 1:1). Compound 9 was obtained as an orange/red oil (400 mg, 56%). $^1$H NMR (400 MHz, DMSO-d6) δ 1.02 (s, 9H, 3×CH3), 1.27 (s, 9H), δ 1.69-1.76 (m, CH$_2$), 1.91-1.97 (m, 2H, CH$_2$), 2.20 (t, 2H, CH$_2$), 2.53 (t, 2H, CH$_2$), 3.34 (t, 2H, OCH$_2$), 3.54 (t, 2H, OCH$_2$), 3.62 (s, 3H, OCH$_3$), 6.36-6.46 (m, 4 arom.H), 7.00-7.06 (m, 1H, arom.H), 7.09 (t, 1 arom.H), 7.27-7.63 (m, 11H, arom.H).

Compound 11. Compound 9 (3.55 g, 5 mmol) was dissolved in DCM (50 ml). The solution was treated with TFA (10 ml) at rt and stirred overnight. Then TFA was removed under reduce pressure and co-evaporated with toluene. The residue was partitioned between NaCl and DCM. The aqueous layer was extracted with DCM 3 times. The combined organic layer was dried over MgSO$_4$ and concentrated down. The crude product was dissolved in THF (15 ml) and treated with TBAF (1M, 5 ml). The reaction was monitored by TLC (DCM/MeOH 90:10). The solvent was removed under reduce pressure and the residue was partitioned between NaCl and DCM (+10% MeOH). The aqueous layer was extracted with DCM (+10% MeOH) 3 times. The combined organic layer was dried over MgSO$_4$ and concentrated down. The residue was co-evaporated with pyridine 3×. The reside was dissolved in Py/CH$_3$CN (10/10 ml) and Hunig's base (3.7 ml, 15 mmol), DMT-Cl (5.07 g, 15 mmol) was added. The mixture was stirred at rt for 2 hours. TCL (DCM:MeOH 95:5) indicated the completion of the reaction. The mixture was concentrated down, dissolved in DCM, and washed with Na$_2$CO$_3$. The combined organic layer was dried over MgSO$_4$, concentrated and purified by silica gel chromatography (petrol ether:ethyl acetate 8:2 to ethyl acetate+1% NEt$_3$). Compound 11 was obtained as an orange/red oil (2.37 g, 66%). $^1$H NMR (400 MHz, DMSO-d6) δ 1.70-1.79 (m, 2H, CH$_2$), 1.90-1.97 (m, 2H, CH$_2$), 2.24 (t, 2H, CH$_2$), 2.54 (t, 2H, CH$_2$), 3.26 (t, 2H, OCH$_2$), 3.58 (t, 2H, OCH$_2$), 3.63 (s, 3H, OCH$_3$), 3.71 (s, 6H, OMe), 6.79-6.89 (m, 4H, aromatics), 7.03-7.06 (m, 1H, arom.H), 7.10 (t, 1 arom.H), 7.13-7.63 (m, 13H, arom.H).

Compound 12. Compound 11 (1.05 g, 1.46 mmol) and DMAP (18 mg, 0.15 mmol) was dissolved in 7 ml of anhydrous pyridine under N$_2$. The reaction mixture was then cooled to 0° C. and benzoyl chloride (0.5 ml, 4.4 mmol) was added dropwise. The reaction mixture was slowly warmed up to rt and stirred for one hour during which time solution turned cloudy. TLC analysis indicated complete consumption of starting material. The reaction was quenched with sat. NaHCO$_3$ solution. The aqueous layer was extracted with DCM 3 times. The combined organic layer was dried over MgSO$_4$, concentrated and purified by silica gel chromatography (petrol ether:ethyl acetate 8:2 to ethyl acetate+1% NEt$_3$) to give Compound 12 as a yellow oil (930 mg, 78%). $^1$H NMR (400 MHz, DMSO-d6) δ 1.69-1.76 (m, 2H, CH$_2$), 1.91-1.97 (m, 2H, CH$_2$), 2.20 (t, 2H, CH$_2$), 2.53 (t, 2H, CH$_2$), 3.24 (t, 2H, OCH$_2$), 3.54 (t, 2H, OCH$_2$), 3.62 (s, 3H, OCH$_3$), 3.71 (s, 6H, OMe), 6.79-6.86 (m, 4H, aromatics), 7.01 (t, 1 arom.H), 7.04-7.11 (m, 3H, arom.H), 7.13-7.63 (m, 13H, arom.H), 7.94-8.36 (m, 3H, arom.H).

Compound 13. Compound 12 (340 mg, 0.5 mmol) was dissolved in 3 ml of anhydrous DMF under N$_2$ and Hunig's base (0.26 ml, 1.5 mmol) was added. The reaction mixture was then treated with TSTU (196 mg, 0.65 mmol) and kept at rt. After 30 min, TLC analysis (EtOAc) indicated that the reaction completed. Then 3-aminopropanol (38 µl, 0.5 mol) was added to the reaction mixture and stirred at rt for 4 h. TLC analysis indicated complete consumption of starting material. The reaction was quenched with sat. NaHCO$_3$ solution. The aqueous layer was extracted with DCM 3 times. The combined organic layer was dried over MgSO$_4$, concentrated, co-evaporated with xylene (3×) and purified by silica gel chromatography (petrol ether:ethyl acetate 8:2 to ethyl acetate+1% NEt$_3$) to give Compound 13 as an orange oil (320 mg, 73%). $^1$H NMR (400 MHz, DMSO-d6) δ 1.67-1.79 (m, 4H, CH$_2$), 1.91-1.97 (m, 2H, CH$_2$), 2.20 (t, 2H, CH$_2$), 2.53 (t, 2H, CH$_2$), 3.24 (t, 2H, OCH$_2$), 3.45 (t, 2H, OCH$_2$), 3.51 (t, 2H, NCH$_2$), 3.54 (t, 2H, OCH$_2$), 3.69 (s, 3H, OCH$_3$), 3.71 (s, 6H, OMe), 6.79-6.86 (m, 4H, aromatics), 7.01 (t, 1 arom.H), 7.04-7.11 (m, 3H, arom.H), 7.13-7.69 (m, 13H, arom.H), 7.94-8.40 (m, 3H, arom.H).

Compound 1. Compound 13 (320 mg, 0.36 mmoles) was dried under high vacuum lane. Anhydrous DCM (2 ml) was added under N$_2$ and stirred with molecular sieves for 10 min at rt To the solution, Hunig's base (0.19 ml, 1.1 mmoles) was added and followed by 2-Cyanoethyl N,N-diisopropylchlorophosphoramidite (102 mg, 0.43 mmol). The reaction was stirred at rt under N$_2$ for 3 h. The reaction was followed by TLC (PE/EtOAc, 8:2). The reaction concentrated to syrup under vacuum. The residue was purified by column (petrol ether:ethyl acetate 8:2 to ethyl acetate, PE/EtOAc+1% NEt$_3$) to give Compound 1 as an orange oil (190 mg, 50%). The product was partially decomposed on the column. $^1$H NMR (400 MHz, DMSO-d6) δ 0.96-1.27 (m, 12H), 1.68-1.79 (m, 4H, CH$_2$), 1.91-1.97 (m, 2H, CH$_2$), 2.20 (t, 2H, CH$_2$), 2.53 (t, 2H, CH$_2$), 2.58-2.74 (m, 2H, CH$_2$CN), 3.24 (t, 2H, OCH$_2$), 2.93 (m, 2H, NCH), 3.44 (t, 2H, NCH$_2$), 3.42-3.54 (m, 4H, OCH$_2$), 3.69 (s, 3H, OCH$_3$), 3.71 (s, 6H, OMe), 6.79-7.01 (m, 5H, aromatics), 7.04-7.11 (m, 3H, arom.H), 7.13-7.69 (m, 13H, arom.H), 7.94-8.40 (m, 3H, arom.H).

Scheme 6
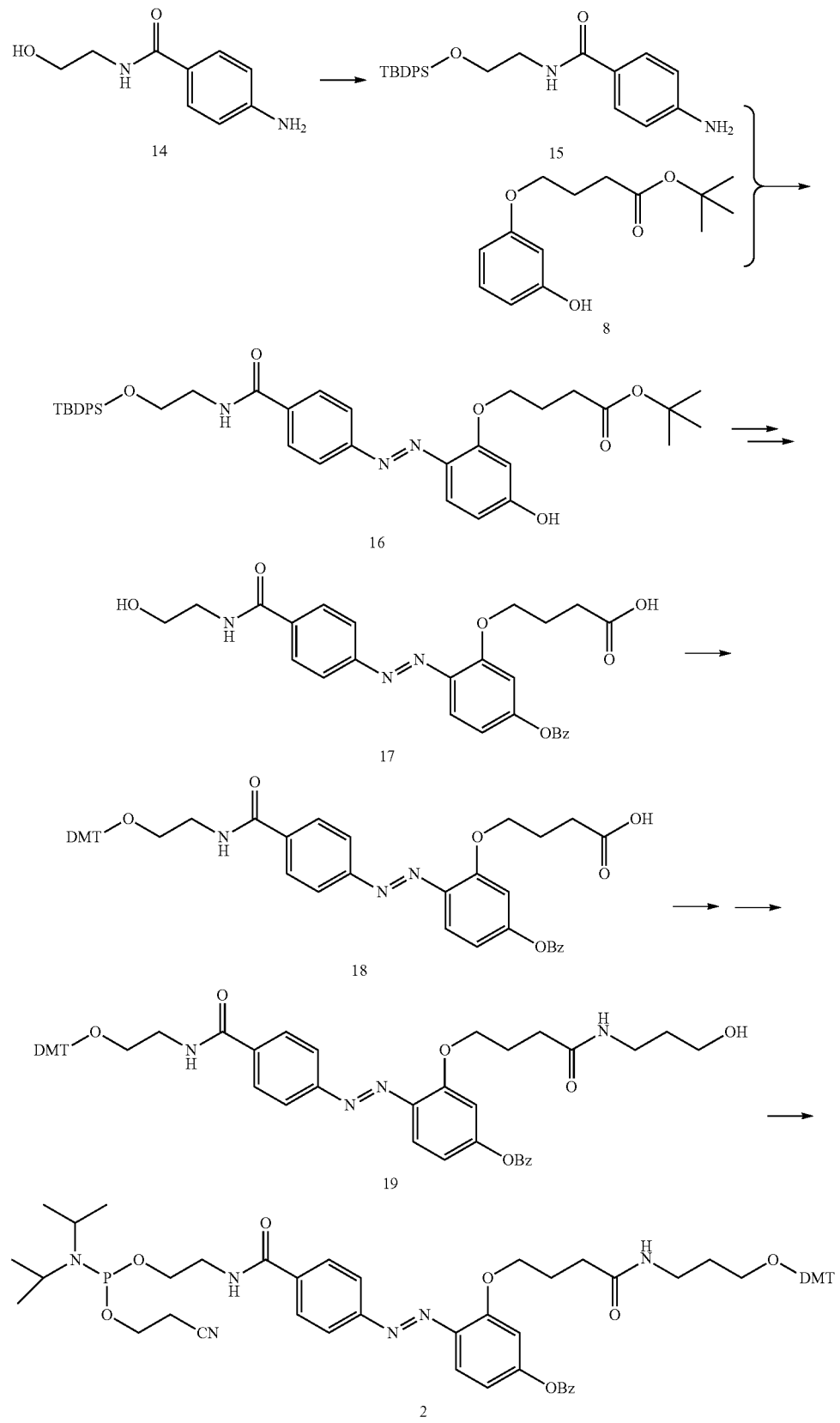

Compound 15. Under N$_2$, a solution of Compound 14 (3.6 g, 20 mmol) and imidazole (3.72 g, 60 mmol) in dry DMF (25 ml) was added t-butyldiphenylsilylchloride (2.3 g, 26 mmol). The reaction was followed by TLC and completed after stirring for 1 hour at rt. The reaction was quenched with sat. NaHCO$_3$ solution and extracted with Ethyl acetate: petrol ether 1:1 (2×). After drying the combined organic layer over MgSO$_4$, the reaction mixture was filtered, concentrated down and purified by silica gel chromatography (petrol ether to petrol ether:ethyl acetate 1:1), giving Compound 15 as an off-yellow oil (7.19 g, 86%). $^1$H NMR (DMSO-d$_6$) δ 0.99 (s, 9H, 3×CH3), 3.38-3.46 (m, 2H, NCH$_2$), 3.92 (t, 2H, OCH$_2$), 5.59 (s, 2H, NH$_2$), 6.50-6.54 (d, 2H, arom.H), 7.37-7.66 (m, 13H, arom.H), 8.05 (d, 1H, NH).

Compound 16. Under N$_2$, a solution of Compound 15 (840 mg, 2 mmol) in dry DCM (10 ml) was added nitrosyl tetrafluoroborite (234 mg, 2 mmol) at 0° C. The reaction was followed by TLC and starting material disappeared after stirring for 1 hour at 0° C. Then Compound 8 (756 mg, 3 mmol) was added to the reaction mixture. The reaction mixture was slowly warmed up to rt and stirred for 4 h. The reaction was followed by TLC. Upon completion, the reaction was quenched with sat. NaHCO$_3$ solution and extracted with DCM (2×). After drying the combined organic layer over MgSO$_4$, the reaction mixture was filtered, concentrated down and purified by silica gel chromatography (petrol ether to petrol ether:ethyl acetate 1:1), giving Compound 16 as an orange oil (1.12 g, 82%). $^1$H NMR (DMSO-d$_6$) δ 0.99 (s, 9H, 3×CH3), 1.27 (s, 9H, 3× CH$_3$), 1.91-1.98 (m, 2H, CH$_2$), 2.22 (t, 2H, CH$_2$), 3.27 (t, 2H, OCH$_2$), 3.38-3.46 (m, 2H, NCH$_2$), 3.92 (t, 2H, OCH$_2$), 6.36-6.46 (m, 3 arom.H), 6.50-6.56 (d, 2H, arom.H), 7.10 (t, 1 arom.H), 7.37-7.66 (m, 13H, arom.H), 8.06 (d, 1H, NH).

Compound 17. Compound 16 (1.1 g, 1.64 mmol) and DMAP (20 mg, 0.16 mmol) was dissolved in 8 ml of anhydrous pyridine under N$_2$. The reaction mixture was then cooled to 0° C. and benzoyl chloride (0.17 ml, 1.5 mmol) was added drop wisely. The reaction mixture was slowly warmed up to rt and stirred for one hour during which time solution turned cloudy. TLC analysis indicated complete consumption of starting material. The reaction was quenched with sat. NaHCO$_3$ solution. The aqueous layer was extracted with DCM 3×. The combined organic layer was washed with H$_2$SO$_4$, dried over MgSO$_4$ and concentrated down. The resulted crude mixture was dissolved in DCM (14 ml). The solution was treated with TFA (1.4 ml) at rt and stirred overnight. The reaction was monitored by TLC (petrol ether:ethyl acetate 1:1). The TFA was removed under reduce pressure and co-evaporated with toluene. The residue was partitioned between NaCl and DCM. The aqueous layer was extracted with DCM 3 times. The combined organic layer was dried over MgSO$_4$ and concentrated down. The crude product was dissolved in THF (8 ml) and treated with TBAF (1M, 1.6 ml). The reaction was monitored by TLC (DCM/MeOH 9:11). The solvent was removed under reduce pressure and the residue was partitioned between NaCl and DCM (+10% MeOH). The aqueous layer was extracted with DCM (+10% MeOH) 3 times. The combined organic layer was dried over MgSO$_4$ and concentrated and purified by silica gel chromatography (DCM to DCM: MeOH 9:1). Compound 17 was obtained as an orange/red oil (515 g, 64%). $^1$H NMR (400 MHz, DMSO-d6) δ 1.56-1.64 (m, 2H, CH$_2$), 2.01 (t, 2H, CH$_2$), 3.24 (t, 2H, NCH$_2$), 3.52 (t, 2H, OCH$_2$), 4.25 (t, 2H, OCH$_2$), 6.79-6.89 (m, 1H, arom.H), 7.03-7.06 (m, 1H, arom.H), 7.13-7.63 (m, 10H, arom.H), 8.56 (t, 1H, NH).

Compound 18. Compound 17 (500 mg, 1 mmol) was dissolved in py/CH$_3$CN (5/5 ml) and Hunig's base (0.87 ml, 5 mmol), DMT-Cl (1 g, 3 mmol) was added. The mixture was stirred at rt for 2 hours. TCL (DCM:MeOH 95:5) indicated the completion of the reaction. The mixture was concentrated down, dissolved in DCM, and washed with Na$_2$CO$_3$. The combined organic layer was dried over MgSO$_4$, concentrated and purified by silica gel chromatography (petrol ether:ethyl acetate 8:2 to ethyl acetate+1% NEt$_3$). Compound 18 was obtained as an orange/red oil (653 mg, 83%). $^1$H NMR (400 MHz, DMSO-d6) δ 1.16-1.24 (m, 2H, CH$_2$), 2.01 (t, 2H, CH$_2$), 3.24 (t, 2H, NCH$_2$), 3.52 (t, 2H, OCH$_2$), 3.69 (s, 6H, OMe), 4.25 (t, 2H, OCH$_2$), 6.76-6.89 (m, 4H, arom.H), 7.03-8.23 (m, 21H, arom.H), 8.86 (t, 1H, NH).

Compound 19. Compound 18 (350 mg, 0.5 mmol) was dissolved in 3 ml of anhydrous DMF under N$_2$ and Hunig's base (0.26 ml, 1.5 mmol) was added. The reaction mixture was then treated with TSTU (196 mg, 0.65 mmol) and kept at rt. After 30 min, TLC analysis (petrol ether: EtOAc 2:8) indicated that the reaction completed. Then 3-aminopropanol (38 μl, 0.5 μmol) was added to the reaction mixture and stirred at rt for 4 h. TLC analysis indicated complete consumption of starting material. The reaction was quenched with sat. NaHCO$_3$ solution. The aqueous layer was extracted with DCM 3×. The combined organic layer was dried over MgSO$_4$, concentrated, co-evaporated with xylene (3×) and purified by silica gel chromatography (petrol ether:ethyl acetate 8:2 to ethyl acetate+1% NEt$_3$) to give Compound 19 as an orange oil (223 mg, 52%). $^1$H NMR (400 MHz, DMSO-d6) δ 1.67-1.79 (m, 4H, CH$_2$), 1.91-1.97 (m, 2H, CH$_2$), 2.05 (t, 2H, CH$_2$), 2.53 (t, 2H, CH$_2$), 3.24 (t, 2H, OCH$_2$), 3.45 (t, 2H, OCH$_2$), 3.51 (t, 2H, NCH$_2$), 3.57 (t, 2H, OCH$_2$), 3.71 (s, 6H, OMe), 6.79-6.86 (m, 4H, aromatics), 7.01 (t, 1 arom.H), 7.04-7.11 (m, 3H, arom.H), 7.13-7.69 (m, 13H, arom.H), 7.74-8.40 (m, 4H, arom.H), 8.76 (t, 1H, NH).

Compound 2. Compound 19 (223 mg, 0.26 mmol) was dried under high vacuum lane. Anhydrous DCM (1.5 ml) was added under N$_2$ and stirred with molecular sieves for 10 min at rt. To the solution, Hunig's base (0.14 ml, 0.78 mmol) was added and followed by 2-Cyanoethyl N,N-diisopropylchlorophosphoramidite (76 ul, 0.34 mmol). The reaction was stirred at rt under N$_2$ for 3 h. The reaction was followed by TLC (PE/EtOAc, 2:8). The reaction concentrated to syrup under vacuum. The residue was purified by column (petrol ether:ethyl acetate 8:2 to ethyl acetate+1% NEt$_3$) to give Compound 2 as an orange oil (152 mg, 56%). The product was partially decomposed on the column. $^1$H NMR (400 MHz, DMSO-d6) δ 0.96-1.27 (m, 12H), 1.68-1.79 (m, 4H, CH$_2$), 1.91-1.97 (m, 2H, CH$_2$), 2.19-2.22 (m, 2H, CH$_2$), 2.51-2.54 (m, 2H, CH$_2$), 2.58-2.74 (m, 2H, CH$_2$CN), 3.22-3.26 (m, 2H, OCH$_2$), 2.93 (m, 2H, NCH), 3.44 (t, 2H, NCH$_2$), 3.42-3.54 (m, 4H, OCH$_2$), 3.71 (s, 6H, OMe), 6.79-7.01 (m, 5H, aromatics), 7.04-7.11 (m, 3H, arom.H), 7.13-7.69 (m, 13H, arom.H), 7.94-8.40 (m, 3H, arom.H), 8.76 (t, 1H, NH).

Then, two short oligos (Oligo azo-1 and Oligo azo-2) incorporating the two azo-phosphoramidites Compounds 1 and 2 respectively were synthesized to evaluate the cleavage efficiency. Oligo azo-1 has an absorption at 450 nm and an orange color. After the cleavage, the azo bond is broken and results in the loss of the orange color. After adding 0.1 M Na$_2$S$_2$O$_4$ solution at rt, the orange color of the oligo solution disappeared instantly, which indicated a very efficient cleavage of the azo bond. HPLC analysis of the oligo azo-1 and the cleavage products also confirmed the same result. HPLC analysis of oligo azo-2 cleavage test showed a clean and instant breakage of azo bond treated by 0.1 M $Na_2S_2O_4$ solution at rt.

Oligo azo-1: 5'-GAX$^1$CTA-3'

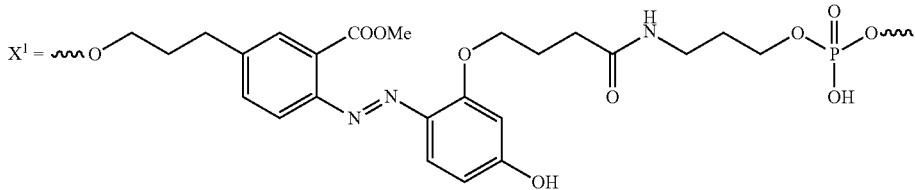

Oligo azo-2: 5'-GAX$^2$CTA-3'

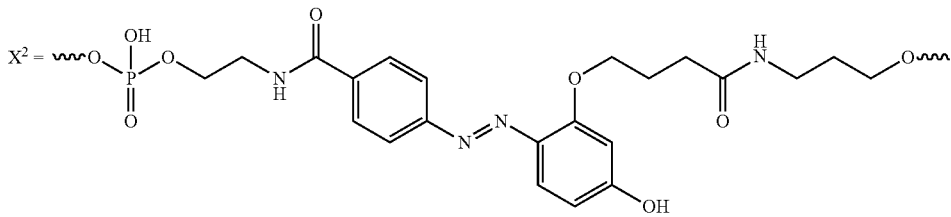

Furthermore, the compatibility of Oligo azo-1 with the SBS sequencing reagents were also tested. First, 10 μM of Oligo azo-1 (10 μL) was incubated in 90 μL of incorporation mix (IMX), cleavage mix (CMS) and scan mix (USM) at 60° C. for 60 minutes. HPLC analysis showed that Oligo azo-1 was completely stable in IMX, 90% Oligo azo-1 was decomposed in CMS and 50% Oligo azo-1 was left in USM. A small improvement was observed for Oligo azo-2. Degradation was reduced to 44% for Oligo azo-2 as compared to 66% degradation for Oligo azo-1 when both oligos were incubated at 60° C. for 60 minutes in CMS solution (10 μL).

What is claimed is:

1. A method of linearizing a plurality of immobilized double-stranded polynucleotides, comprising:
providing a solid support comprising double-stranded polynucleotides, wherein each double-stranded polynucleotide comprises a first strand and a second strand, wherein the first strand and the second strand are immobilized to the solid support at their 5' ends, and wherein each first strand comprises a first cleavage site capable of undergoing chemical cleavage by a transition metal complex, wherein the transition metal complex is a palladium complex;
contacting the double-stranded polynucleotides with an aqueous solution of the palladium complex, thereby cleaving one or more first strands at the first cleavage site, and generating one or more cleaved first nucleic acids and cleaved immobilized first strands; and
removing the cleaved first nucleic acids from the solid support;
wherein the first cleavage site comprises a structure of formula (II'):

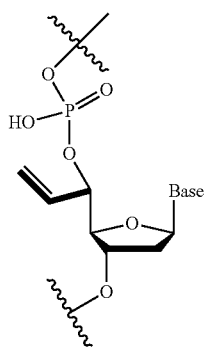

wherein Base is adenine, guanine, cytosine, thymine, or uracil, or a derivative thereof.

2. The method of claim 1, wherein each first strand is extended from a first extension primer immobilized to the solid support, and the first extension primer comprises the first cleavage site.

3. The method of claim 2, wherein the first extension primer comprises a P5 sequence or a modified P5 sequence.

4. The method of claim 1, wherein Base in formula (II') is thymine.

5. The method of claim 1, wherein the palladium complex is a palladium (0) complex.

6. The method of claim 5, wherein the palladium (0) complex is Pd(THP)$_2$, Pd(THP)$_4$, Pd(THM)$_4$, or combinations thereof.

7. The method of claim 1, wherein the 3' end of each cleaved immobilized first strand comprises a protecting group.

8. The method of claim 7, wherein the protecting group is a 3' end phosphate moiety having a structure of formula (I):

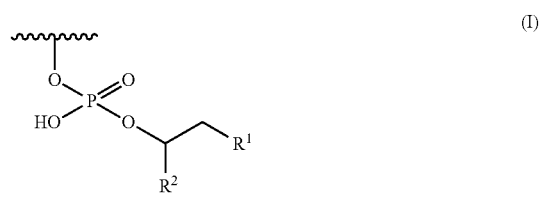

wherein:
$R^1$ is —NH$_2$, —OH, —NHC(O)OR$^a$ or —OCH$_2$OSi(R$^b$)$_3$;
$R^a$ is C$_{1-4}$ alkyl, tert-butyl, allyl, benzyl, or 9-fluorenylmethyl;
each $R^b$ is independently selected from the group consisting of C$_{1-4}$alkyl and phenyl; and
$R^2$ is H, C$_{1-4}$ alkyl, an optionally substituted tetrahydrofuran, or a nucleotide.

9. The method of claim 1, wherein each second strand is extended from a second extension primer immobilized to the solid support, and each second strand comprises a second cleavage site that is not capable of undergoing chemical cleavage by the palladium complex used for chemical cleavage of the first strand.

10. The method of claim 9, wherein the second extension primer comprises a P7 nucleotide sequence or a modified P7 nucleotide sequence or a P17 nucleotide sequence.

11. The method of claim 9, wherein the second cleavage site is cleaved by a method selected from the group consisting of chemical cleavage, photo cleavage, enzymatic cleavage, and a combination thereof.

12. The method of claim 11, wherein the second cleavage site is cleaved by a chemical cleavage and wherein the second cleavage site comprises a diol linker or an azobenzene linker.

13. The method of claim 12, wherein the diol linker comprises a structure of formula (VIII):

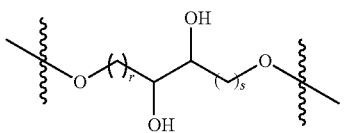

(VIII)

wherein r is 2, 3, 4, 5, or 6; and s is 2, 3, 4, 5, or 6.

14. The method of claim 13, wherein the diol linker is cleavable by a periodate salt.

15. The method of claim 12, wherein the azobenzene linker comprises a structure of Formula (X):

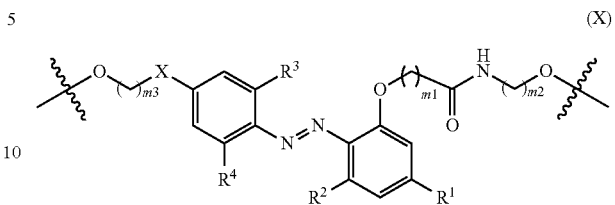

(X)

wherein $R^1$ is H, hydroxyl, or a protected hydroxyl;

$R^2$ is H, $C_{1-6}$ alkyl, or $C_{1-6}$ alkoxy;

each $R^3$ and $R^4$ is independently H, halo, —C(O)OR$^5$, or —C(O)NHR$^6$;

each $R^5$ and $R^6$ is independently H, $C_{1-6}$ alkyl, or $C_{6-10}$ aryl;

X is —C(O)—, —CH$_2$—, or —C(O)NH—; and each m1, m2 and m3 is independently 1, 2, 3, 4, 5, or 6.

16. The method of claim 15, wherein the azobenzene linker is cleavable by Na$_2$S$_2$O$_4$.

17. The method of claim 1, wherein the double-stranded polynucleotides are immobilized to the solid support through covalent bonding.

18. The method of claim 5, wherein Base in formula (II') is thymine.

19. The method of claim 5, wherein the Pd(0) complex is generated in situ from a Pd(II) complex with a water soluble phosphine.

* * * * *